(12) United States Patent
Liu et al.

(10) Patent No.: US 12,227,557 B2
(45) Date of Patent: Feb. 18, 2025

(54) CD80 AND CD86 BINDING PROTEIN COMPOSITIONS AND USES THEREOF

(71) Applicants: ONCOC4, INC., Rockville, MD (US); CHILDREN'S NATIONAL MEDICAL CENTER, Washington, DC (US)

(72) Inventors: Yang Liu, Potomac, MD (US); Pan Zheng, Potomac, MD (US); Martin Devenport, Gaithersburg, MD (US); Wei Wu, Washington, DC (US); Xuexiang Du, Washington, DC (US); Mingyue Liu, Washington, DC (US); Fei Tang, Washington, DC (US)

(73) Assignees: OncoC4, Inc., Rockville, MD (US); Children's National Medical Center, Washington, DC (US)

( * ) Notice: Subject to any disclaimer, the term of this patent is extended or adjusted under 35 U.S.C. 154(b) by 537 days.

(21) Appl. No.: 17/677,795

(22) Filed: Feb. 22, 2022

(65) Prior Publication Data
US 2022/0259285 A1 Aug. 18, 2022

Related U.S. Application Data

(63) Continuation of application No. 16/333,888, filed as application No. PCT/US2017/052264 on Sep. 19, 2017, now Pat. No. 11,261,233.

(60) Provisional application No. 62/396,667, filed on Sep. 19, 2016.

(51) Int. Cl.
| | | |
|---|---|---|
| *C07K 14/705* | (2006.01) |
| *A61K 38/17* | (2006.01) |
| *A61K 39/395* | (2006.01) |
| *A61P 35/00* | (2006.01) |
| *A61P 37/06* | (2006.01) |
| *C07K 14/00* | (2006.01) |
| *C07K 16/28* | (2006.01) |
| *A61K 38/00* | (2006.01) |
| *A61K 39/00* | (2006.01) |

(52) U.S. Cl.
CPC .. *C07K 14/70596* (2013.01); *A61K 39/39541* (2013.01); *A61P 35/00* (2018.01); *A61P 37/06* (2018.01); *C07K 14/00* (2013.01); *C07K 16/2818* (2013.01); *C07K 16/2827* (2013.01); *A61K 38/00* (2013.01); *A61K 2039/507* (2013.01); *C07K 2317/24* (2013.01); *C07K 2317/34* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 10,618,960 B2 | 4/2020 | Liu et al. | |
| 11,261,233 B2* | 3/2022 | Liu | A61P 37/06 |
| 2008/0152655 A1 | 6/2008 | Liu et al. | |
| 2009/0252741 A1 | 10/2009 | Liu et al. | |
| 2011/0081354 A1 | 4/2011 | Korman et al. | |
| 2014/0242049 A1 | 8/2014 | Choi et al. | |
| 2015/0051158 A1 | 2/2015 | Akamatsu et al. | |
| 2019/0127468 A1 | 5/2019 | Liu et al. | |
| 2020/0283526 A1 | 9/2020 | Liu et al. | |
| 2021/0047410 A1 | 2/2021 | Liu et al. | |
| 2022/0259286 A1* | 8/2022 | Liu | A61K 39/39541 |

FOREIGN PATENT DOCUMENTS

| | | |
|---|---|---|
| CN | 101255192 A | 9/2008 |
| CN | 101628940 A | 1/2010 |
| CN | 102822198 A | 12/2012 |
| WO | 2006/029219 A2 | 3/2006 |
| WO | 2006/029220 A2 | 3/2006 |
| WO | 2015/104406 A2 | 7/2015 |

OTHER PUBLICATIONS

D Schönfeld et al. An engineered lipocalin specific for CTLA-4 reveals a combining site with structural and conformational features similar, May 2009, Proc Natl Acad Sci USA, vol. 106, No. 20, pp. 8198 to 8203.
Sabel et al (Cancer Immunol. Immunother., 2005, 54:944-952).
Genova et al (Expert Opin. Bio. Ther., 2012, 12:939-948).
English Translation of Office Action for Chinese Application No. 201780057250.0, issued Sep. 21, 2022 (6 Pages).
Office Action for U.S. Appl. No. 16/803,972, issued Jul. 14, 2022 (104 Pages).
Office Action for Canadian Application No. 3,036,997, issued Sep. 20, 2023 (6 Pages).
Office Action for Australian Application No. 2016370648, issued Feb. 10, 2023 (3 Pages).
Notice of Allowance for Chinese Application No. 201680073425.2, issued on Apr. 26, 2022, 05 Pages (02 Pages of Official Copy and 03 Pages of English Translation).
Notice of Allowance for U.S. Appl. No. 16/803,972, issued Nov. 15, 2022 (13 Pages).
Buchbinder, et al., "CTLA-4 and PD-1 Pathways Similarities, Differences, and Implications of Their Inhibition," Am J Clin. Oncol., vol. 39, No. 1, pp. 98-106 (Feb. 3, 2016).
Grosso, et al., "CTLA-4 Blockade in Tumor Models: An Overview of Preclinical and Translational Research," Cancer Immun., vol. 13, No. 5, pp. 1-14 (Jan. 22, 2013).
Lipson, et al., "Successful Administration of Ipilimumab to Two Kidney Transplantation Patients with Metastatic Melanoma," J. Clin. Oncol., vol. 32, No. 19, pp. e69-e71 (2014).

(Continued)

*Primary Examiner* — Ilia I Ouspenski
(74) *Attorney, Agent, or Firm* — POLSINELLI PC; Ron Galant

(57) ABSTRACT

This invention relates to CTLA-4 protein compositions and their use in the mitigation of autoimmune adverse events associated with cancer immunotherapy.

20 Claims, 35 Drawing Sheets

Specification includes a Sequence Listing.

(56) References Cited

OTHER PUBLICATIONS

International Search Report and Written Opinion of PCT/US2017/052264, dated Jan. 23, 2018.

\* cited by examiner

FIG. 1A

MACLGFQRHKAQLNLATRTWPCTLLFLLFIPVFCKAMHVAQPAVVLASSRGIASFVCEYASPGKAT
EVRVTVLRQADSQVTEVCAATYMMGNELTFLDDSICTGTSSGNQVNLTIQGLRAMDTGLYICKVEL
MYPPPYYLGIGNGTQIYVIDPEPCPDSDF<u>LLWILAAVSSGLFFYSFLLTAVSLSKMLKKRSPLTTGVYVK</u>
MPPTEPECEKQFQPYFIPIN

FIG. 1B

MHVAQPAVVLASSRGIASFVCEYASPGKATEVRVTVLRQADSQVTEVCAATYMMGNELTFLDDS
ICTGTSSGNQVNLTIQGLRAMDTGLYICKVELMYPPPYYLGIGNGTQIYVIDPEPCPDSDQEPKSSD
KTHTSPPSPAPELLGGSSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVF
SCSVMHEALHNHYTQKSLSLSPGK

FIG. 5
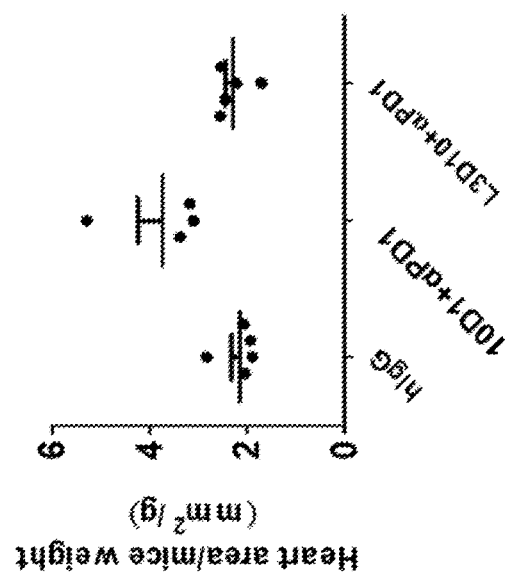
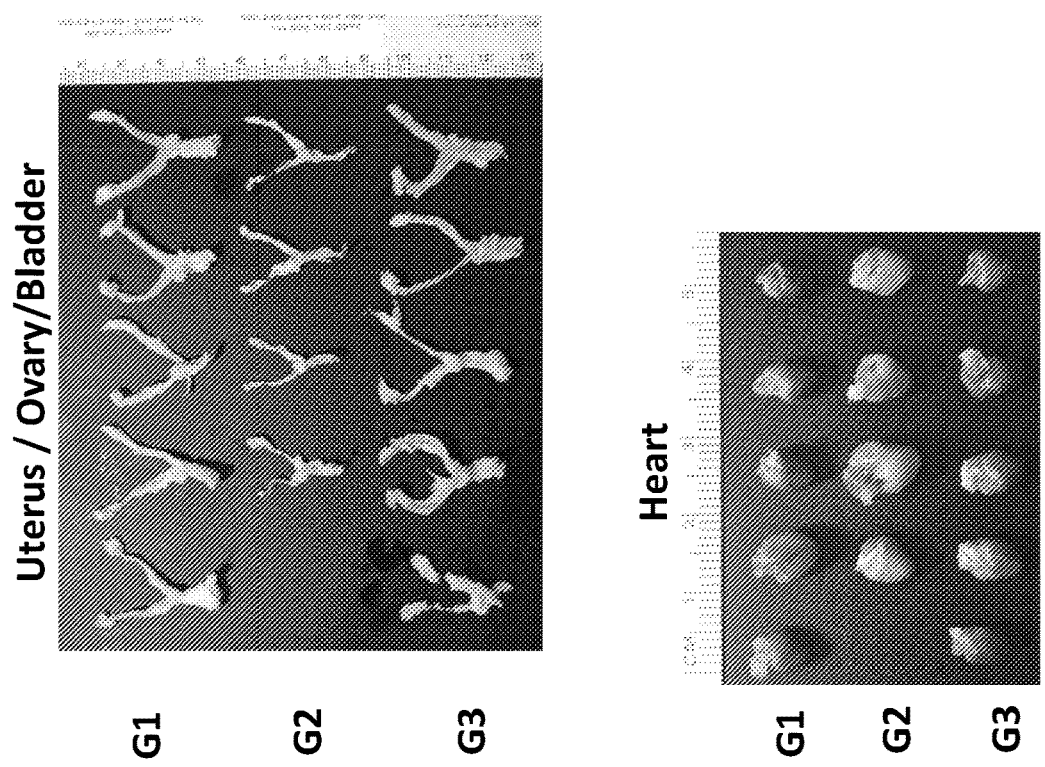

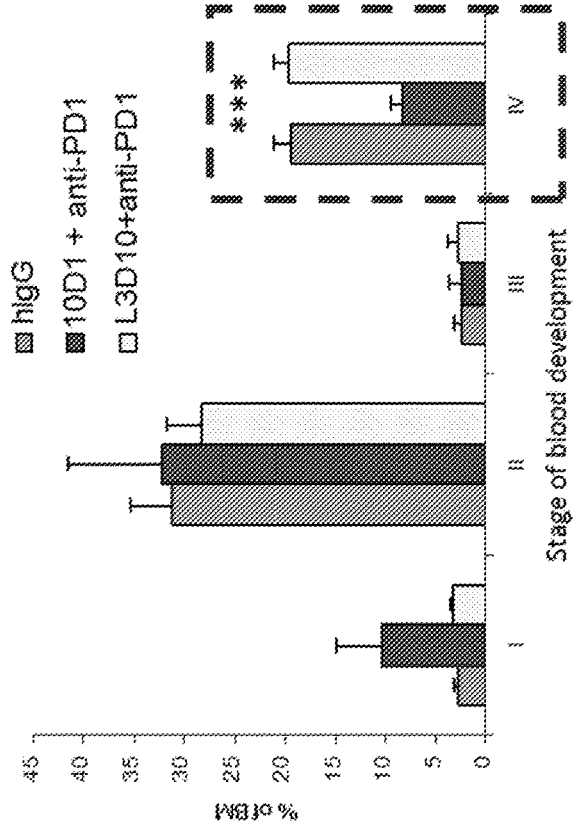
FIG. 6A
FIG. 6B
FIG. 6D
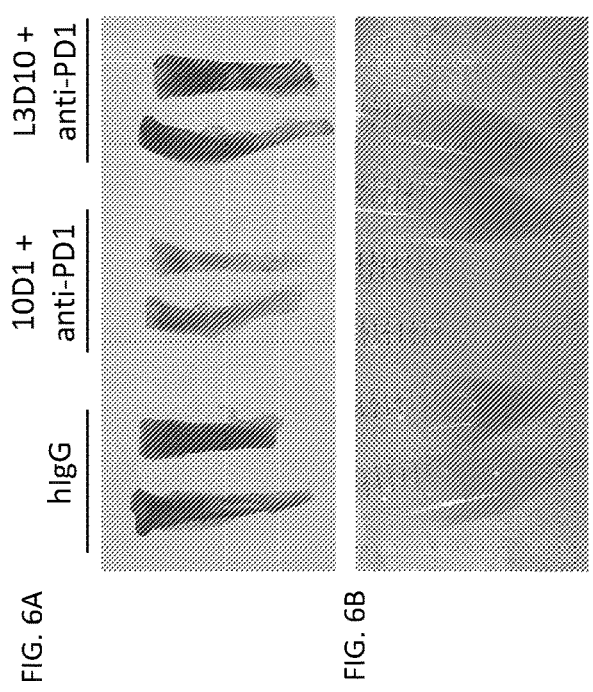
FIG. 6C
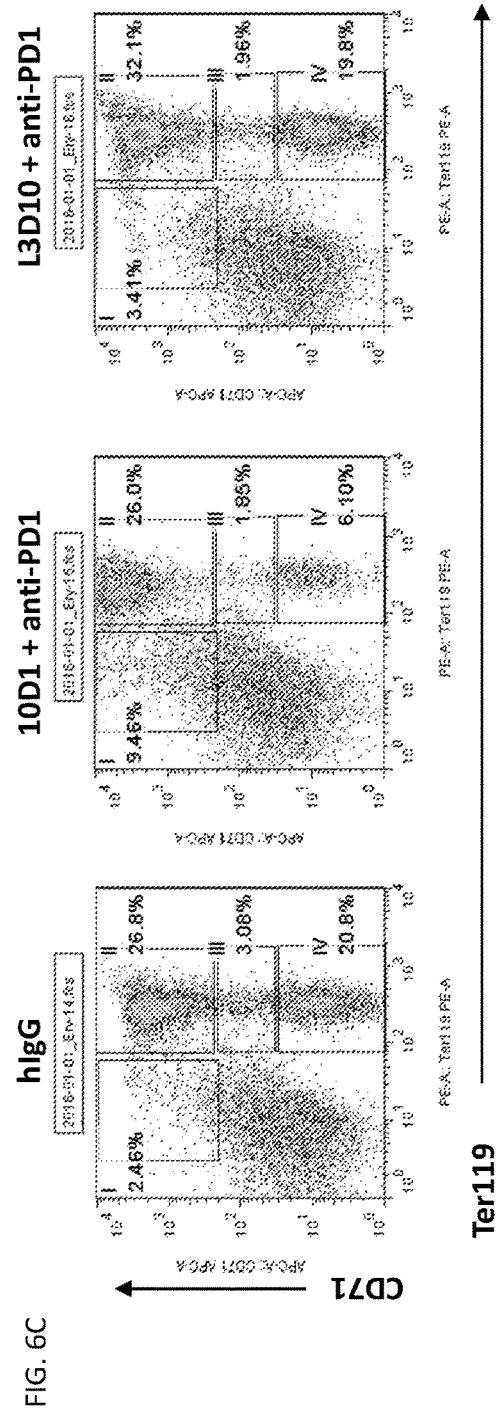

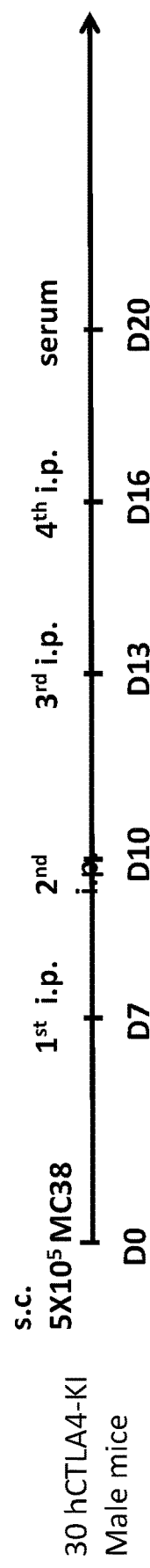
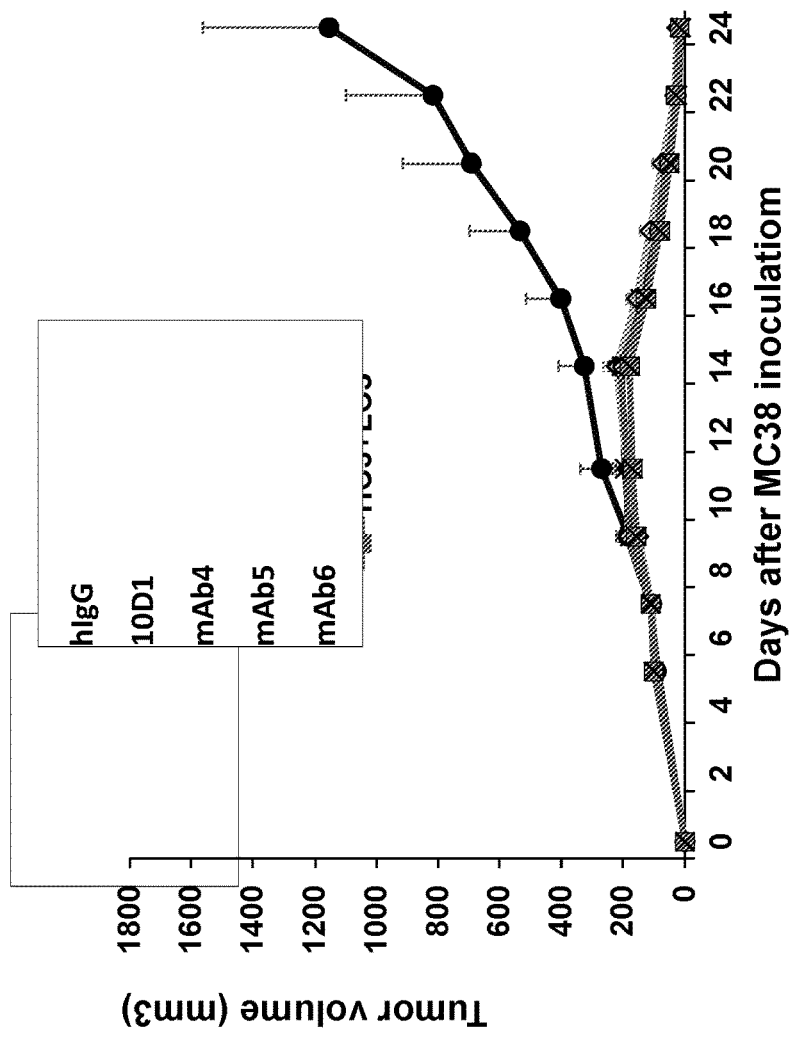
FIG. 11A
FIG. 11B

```
       1.........10........20........30........40........50........60
Hm     MHVAQPAVVLASSRGIASFVCEYASPGKAT EVRVTVLRQADSQVTEVCAATYMGNELTF
Mk     ---------------------n----------------------------------------
Ms     iq-t--s------h-v---p-----shn-d-------tnd-m------t-ftek-tvg-
Mut         M1            M2          M3              M4       M6  M5

........70........80........90........100.......110.......120
Hm     LDDSICTGTSSGNQVNLTIQGLRAMDTGLYICKVELMYPPPYYLGIGNGTQIYVIDPEPC
Mk     ------------------------------------m-----------------------
Ms     --ypf-s--fnesr----------v-----l----fv-m---------------------
Mut      M7       M8           M9     M10              M11

...124
Hm     PDSD
Mk     ----
Ms     ----
```

FIG. 15

CTLA-4Fc WT

MHVAQPAVVLASSRGIASFVCEYASPGKATEVRVTVLRQADSQVTEVCAATYMGNELTFLDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M1 iqvtqPsVVLASSRGIASFVCEYASPGKATEVRVTVLRQADSQVTEVCAATYMGNELTFLDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M2

MHVAQPAVVLASShgLASFpCEYASPGKATEVRVTVLRQADSQVTEVCAATYMGNELTFLDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYR

CTLA-4Fc M6

MHVAQPAVVLASSRGIASFVCEYASPGKATEVRVTVLRQADSQVTEVCAAtTYMGNELTFLDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M7

MHVAQPAVVLASSRGIASFVCEYASPGKATEVRVTVLRQADSQVTEVCAATYMGNELTFLDypfcsGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M8

MHVAQPAVVLASSRGIASFVCEYASPGKATEVRVTVLRQADSQVTEVCAATYMGNELTFLDDSICTGTfnesrVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK CTLA-4Fc M9

MHVAQPAVVLASSRGIASFVCEYASPGKATEVRVTVLRQADSQVTEVCAATYMGNELTFLDDSICTGTSSGNQVNLTIQGLRAMvDTGLYICKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M10

MHVAQPAVVLASSRGIASFVCEYASPGKATEVRVTVLRQADSQVTEVCAATYMGNELTFLDDSICTGTSSGNQVNLTIQGLRAMMDTGLYlCKVELMYPPPYYLGIGNGTQIYVIDPEPCP
DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

CTLA-4Fc M11

MHVAQPAVVLASSRGIASFVCEYASPGKATEVRVTVLRQADSQVTEVCAATYMGNELTFLDDSICTGTSSGNQVNLTIQGLRAMDTGLYICKVELMYPPPYfvGmGNGTQIYVIDPEPCPD
SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

FIG. 16B

CTLA-4Fc M12
iqvtqPsVVLASSRGIASFVCEYASPGKATEVRVTVLRQADSQVTEVCAATftekntvgFLDDSICTGTfnesrVNLTIQGLRAMDTGLYICKVELMYPPPYfvGmGNGTQIYVIDPEPCPD SDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSP GK CTLA-4Fc M13
MHVAQPAVVLASSRGIASFVCEYASPGKyTEVRVTVLRQADSQVTEVCAATYMMGNELTFLDDSICTGTSSGNQVNLTIQGLRAMDTGLYICKVELMYPPPYfvGmGNGTQIYVI DPEPCPDSDQEPKKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQ KSLSLSPGK CTLA-4Fc M14
iqvtqPsVVLASSRGIASFVCEYASPGKATEVRVTVLRQADSQVTEVCAATfteknтvgFLDDSICTGTSSGNQVNLTIQGLRAMDTGLYICKVELMYPPPYfvGmGNGTQIYVIDPEPCP DSDQEPKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSP GK CTLA-4Fc M15 (belatacept)
MHVAQPAVVLASSRGIASFVCEYASPGKyTEVRVTVLRQADSQVTEVCAATfteknтvgFLDDSICTGTSSGNQVNLTIQGLRAMDTGLYICKVELMYPPPYeGIGNGTQIYVID PEPCPDSDQEPKKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQK SLSLSPGK CTLA-4Fc M16
iqvtqPsVVLASSRGIASFVCEYASPGKATEVRVTVLRQADSQVTEVCAATfteknтvgFLDDSICTGTfnesrVNLTIQGLRAMDTGLYICKVELMYPPPYfvGmGNGTQIYVIDPEPCPD SDQEPKSSDKTHTSPPSPAPELLGGSSVFLFPPKPKDTLyltRePEVTCVVVDVSHEDPEVKFNWYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG K CTLA-4Fc M17
MHVAQPAVVLASSRGIASFVCEYASPGKyTEVRVTVLRQADSQVTEVCAATYMMGNELTFLDDSICTGTSSGNQVNLTIQGLRAMDTGLYICKVELMYPPPYfeGmGNGTQIYVI DPEPCPDSDQEPKKSSDKTHTSPPSPAPELLGGSSVFLFPPKPKDTLMISRTPEVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQ KSLSLSPGK

FIG. 19

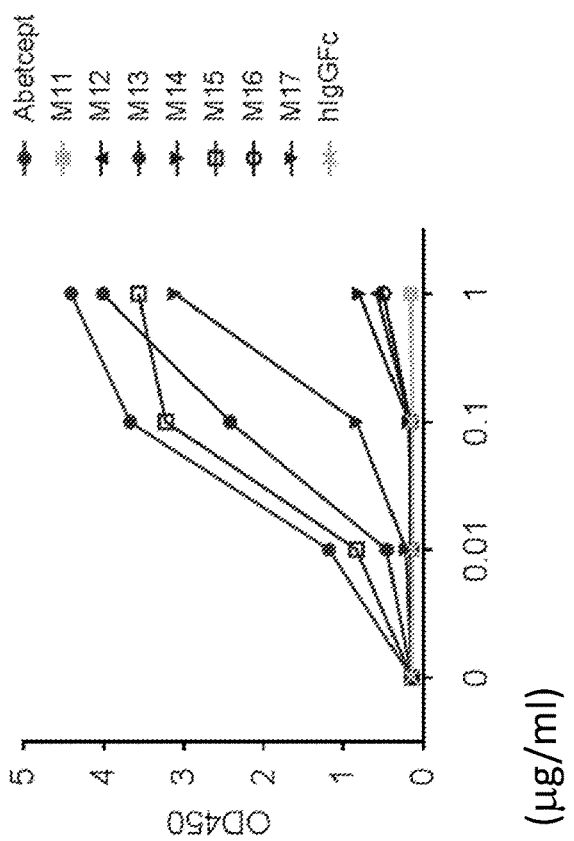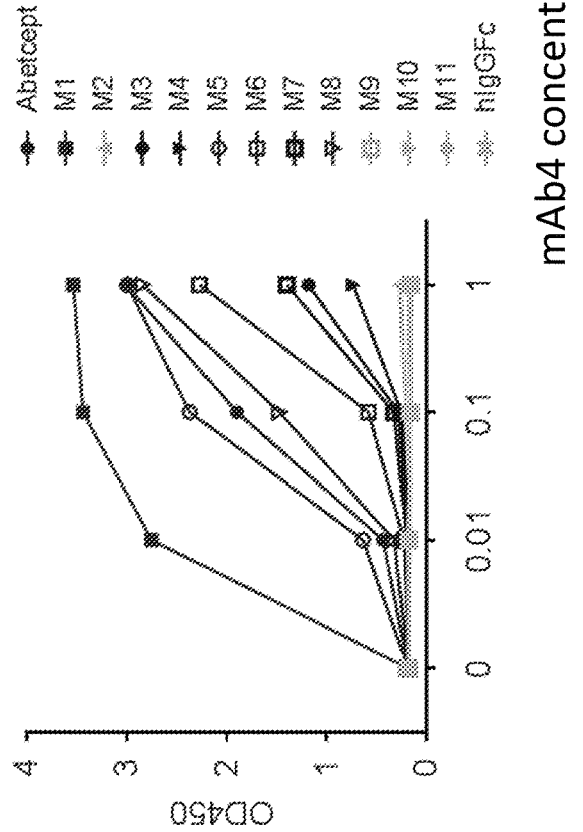
FIG. 23A
FIG. 23B
mAb4 concentration (μg/ml)

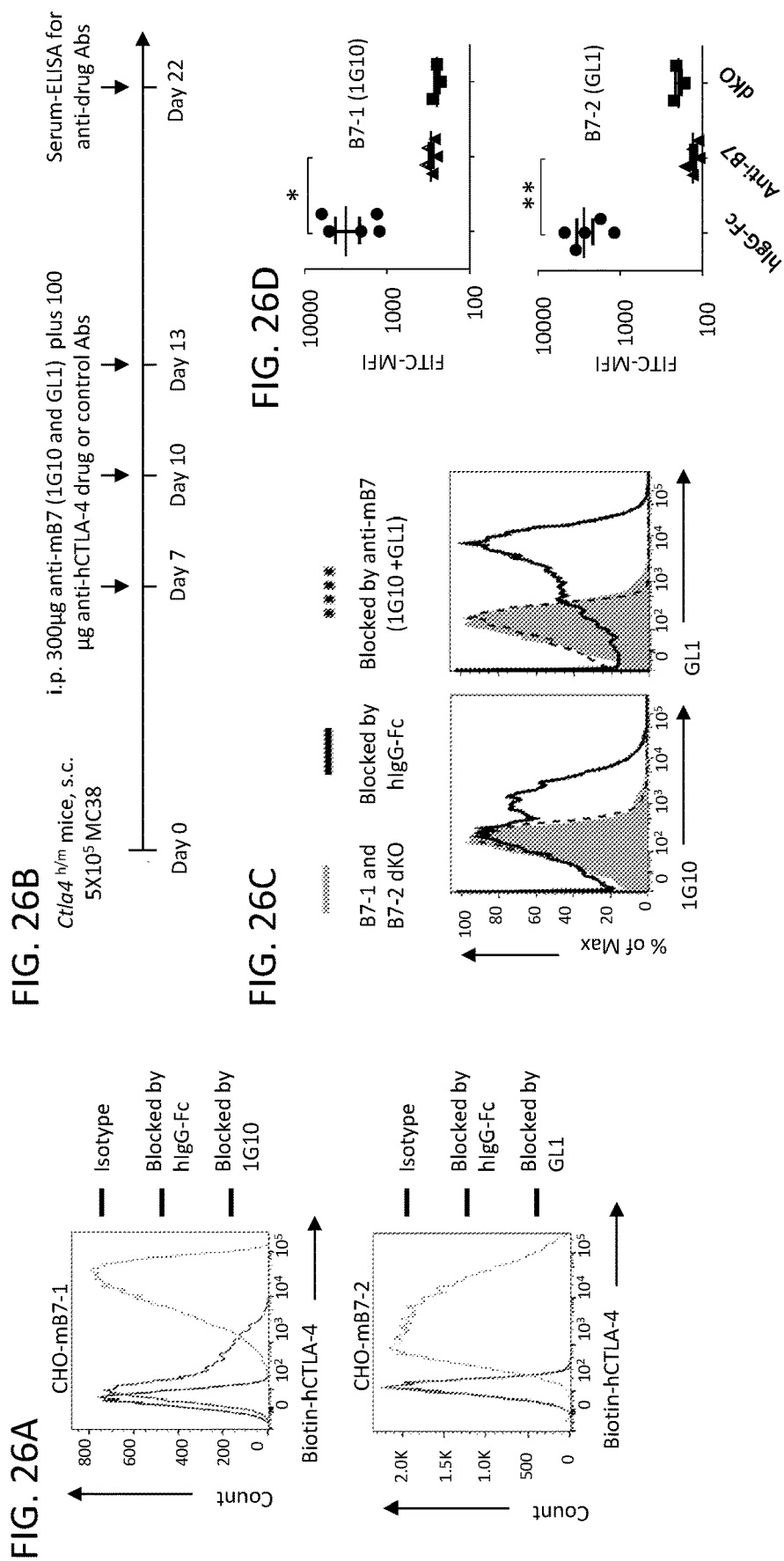

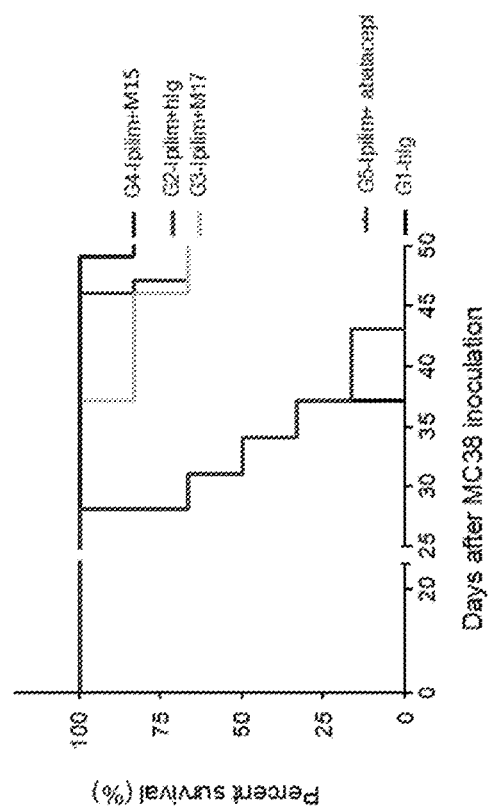
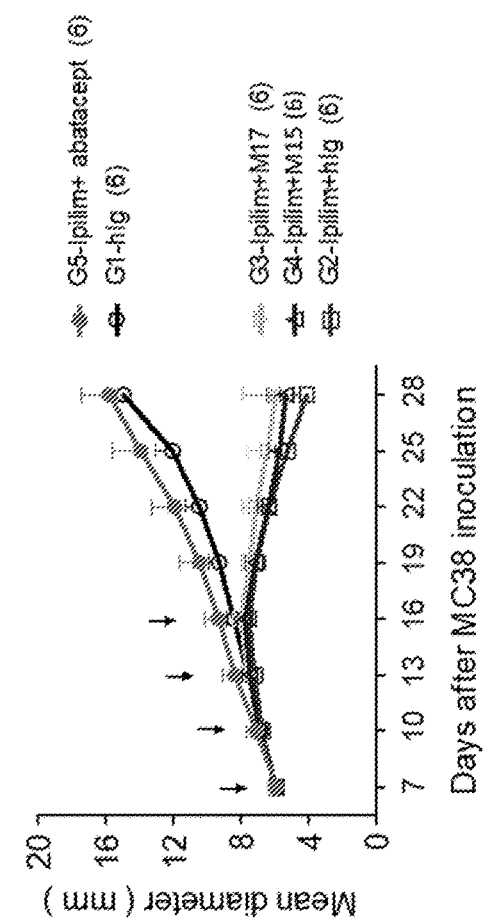
FIG. 28B
FIG. 28A

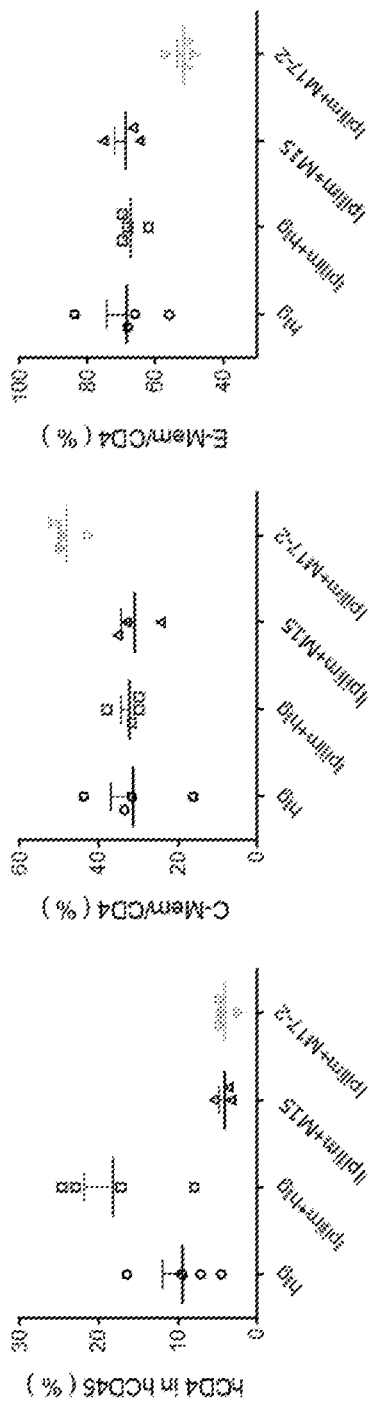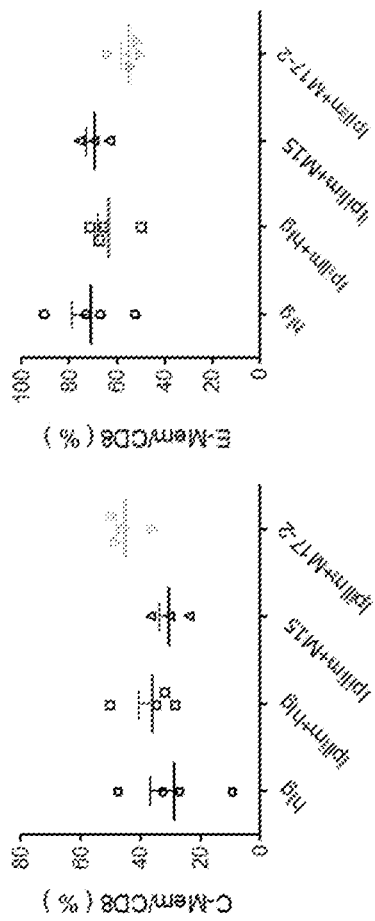

CD80 AND CD86 BINDING PROTEIN COMPOSITIONS AND USES THEREOF

BACKGROUND OF THE INVENTION

Treatment with anti-CTLA-4 antibodies has been shown to be a powerful tool for enhancing anti-tumor immunity in preclinical models (10). Monotherapy with an antibody against CTLA-4 promoted rejection of transplantable tumors of various origins. Based on promising preclinical tumor model studies, the clinical potential of antibodies against CTLA-4 has been explored in different human malignancies. Although anti-CTLA-4 (Ipilimumab, marketed as Yervoy, disclosed in U.S. Pat. No. 6,984,720) has demonstrated efficacy in treating melanoma, treatment and targeting of CTLA-4 is associated with autoimmune-like toxicities. In addition, anti-CTLA-4 mAbs such as Ipilimumab and Tremelimumab are used in combination therapy with anti-PD-1/PD-L1 antibodies with superior therapeutic effect. However, the improved therapeutic effect is associated even higher rates of grade 3 and grade 4 organ toxicity. Characteristic side effects from inhibition of CTLA-4 are generally called immune-related adverse events (irAEs) and the most common irAEs are skin rash, hepatitis, colitis and endocrinopathies, particularly hypopituitarism. Therefore, there is a large unmet medical need to treat irAE while preserving the cancer therapeutic effect of anti-CTLA-4 monoclonal antibody (mAb).

The inventors have demonstrated that both clinically proven therapeutic anti-human CTLA-4 mAb and two anti-mouse Ctla-4 mAbs induce tumor rejection without blocking B7-CTLA-4 interactions under physiologically relevant conditions. Therefore, such blockade was not necessary for tumor rejection even for the mAb that can potently block B7-CTLA-4 interactions. These data refute the hypothesis that anti-CTLA-4 mAb confers an immunotherapeutic effect through checkpoint blockade (108). In support of this notion, it has further been shown that the immunotherapeutic effect mediated by Ipilimumab and possibly other anti-CTLA-4 mAbs, was unaffected by blocking 137-1 and 137-2, which is critical for pathogenesis of autoimmune diseases.

Accumulating data demonstrated that the human CTLA-4 gene encodes two different isoforms of proteins through alternative splicing: one with a trans-membrane domain which is thus likely to be anchored in membrane, and another that lacks the trans-membrane domain and is predicted to be secreted (sCTLA-4)(128). Importantly, genetic studies demonstrated that a polymorphism of CTLA-4 that reduces the relative abundance of the soluble isoform strongly associates with multiple autoimmune diseases (64). The fact that subjects with autoimmune prone alleles express less sCTLA-4 mRNA suggests that sCTLA-4 may be protective. This is notion is supported by the broad therapeutic effect of abatacept (129,130), which is a form of soluble CTLA-4, and by a genetic study in which the selective ablation of the sCTLA-4 isoform accelerated the development of type I diabetes in the mice (131). Based on these genetic data, the inventors had the insight that an anti-CTLA-4 antibody that shows the poorest binding to soluble CTLA-4 should give the least irAE. Indeed, based on the impact of the antibodies on the body weight gain in mice treated with anti-CTLA-4 antibodies during the perinatal period, a strong correlation was found among four anti-CTLA-4 mAbs: Ipilimumab has the strongest binding for sCTLA-4 and is the most toxic anti-CTLA-4, whereas antibody L3D10 had the weaker binding to sCTLA-4 and was the least toxic. Furthermore, humanized L3D10 variants that preferentially reduced binding to sCTLA-4 showed further improved the safety profile over the parent antibody.

The protective function of soluble CTLA-4 molecules further support an approach of using soluble CTLA-4 fusion proteins to mitigate, reduce or treat irAE. However, since patients with anti-CTLA-4 mAb induced irAE have circulating anti-CTLA-4 mAbs, CTLA-4 fusion proteins such as abatacept will not only reduce the therapeutic effect of anti-CTLA-4 mAbs by preventing them from binding to cell-associated CTLA-4 molecules, but also be rendered ineffective because they will be cleared from circulation after forming immune-complex with circulating anti-CTLA-4 mAbs. Accordingly, there is a need in the art for improved CTLA-4 immunotherapy compositions and methods.

SUMMARY OF THE INVENTION

This invention relates to human CTLA-4 proteins and anti-B7-1 and anti-B7-2 compositions, and their use for immunotherapy and the treatment of autoimmune disease and inflammation, and for the reduction of autoimmune side effects associated with anti-CTLA-4 immunotherapy. Specifically, the invention relates to a CTLA-4 protein that exhibits reduced or eliminated binding to anti-CTLA-4 antibodies used in cancer immunotherapy but retains the ability to bind to B7-1 and B7-2.

The CTLA-4 protein may comprise a CTLA-4 protein in which the amino acids of an anti-CTLA-4 antibody binding epitope are modified or mutated in order to reduce or abolish binding of an anti-CTLA-4 antibody to the CTLA-4 protein, as compared to a wild-type extracellular domain of CTLA-4. The CTLA-4 protein may have anti-cancer immunotherapeutic activity. The anti-CTLA-4 antibody may be Ipilimumab. The CTLA-4 protein may retain its ability to bind at least one of B7-1 and B7-2. The CTLA-4 protein may not block the anti-cancer immunotherapeutic effects of the anti-CTLA-4 antibody.

The CTLA-4 protein may comprise an extracellular domain of mature human CTLA-4, a variant thereof, or an active fragment thereof. The CTLA-4 protein may comprise an amino acid sequence selected from the group consisting of SEQ ID NOS: 34, 36, 38, 39, 40, and 46-48, a variant thereof, and an active fragment thereof. The CTLA-4 protein may be soluble. The CTLA-4 protein may comprise a CTLA-4 fusion protein wherein the extracellular domain of human CTLA-4 is attached to a human immunoglobulin heavy chain constant region. The CTLA-4 protein may comprise an amino acid sequence selected from the group consisting of SEQ ID NO: 17, 19, 21, 22, 23, and 42-44. The CTLA-4 protein may be belatacept.

In another embodiment, the invention relates to antibody compositions that bind at least one of human B7-1 and B7-2, and their use for immunotherapy and the treatment of autoimmune disease and inflammation, and for the reduction of autoimmune side effects associated with anti-CTLA-4 immunotherapy.

Also provided herein is a pharmaceutical composition comprising a therapeutically effective amount of a protein or antibody described herein. The pharmaceutical composition may comprise a physiologically acceptable carrier or excipient.

In another aspect, provided herein are methods for reducing one or more immune functions or responses in a subject, comprising administering to a subject in need thereof the CTLA-4 protein or anti-B7 antibody composition, or a pharmaceutical composition thereof. In a specific embodiment, presented herein are methods for preventing, treating, or managing a disease in which it is desirable to inhibit or reduce one or more immune functions or responses. The disease may be an autoimmune disease, such as rheumatoid arthritis (RA) or Juvenile Idiopathic Arthritis (JIA).

The compositions described herein may also be used to mitigate, minimize or treat the immune related adverse effects associated with immunotherapy. In particular, the composition may comprise a molecule that blocks or reduces the function of B7-1 and B7-2 without affecting the cancer immunotherapeutic activity of an anti-CTLA-4 antibody. The molecule may be a CTLA-4 protein, an anti-B7 antibody, or a pharmaceutical composition thereof. The molecule may be an antibody that can functionally block binding of at least one of B7-1 and B7-2 to at least one of CD28 and CTLA-4, and may be anti-B7-1 or anti-B7-2. The antibody may be capable of binding both B7-1 and B7-2, and may comprise a binding site that reacts with both 87-1 and 137-2.

A composition described herein may be administered to a subject, who may have cancer, in combination with, or on a background of, anti-CTLA-4 immunotherapy. The composition may be used prophylactically to prevent irAEs before anti-CTLA-4 treatment is initiated or the before the clinical signs of irAEs emerge. In another embodiment, the composition is used therapeutically to treat irAEs after anti-CTLA-4 treatment is initiated and the clinical symptoms are diagnosed.

BRIEF DESCRIPTION OF THE DRAWINGS

FIGS. 1A-B. Human CTLA-4 sequence. FIG. 1A shows the sequence of human CTLA-4 protein (NCBI accession number NP 005205; SEQ ID NO: 1) with the signal peptide in bold, the IgV domain underlined and the transmembrane domain double underlined. FIG. 1B shows the sequence of abatacept (SEQ ID NO: 2) with the CTLA-4 sequence shown in bold with the remainder of the protein comprising the IgG1 Fc region.

FIG. 5. Pathological effects of chimeric L3D10 and 10D1 in combination with anti-PD-1. Group 1 is hIgG, Group 2 is 10D1+anti-PD1, and Group 3 is L3D10+anti-PD1. To further examine to relative toxicity of L3D10 compared to 10D1 when administered in combination with anti-PD-1, the gross anatomy of the mice described in FIG. 4 above was investigated. The Uterus/Ovary/Bladder and thymus were noticeably smaller in mice treated with 10D1+PD-1, whereas the organs in mice treated with L3D10+anti-PD-1 was comparable to hIgG control. In contrast, the hearts dissected from mice treated with 10D1 appeared larger in size with a noticeably whiter appearance.

FIGS. 6A-D. Treatment with 10D1 in combination with anti-PD-1 results in abnormal erythropoiesis. Given the differences in the hearts observed in FIG. 5, erythropoiesis was investigated within the mice and clear differences were observed in the mice treated with 10D1+anti-PD-1 relative to the groups treated with L3D10+anti-PD-1 or control antibody (hIgG), which were fairly similar. The bone marrow from mice treated with 10D1+anti-PD-1 had a noticeably whiter color (FIG. 6A) and the isolated blood was almost completely white in color (FIG. 6B). In accordance with this, when differentiation of the red blood cells was analyzed using distribution of CD119 and CD71 markers, a statistically significant reduction in the number of cells undergoing Stage IV development was observed in the 10D1+anti-PD-1 treated mice. Representative FACS profiles are shown in FIG. 6C, while summary data are presented in FIG. 6D.

FIGS. 11A-B. Anti-tumor activity of humanized L3D10 antibodies compared to 10D1. Using the MC38 mouse tumor model in human CTLA-4 knockin mice, the anti-tumor activity of humanized L3D10 antibodies was investigated compared to the chimeric L3D10 antibody and 10D. FIG. 11A shows the treatment schedule of the in vivo experiment. Mice were given a total of 4 doses of antibody every 3 days starting on day 7 after inoculation. All humanized antibodies (n=6 per group) completely eradicated the tumors and were comparable to 10D1 (FIG. 11B).

The p-values for comparisons between various treatments are as follows.

| | |
|---|---|
| hIg vs. αPD1 + L3D10 | P value = 0.16 |
| hIg vs. αPD1 + hIg | P value = 0.0384* |
| hIg vs. αPD1 + 10D1 | P value = <2e-16*** |
| hIg vs. αPD1 + mAb4 | P value = 0.16 |
| hIg vs. αPD1 + mAb5 | P value = 0.00207** |
| αPD1 + L3D10 vs. αPD1 + hIg | P value = 0.00654** |
| αPD1 + L3D10 vs. αPD1 + 10D1 | P value = <2e-16*** |
| αPD1 + L3D10 vs. αPD1 + mAb4 | P value = 0.492 |
| αPD1 + L3D10 vs. αPD1 + mAb5 | P value = 0.000124*** |
| αPD1 + hIg vs. αPD1 + 10D1 | P value = <2e-16*** |
| αPD1 + hIg vs. αPD1 + mAb4 | P value = 0.0579 |
| αPD1 + hIg vs. αPD1 + mAb5 | P value = 0.409 |
| αPD1 + 10D1 vs. αPD1 + mAb4 | P value = <2e-16*** |
| αPD1 + 10D1 vs. αPD1 + mAb5 | P value = <2e-16*** |
| αPD1 + mAb4 vs. αPD1 + mAb5 | P value = 0.000446*** |

Figure 13:
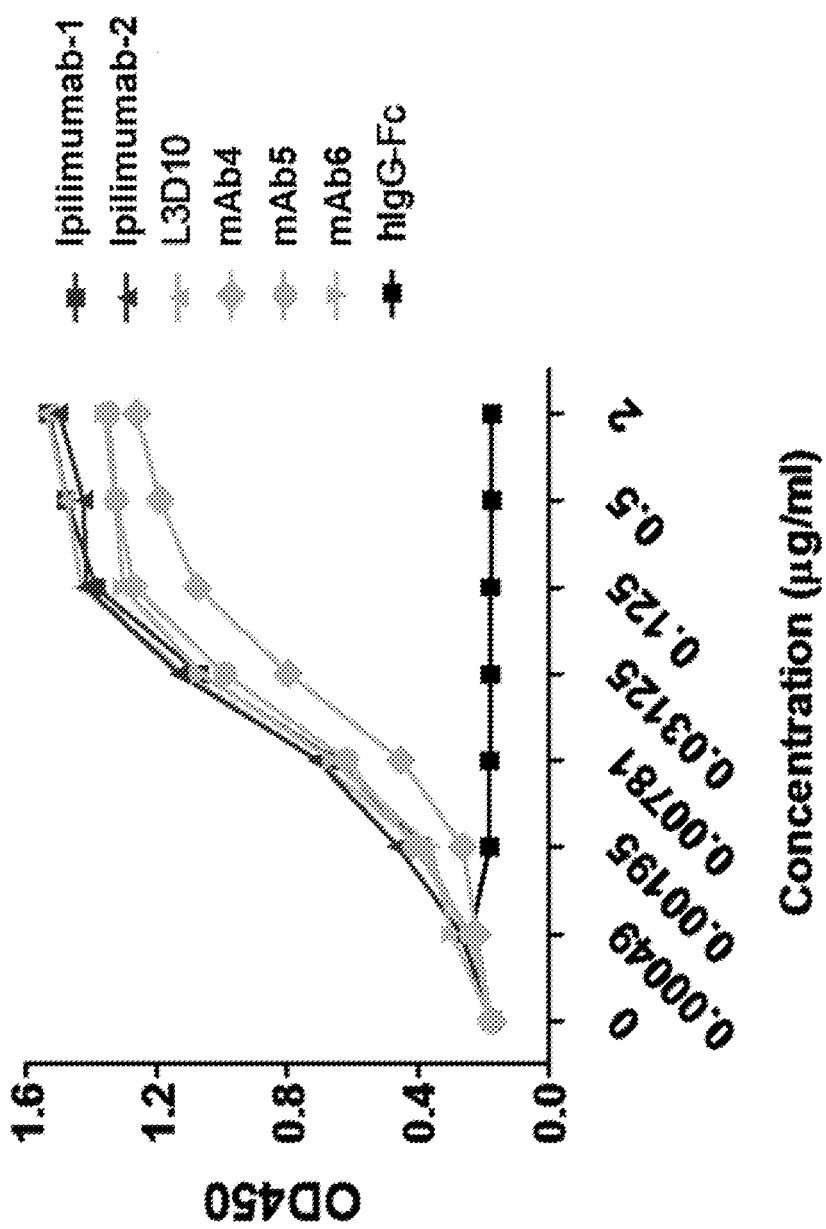

FIG. 13. Humanization of L3D10 does not affect binding to immobilized CTLA-4. The capacity of the humanized L3D10 antibodies to bind immobilized CTLA-4 was determined as described in FIG. 23. X-axis indicates the concentration of anti-CTLA-4 mAbs added into solution. Humanization does not affect binding to immobilized CTLA-4 and all three humanized antibodies demonstrated similar binding to the parental chimeric L3D10 antibody and 10D1. Similar patterns were observed when CTLA-4-Ig was used instead of CTLA-4-his.

Figure 14:
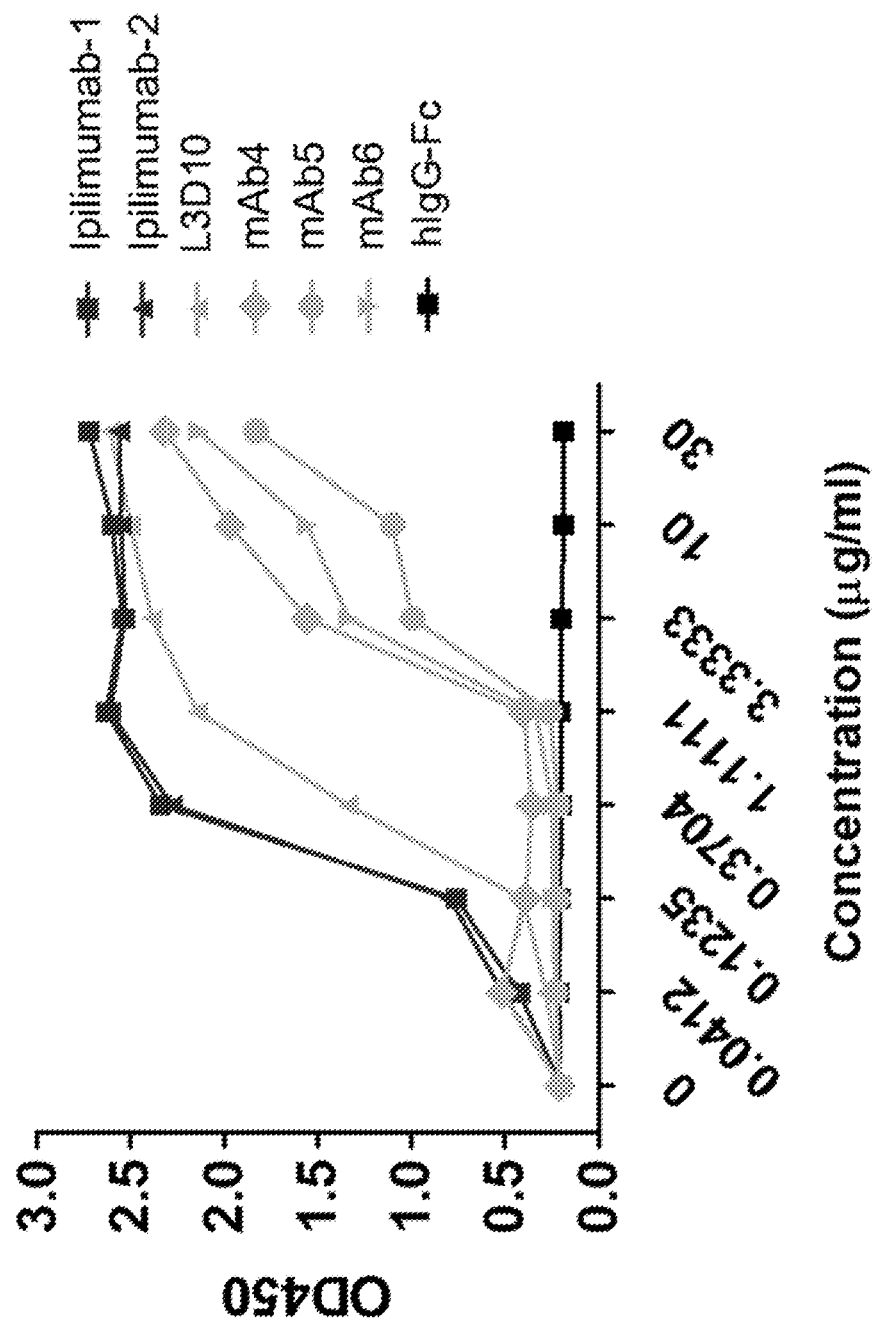
Figure 17A:
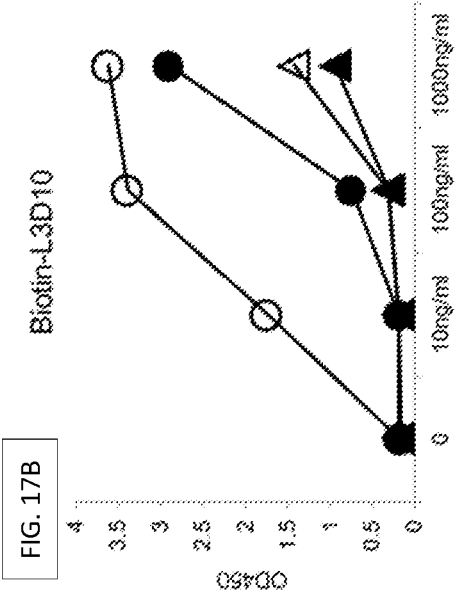
Figure 17B:
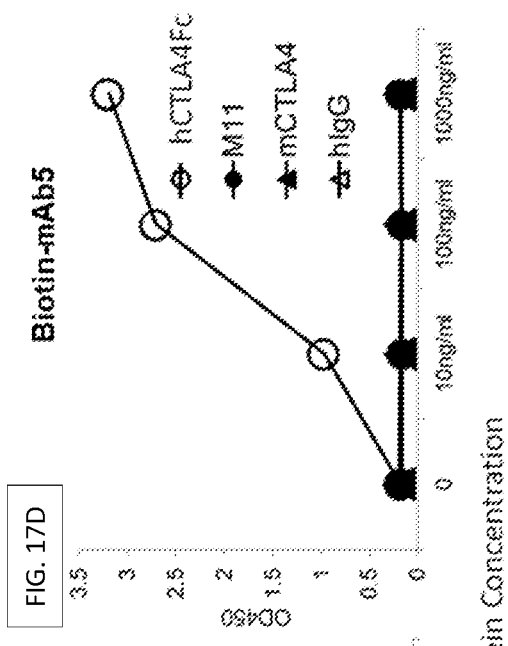
Figure 17C:
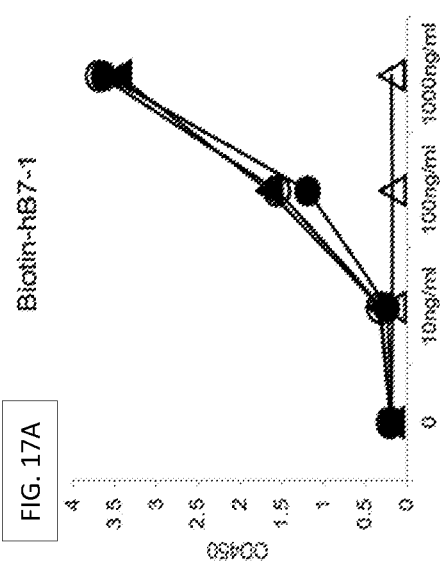
Figure 17D:
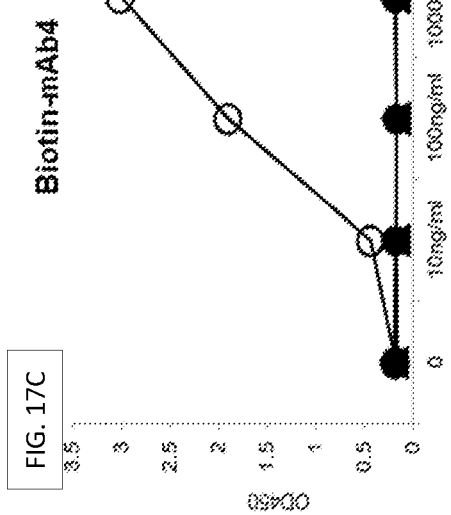

FIG. 14. Humanization further reduces L3D10 binding to soluble CTLA-4. The capacity of the humanized L3D10 antibodies to bind soluble CTLA-4 was determined as described in FIG. 23. X-axis indicates the concentration of anti-CTLA-4 mAbs coated onto ELISA plates. Humanization further reduces binding to soluble CTLA-4 relative to the parental L3D10 chimeric antibody. Similar patterns were observed when CTLA-4-Ig was used instead of CTLA-4-his.

FIG. 15. Alignment of the human, macaque and mouse CTLA-4 extracellular domains. The amino acid sequences of the human (Hm; amino acids 1-124 of SEQ ID NO: 2), macaque (Mk) and mouse (Ms) CTLA-4 protein extracellular domains are aligned and the conserved amino acids (relative to the human sequence) are shown with dashes (-).

In order to help the alignment, the mouse sequence has a deletion and insertion (relative to the human and monkey sequences) at the positions highlighted. The known B7-1 Ig binding site is shown in bold and underlined. The sequences demonstrate that the human and monkey sequences are highly conserved, whereas the mouse sequence has a number of amino acid differences. Based on this sequence alignment, 11 mutant (M1-M11) human CTLA-4Fc proteins were designed that incorporate murine specific amino acids—the amino acids incorporated into each mutant protein are shown in blue.

FIGS. 16A and B. Amino acid sequence composition of the WT (SEQ ID NO: 2) and mutant CTLA-4Fc proteins (SEQ ID NOs: 7-17). DNA constructs encoding the WT CTLA-4Fc protein and 11 mutant proteins, M1-M11, incorporating murine Ctla-4 amino acids were designed as shown. The amino acid sequences are for mature proteins, including the IgG1 Fc portion, but not the signal peptide. The known 137-1Ig binding site is shown in large letters and double-underlined. The replaced murine amino acid residues in the mutant are shown lower case. The IgG1 Fe portion of the proteins in underlined.

FIGS. 17A-D. Mutation in M11 (AA 103-106. YLG1>fcGm) selectively abolish antibody binding to human CTLA-4. Data shown are means of duplicates, depicting the binding of B7-1Fc (FIG. 17A), L3D10 (FIG. 17B), mAb4 (FIG. 17C), and mAb5 (FIG. 17D) binding to plate-coated hCTLA-4-Fc (open circles), mCTLA-4-Fc (filled triangles), M11 (filled circles) and IgG1-Fc (open triangles).

Figure 18:
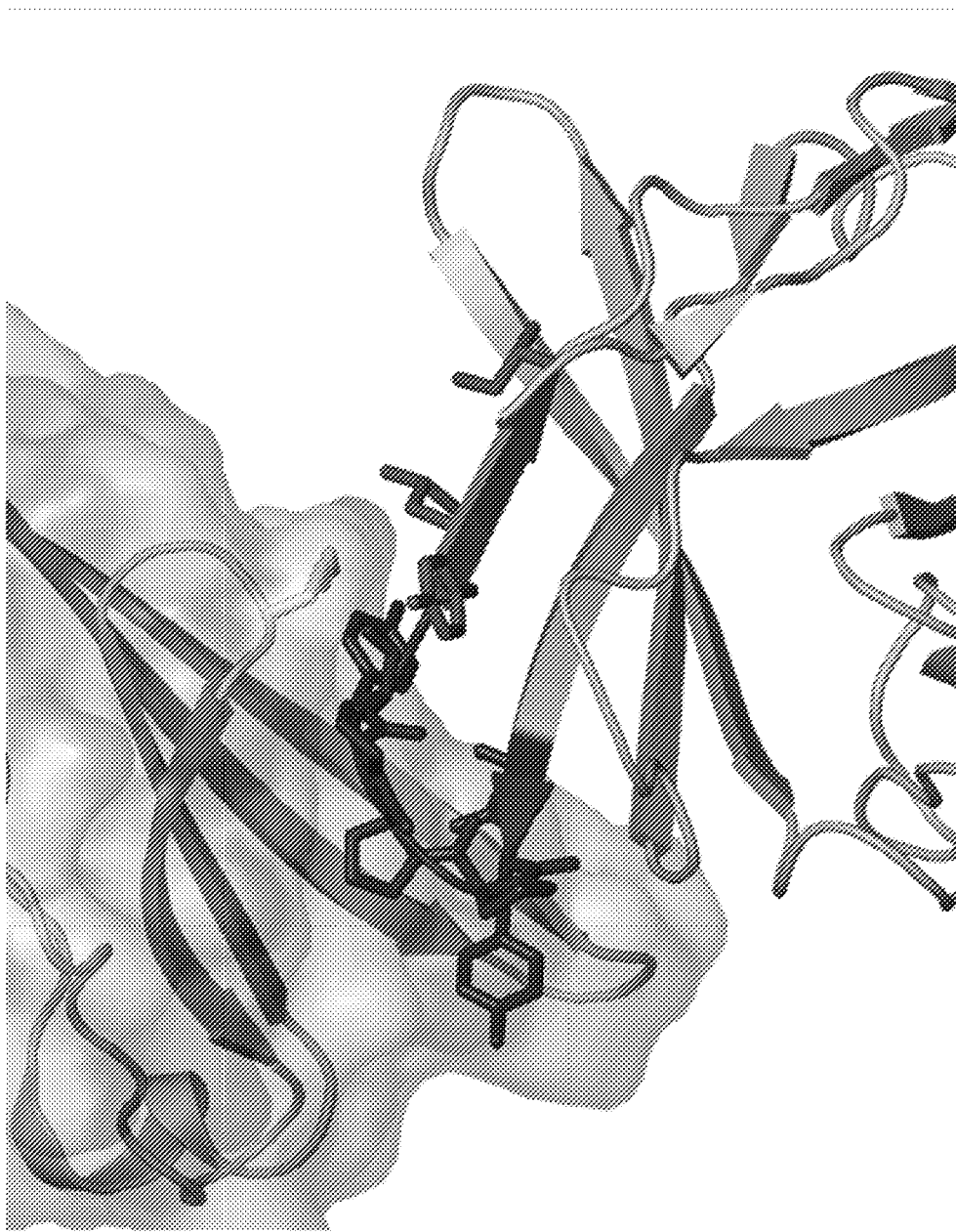

FIG. 18. Mapping L3D10, mAb4 and mAb5 to an epitope adjacent to the B7-1 binding site in a 3-D structure of the B7-1-CTLA-4 complex. The B7-1 binding motif and antibody epitope are shaded differently. B7-1 is depicted above CTLA-4 with a space-filled ribbon, while that of CTLA-4 is depicted as an unfilled ribbon.

FIG. 19. Amino acid sequence composition of the mutant CTLA-4Fc proteins, M12-M17 (SEQ ID NOs: 18-23). DNA constructs encoding the 6 mutant CTLA-4Fc proteins, M12-M17, incorporating murine Ctla-4 amino acids were designed as shown. The amino acid sequences are for mature proteins, including the IgG1 Fc portion, but not the signal peptide. The known B7-1Ig binding site is shown in large letters and double-underlined. The replaced murine amino acid residues in the mutant are shown lower case. The IgG1 Fe portion of the proteins is underlined.

Figure 20A:
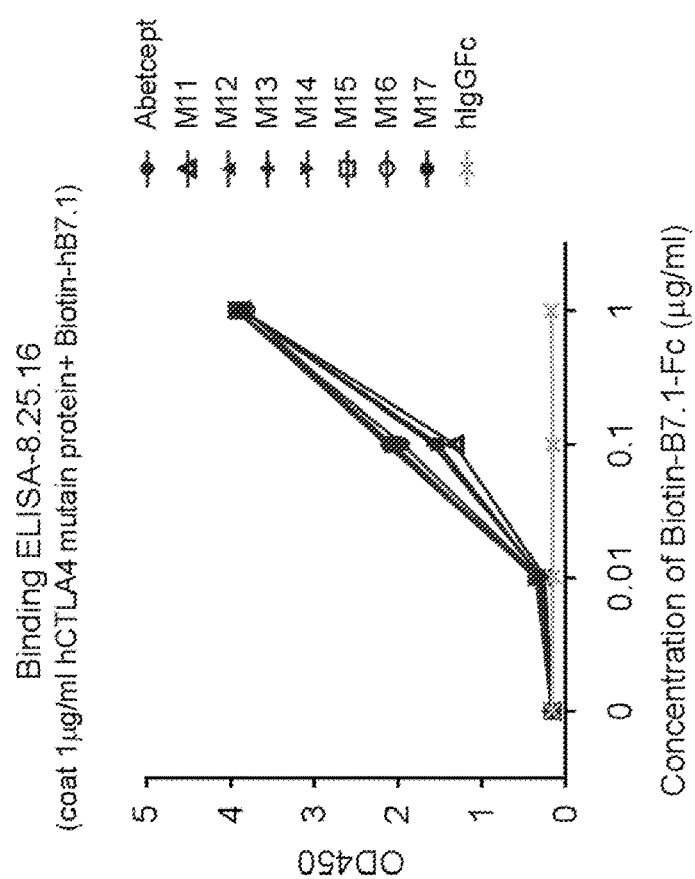
Figure 20B:
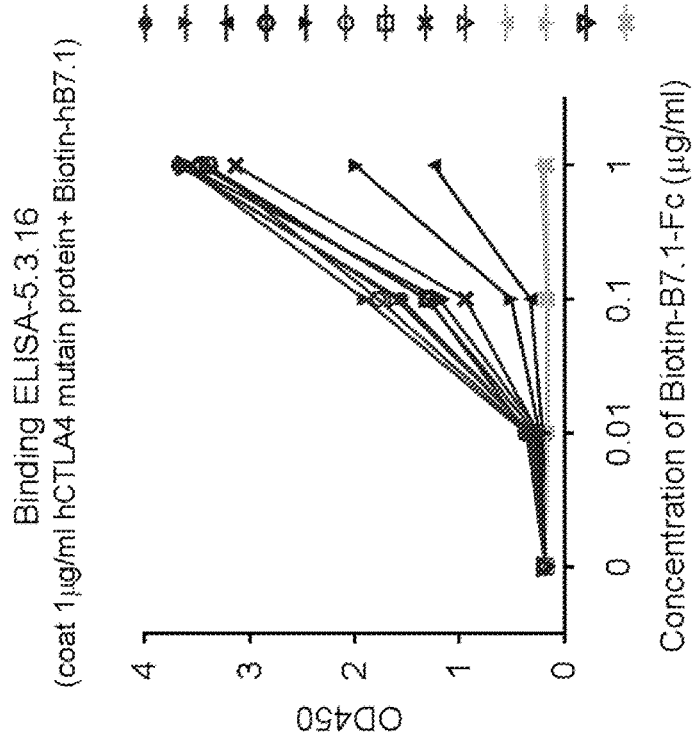

FIGS. 20A and B. Identifying CTLA-4Fc mutant proteins that retain binding to biotinylated 87-1Fc. CTLA4-Fc fusion proteins M1-M17 were coated onto 96-well plates. Biotinylated B7-1Fc at the given concentration was incubated with the plates and detected with streptavidin-conjugated HRP. Data shown are means of duplicate experiments.

Figure 21A:
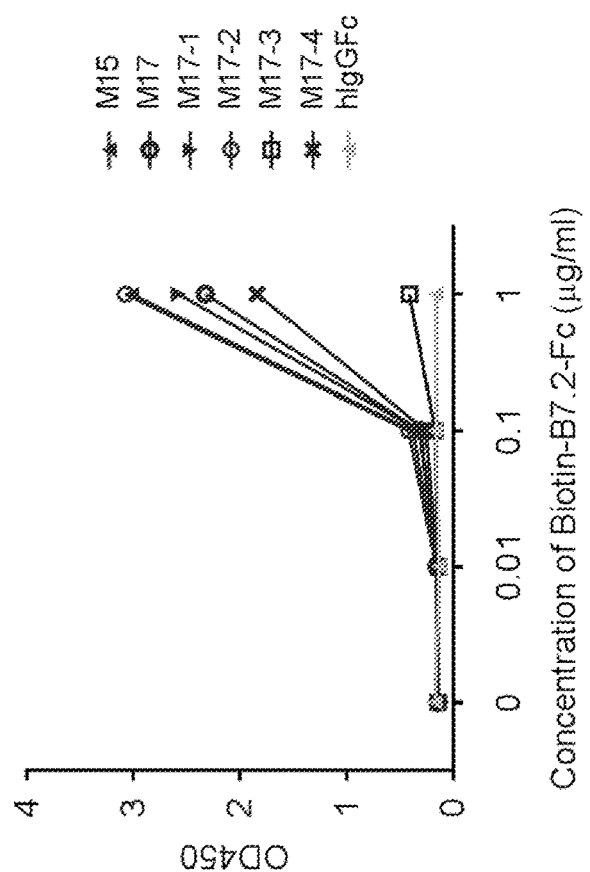
Figure 21B:
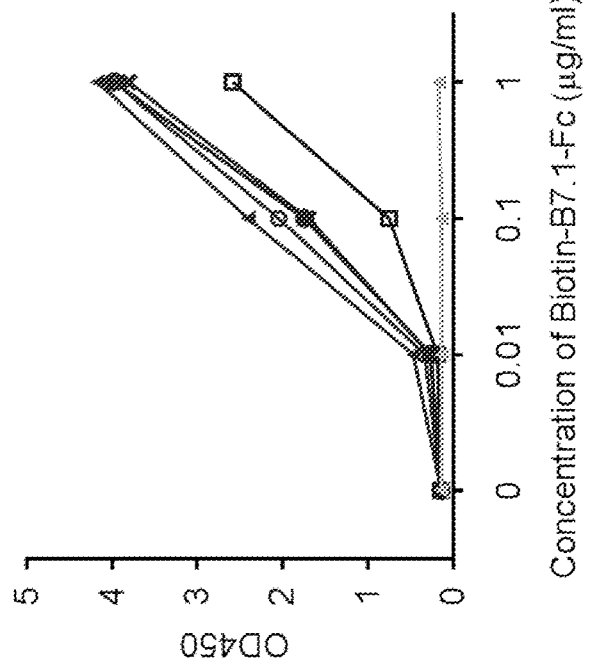

FIGS. 21A and B. Identifying CTLA-4Fc mutant proteins that retain binding to biotinylated B7-1 and B7-2 proteins. Mutant CTLA4-Fc fusion proteins (1 μg/ml) were coated onto 96-well plates. Biotinylated B7-Fc (FIG. 21A) and B7-2Fc (FIG. 21B) were incubated with the plates at the given concentrations and detected with streptavidin-conjugated IRP. Data shown are means of duplicate experiments.

Figure 22A:
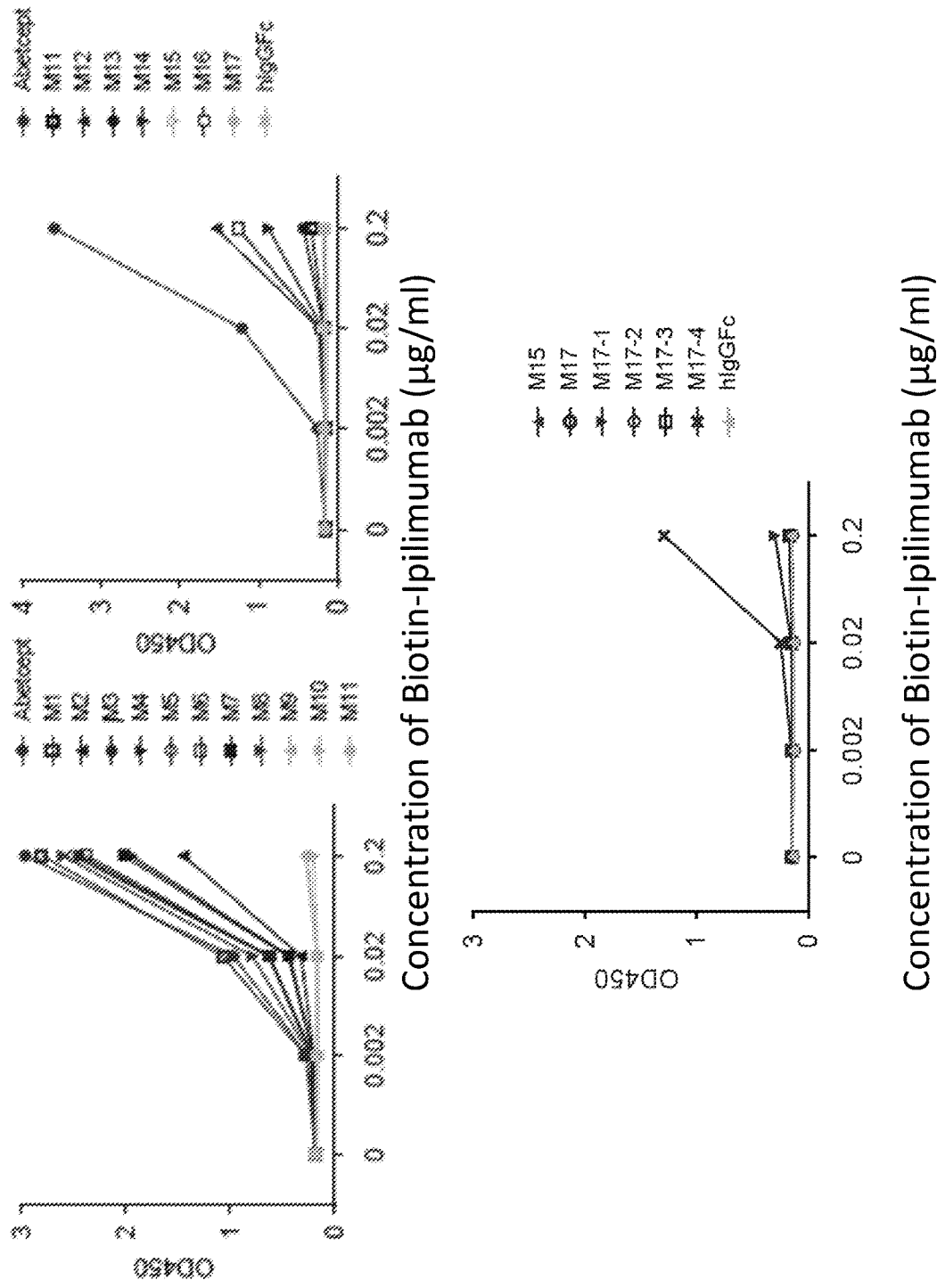
Figure 22B:
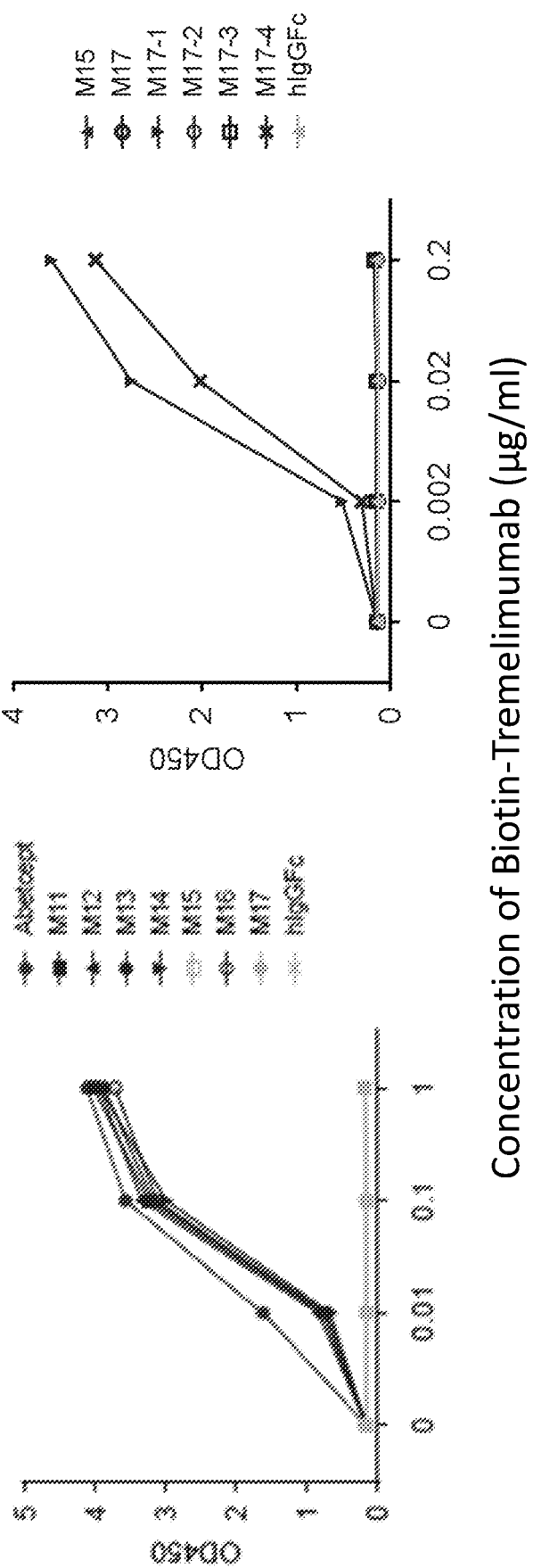

FIGS. 22A and B. Identifying CTLA-4Fc mutant proteins that have lost binding to biotinylated Ipilimumab (FIG. 22A) and Tremelimumab (FIG. 22B). Mutant CTLA4-Fc fusion proteins (1 μg/ml) were coated onto 96-well plates. Biotinylated antibody mAb2 was incubated with the plates at the given concentrations and detected with streptavidin-conjugated HRP. Data shown are FIGS. 23A and B. Identifying CTLA-4Fc mutant proteins that have lost binding to biotinylated mAb4. CTLA4-Fc fusion proteins M1-M17 were coated onto 96-well plates. Biotinylated antibody mAb4 was incubated with the plates at the given concentrations and detected with streptavidin-conjugated HRP. Data shown are means of duplicate experiments.

Figure 24B:
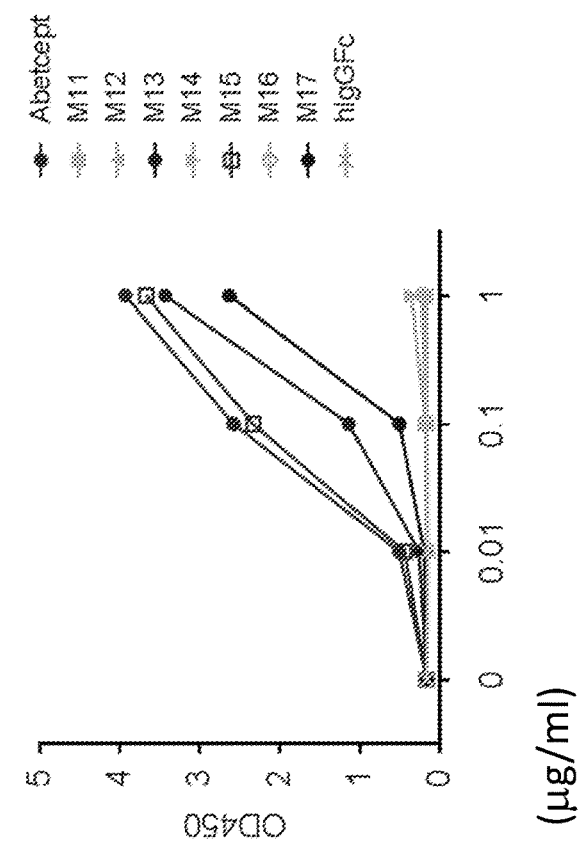
Figure 24A:
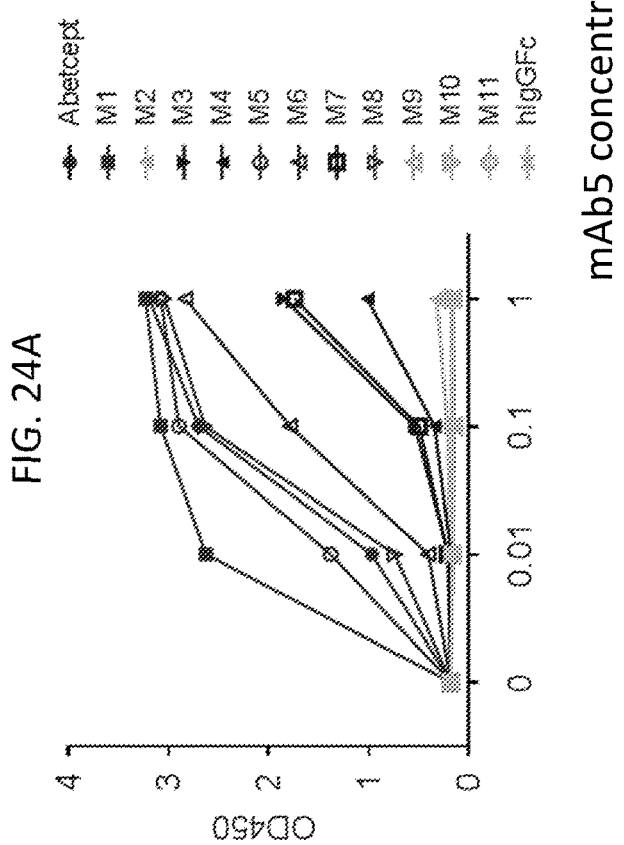

FIGS. 24A and B. Identifying CTLA-4Fc mutant proteins that have lost binding to biotinylated mAb5. CTLA4-Fc fusion proteins M1-M17 were coated onto 96-well plates. Biotinylated antibody mAb5 was incubated with the plates at the given concentrations and detected with streptavidin-conjugated HRP. Data shown are means of duplicate experiments.

Figure 25B:
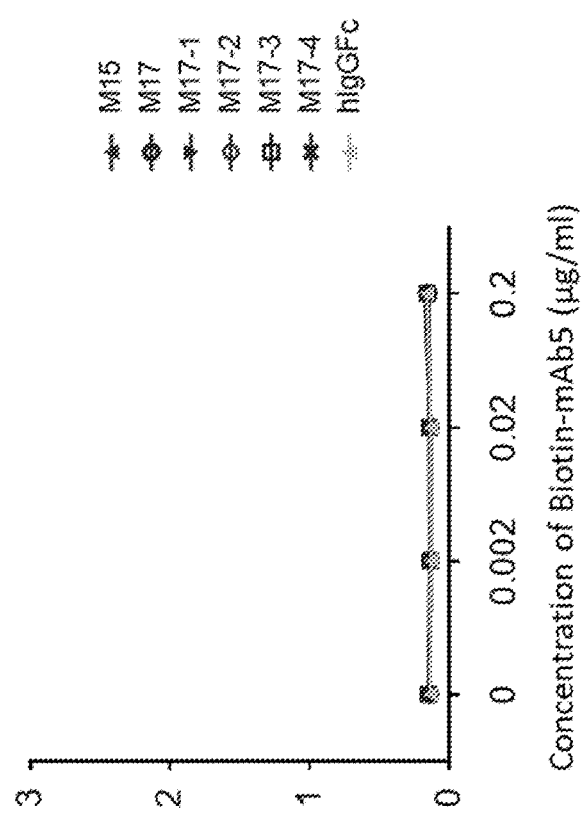
Figure 25A:
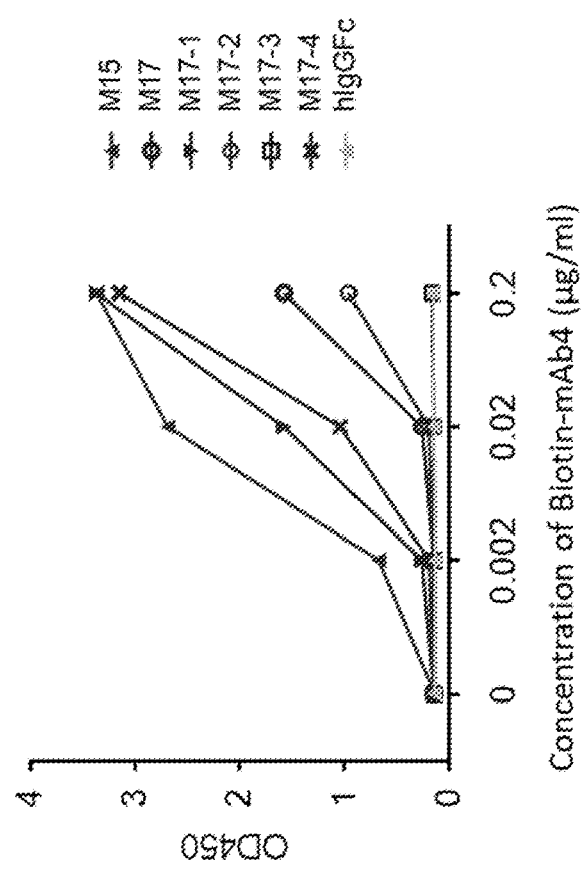

FIGS. 25A and B. Identifying CTLA-4Fc mutant proteins that have lost binding to biotinylated mAb4 (FIG. 25A) and mAb5 (FIG. 25B). Mutant CTLA4-Fc fusion proteins (1 µg/ml) were coated onto 96-well plates. Biotinylated antibody mAb4 (FIG. 25A) or mAb5 (FIG. 25B) was incubated with the plates at the given concentrations and detected with streptavidin-conjugated HRP. Data shown are means of duplicate experiments.

Figure 26E:
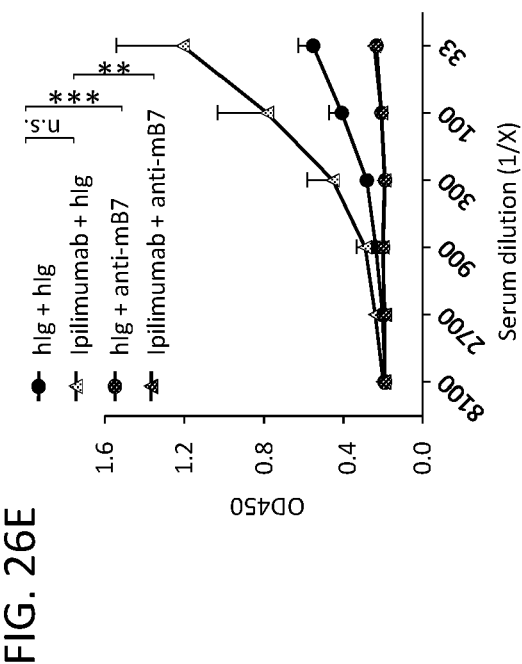
Figure 26F:
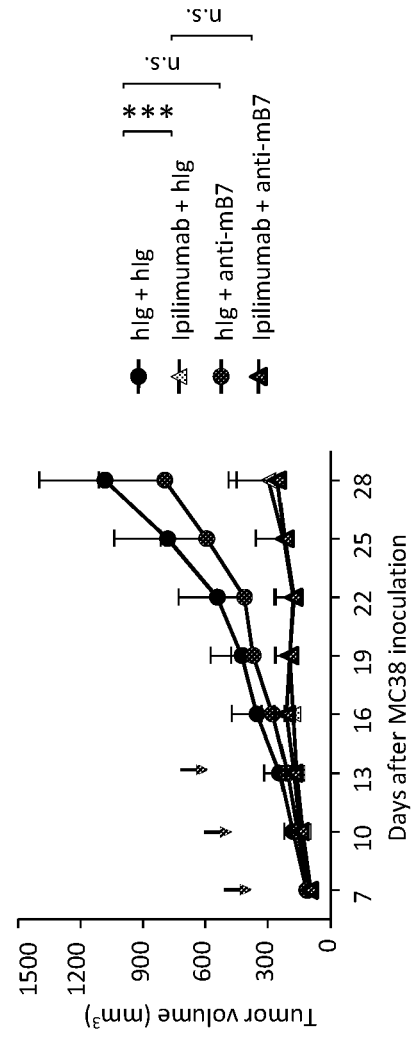

FIGS. 26A-F. The therapeutic effect of ipilimumab is not achieved by blocking B7-1 and/or B7-2. FIG. 26A. Confirmation of the blocking activities of anti-B7 mAbs. CHO cells expressing mouse B7-1 or B7-2 were incubated with a mixture of 20 mg/ml anti-B7-1 (upper panel) or anti-B7-2 (lower panel) and biotinylated human CTLA-4Fc (2 mg/ml) for 1 hour. After washing away unbound proteins, the cell surface CTLA-4Fc was detected by PE-conjugated streptavidin and measured by flow cytometry. Data shown are representative FACS profiles and have been repeated twice. FIG. 26B. Diagram of the experimental design: MC38 tumor-bearing Ctla-4" mice received anti-B7-1 and anti-B7-2 antibodies (300 µg/mouse/injection, once every 3 days for a total of 3 injections) in combination with either control Ig or Ipilimumab. Mice that received Ipilimumab without anti-B7-1 and anti-B7-2 were used as a positive control for tumor rejection and hIg was used as a negative control. FIGS. 26C and D. Saturation of B7-1 and B7-2 by antibody treatments as diagrammed in FIG. 268. The PBL from mice treated as shown in FIG. 26B, were stained with fluorochrome-conjugated anti-B7-1 and anti-B7-2 mAbs at 24 hours after anti-B7 treatment. PBL from Cd80$^{-/-}$Cd86$^{-/-}$ mice were used as negative control. FIG. 26E. Functional blockade of B7 by anti-B7-1 and anti-B7-2 mAbs based on ablation of antibody responses. Sera were collected at day 22 after tumor challenge to evaluate anti-human IgG antibody responses. FIG. 26F. Saturating blocking of B7-1 and 17-2 by anti-B7-1 and anti-B7-2 mAbs does not affect the immunotherapeutic effect of Ipilimumab. Data shown are tumor volumes over time and have been repeated twice with similar results.

Figure 27:
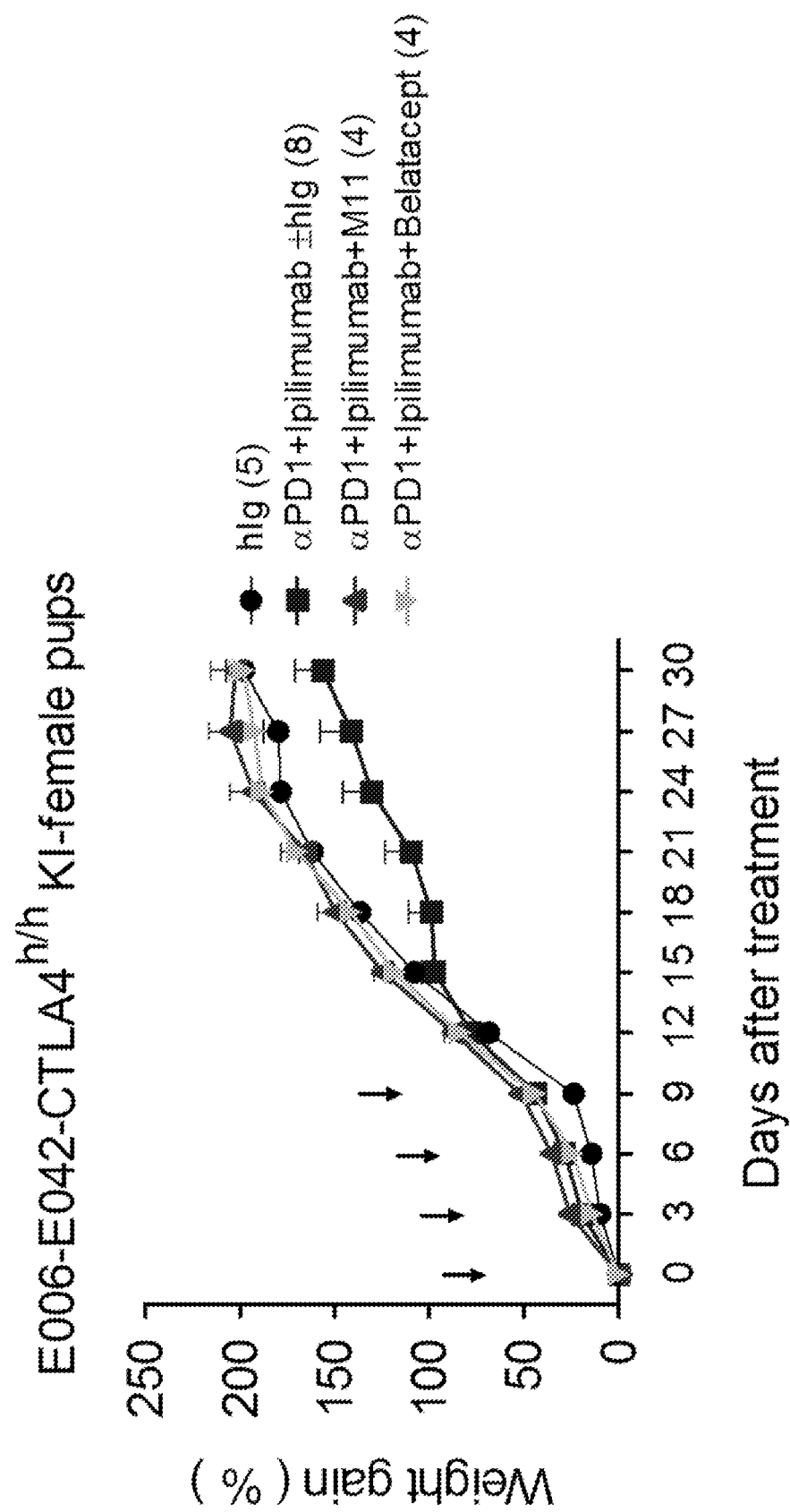

FIG. 27. CTLA-4-Fc fusion proteins M11 and M15 protect mice against irAE caused by combination therapy with anti-PD-1 and anti-CTLA-4 (Ipilimumab).

FIGS. 28A and B. CTLA4-Fc mutants M15 and M17 do not interfere with the immunotherapeutic effect of Ipilimumab. The Ctla-4$^{h/m}$ heterozygous mice were transplanted with MC38 tumors and treated with Ipilimumab in combination with either control IgG Fc or CTLA-4 mutant proteins at time points indicated by the arrows. FIG. 28A. Reduction in tumor sizes. FIG. 28B. Survival of tumor-bearing mice, using tumor sizes of reached 2 cm in diameter as early removal criteria.

Figure 29B:
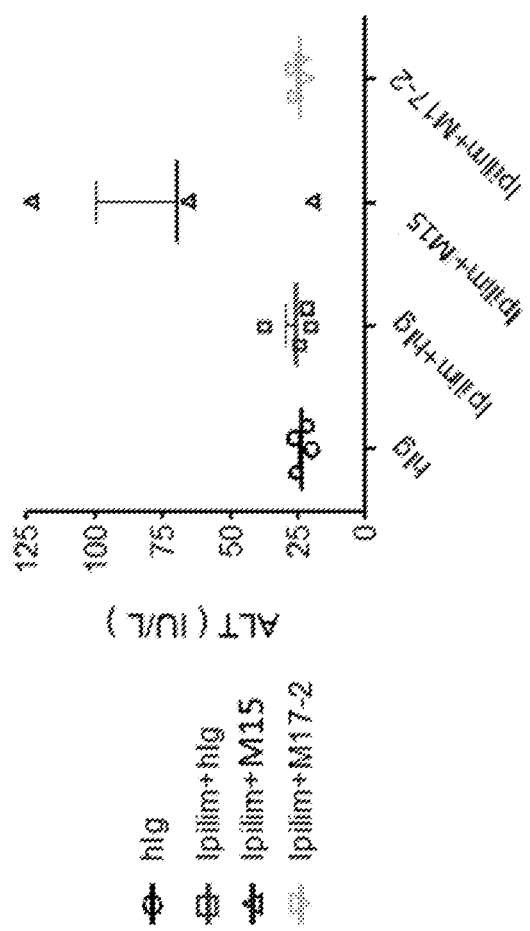
Figure 29A:
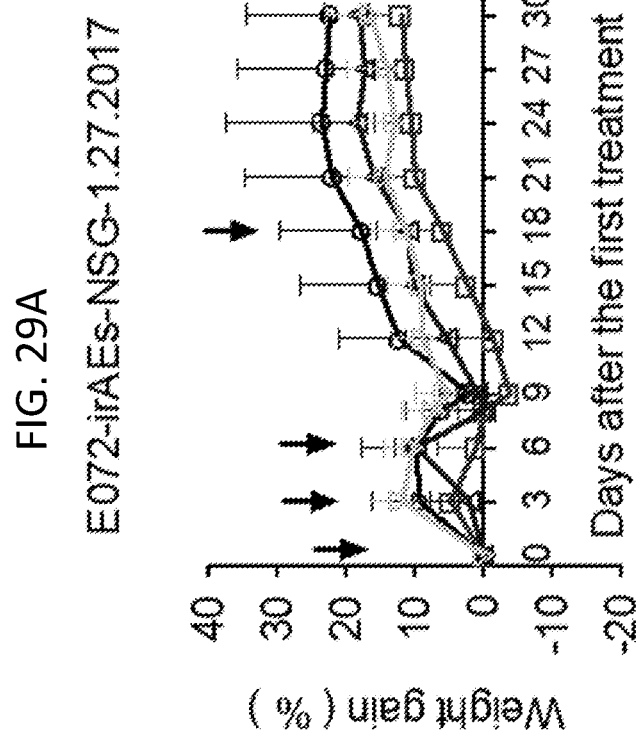

FIGS. 29A and B. Protective function of M15 and M17-2 against Ipilimumab-induced weight-loss (FIG. 29A) and potential liver toxicity of M15 (FIG. 29B) in NSG mice reconstituted with human CD34$^+$ hematopoietic stem cells. 16 female humanized mice were randomized into 4 groups based on the weight human leukocyte reconstitution and % of human T cells in the blood. The 4 groups were treated, respectively, with either control human IgG Fc (400 µg/injection), Ipilimumab (100 µg/injection)+human IgG Fc (300 µg/injection), Ipilimumab (100 µg/injection)+M15 (300 µg/injection), or Ipilimumab (100 µg/injection)+M17-2 (300 µg/injection) on days 0, 3 and 6. On day 18, the mice received one more injection in which the dose of Ipilimumab were 200 µg/mice+human IgG Fc (300 µg/injection), Ipilimumab (100 µg/injection)+M15 (300 µg/injection), or Ipilimumab (100 µg/injection)+M17-2 (300 µg/injection). Mice were monitored over 30 days for weight changes, using day 0 as 100%. FIG. 29B. Elevation of ALT was observed in mice that received Ipilimumab along with M15 but not M17-2.

FIGS. 30A-F. Differential effect of M15 and M17-2 in Ipilimumab-induced T cell activation based on the analysis of spleen T cells on day 31. Mice were treated as described in FIG. 29 and sacrificed on day 31 for flow cytometry. CD4 (FIGS. 30A-C) and CD8 (FIGS. 30D-F) frequency of CD4 and CD8 T cells (FIGS. 30A and D), central memory (CD44$^{hi}$CD62L$^{hi}$) (FIGS. 30B and E) and effector memory cells (CD44$^{hi}$CD62L$^{lo}$) (FIGS. 30C and F) cells.

Figure 31:
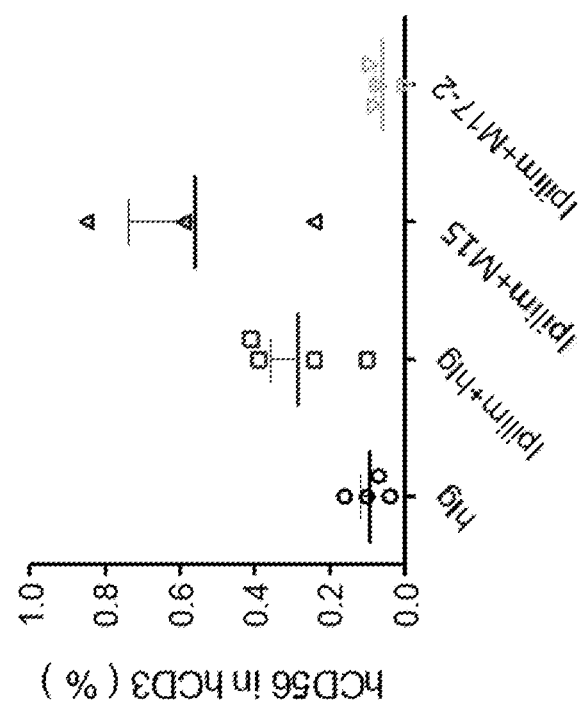

FIG. 31. Differential effect of M15 and M17 on the expansion of NKT cells. As detailed in FIG. 30, except that NK T cells (CD3'CD56') were analyzed. Mice were treated as described in FIG. 29 and sacrificed on day 31 for flow cytometry.

Figure 32B:
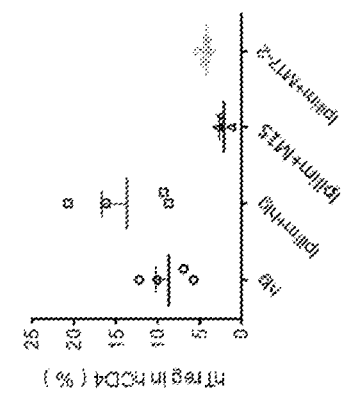
Figure 32D:
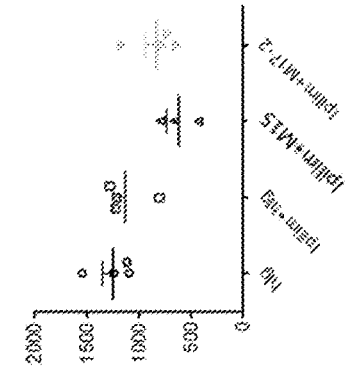
Figure 32A:
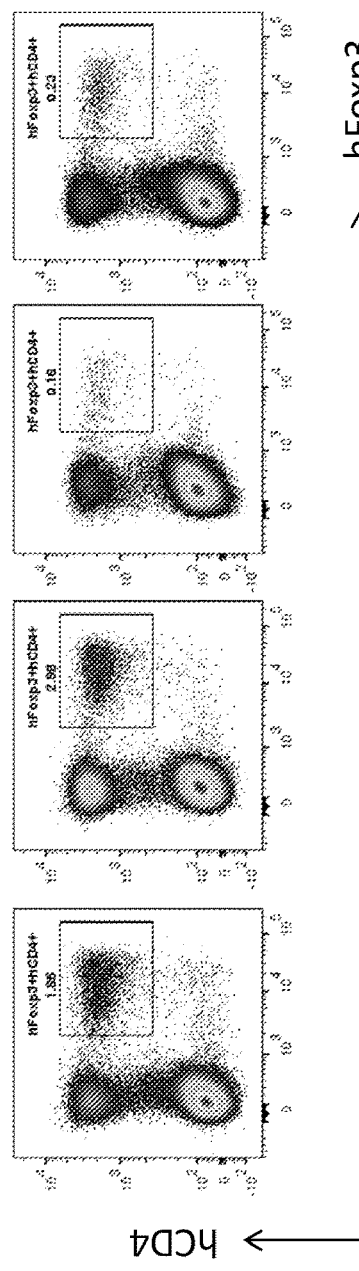
Figure 32C:
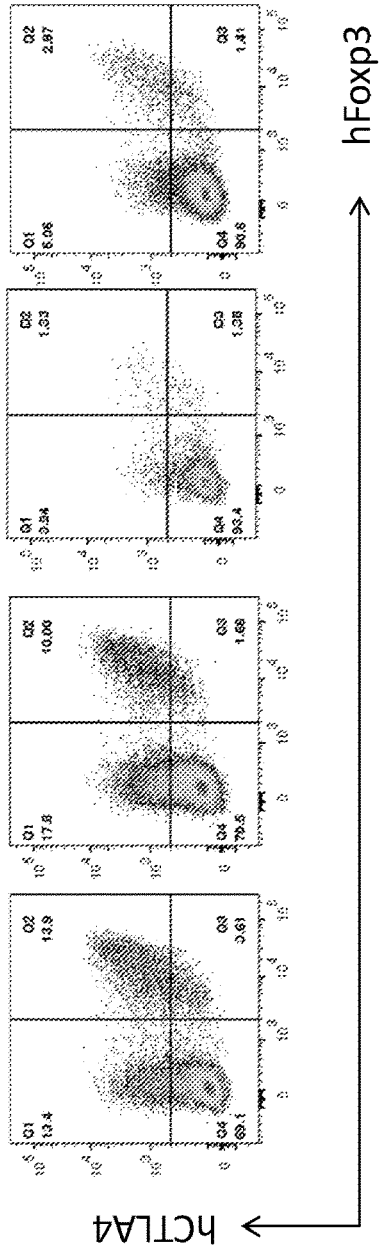

FIGS. 32A-D. Differential effect of M15 and M17-2 on the frequency of Treg (FIGS. 32A and B) and their expression of CTLA-4 protein (FIGS. 32C and D). Mice were treated as described in FIG. 29 and sacrificed on day 31 for flow cytometry.

DETAILED DESCRIPTION

The inventors have discovered soluble CTLA-4 fusion proteins containing mutations that prevent their binding by most anti-CTLA-4 mAbs while retaining their ability to bind B7-1 and B7-2 on antigen presenting cells (APC). Surprisingly, these fusion proteins prevent the autoimmune adverse effects of anti-CTLA-4 mAbs without affecting the cancer therapeutic effects of anti-CTLA-4.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "protein", "peptide" or "polypeptide" refers to a chain of amino acids of any length, regardless of modification (e.g., phosphorylation or glycosylation). The amino acids may be natural, synthetic, or a modification or combination of natural and synthetic. A polypeptide of the present invention may be a recombinant polypeptide, a natural polypeptide or a synthetic polypeptide, preferably a recombinant polypeptide.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. A "fragment" of a polypeptide thus refers to any subset of the polypeptide that is a shorter polypeptide of the full length protein. Generally, fragments will be five or more amino acids in length.

As used herein, the term "soluble portion" of a protein means that portion of the full length polypeptide that does not include any part of the transmembrane portion or segment. For example, with respect to CTLA-4, a soluble portion would include the extracellular portion (with or without the N-terminal signal sequence) but would not include any part of the transmembrane portion (or, at least, not enough to reduce solubility). Thus, the ECD of human CTLA-4 is shown as SEQ ID NO: 3 (i.e., amino acids 36-161 of the full length sequence (SEQ ID NO: 1), where amino acids 1-35 comprise the signal sequence and are not included in the mature extracellular, and thus soluble, protein.

As used herein, the term "fusion protein" is defined as one or more amino acid sequences joined together using methods known in the art. The joined amino acid sequences thereby form one fusion protein. Fusion proteins known in the art include the hexa-histidine peptide, the hemagglutinin "HA" tag, which corresponds to an epitope derived from the influenza hemagglutinin protein (Wilson, I. A. et al. (1984) "The Structure Of An Antigenic Determinant In A Protein," Cell, 37:767-778) and the "flag" tag (Knappik, A. et al. (1994) "An Improved Affinity Tag Based On The FLAG Peptide For The Detection And Purification Of Recombinant Antibody Fragments," Biotechniques 17(4):754-761).

A derivative, analog or homolog, of a polypeptide (or fragment thereof) of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such derivatives and analogs are deemed to be within the scope of those skilled in the art from the teachings herein.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (12) and 95-102 (113) in the heavy chain variable domain; ref. 44) and/or those residues from a "hypervariable loop" (i.e., residues 26-32 (L1), 50-52 (L2) and 91-96 (L3) in the light chain variable domain and 26-32 (111), 53-55 (112) and 96-101 (H3) in the heavy chain variable domain; Ref. 45). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies, single chain antibodies, disulfide-linked Fvs (sdFv), intrabodies, and anti-idiotypic (anti-Id) antibodies (including, e.g., anti-Id and anti-anti-Id antibodies to antibodies of the invention). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "active fragment" refers to a portion of a natural polypeptide or antibody, or a polypeptide with high sequence homology (for example, at least 80%, 85%, 90%, 95%, 98%, or 99% amino acid sequence identity) to a natural polypeptide or antibody and which retains biological activity. Representative examples of "biological activity" include the ability to bind B7 proteins and to bind their natural receptors or to be bound by a specific antibody. For example, an active fragment of CTLA-4 would be capable of binding B7.1 or B7.2 or by binding to a ligand of CTLA-4. In preferred embodiments, such a fragment would consist of the extracellular domain (ECD) of a CTLA-4 protein.

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

"Substantially identical" may mean that a first and second amino acid sequence are at least 60%, 65%, 70%, 75%. 80%, 85%. 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

As used herein, a "variant" polypeptide contains at least one amino acid sequence alteration as compared to the amino acid sequence of the corresponding wild-type polypeptide. As used herein, an "amino acid sequence alteration" can be, for example, a substitution, which may be conservative, a deletion, or an insertion of one or more amino acids. Variant may also mean a protein with an amino acid sequence that is substantially identical to a referenced protein with an amino acid sequence, and may retain at least one biological activity. A variant may be a derivative, analog or homolog, of a polypeptide. A variant may also be a soluble portion of a polypeptide. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. B7-CTLA-4 Interactions and Immunotherapy

The ability of T cells to optimally mediate an immune response against an antigen requires two distinct signaling interactions. First, antigen that has been arrayed on the surface of antigen-presenting cells (APC) must be presented to antigen-specific naive T cells in the form of MHC: peptide complex (1, 2). Such presentation delivers a signal via the T cell receptor (TCR) that directs the T cell to initiate an immune response that will be specific to the presented antigen. Second, a series of co-stimulatory signals, mediated through interactions between the APC and distinct T cell surface molecules, triggers first the activation and proliferation of the T cells and ultimately their inhibition (3-5). Thus, the first signal confers specificity to the immune response whereas the second signal serves to determine the nature, magnitude and duration of the response while limiting immunity to self. Of particular importance among these second signal molecules is binding between the B7.1 (CD80) (6) and B7.2 (CD86) (7-9) ligands of the APC and the CD28 and CTLA-4 receptors (10-12) of the T-lymphocyte.

CD28 (Cluster of Differentiation 28) and Cytotoxic T-lymphocyte-associated antigen-4 (CTLA-4) are members of the immunoglobulin super family of proteins and are involved in the regulation of T-cell activation. CD28 is constitutively expressed on naive T cells and binds B7.1 and B7.2 providing a co-stimulatory signal required for T cell activation and survival. In contrast, upon T cell activation, CTLA-4 is upregulated on T cells and competes with CD28 for binding to B7.1 and B7.2, thereby transmitting a suppressive signal for T cell activation.

B7 family molecules have a membrane proximal IgC (constant) domain and a membrane distal IgV (variable) domain. The CD28-like family of receptors for these ligands share a common extracellular IgV-like domain. Interactions of receptor-ligand pairs are mediated predominantly through residues in the IgV domains of the ligands and receptors (Schwartz, et al., Nature Immunol., 3:427-434 (2002)). Crystallographic analysis revealed that the CTLA-4/B7 binding interface is dominated by the interaction of the CDR3-analogous loop from CTLA-4, composed of a MYPPPY motif (Schwartz, et al., Nature, 410:604-608 (2001); and Stamper, et al., Nature. 410:608-611 (2001)).

Antibodies against CTLA-4 have been shown to block the interaction between CTLA-4 and the costimulatory molecules B7.1 and B7.2 in vitro. This blockade removes the CTLA-4-mediated inhibitory signal on T-cells and thereby stimulates a natural immune response that can be used as a therapy against cancer. Treatment with anti-CTLA-4 antibodies has been shown to be a powerful tool for enhancing anti-tumor immunity in preclinical models (10). Monotherapy with an antibody against CTLA-4 promoted rejection of transplantable tumors of various origins. Based on promising preclinical tumor model studies, the clinical potential of antibodies against CTLA-4 has been explored in different human malignancies. Although anti-CTLA-4 (Ipilimumab, marketed as Yervoy, disclosed in U.S. Pat. No. 6,984,720) has demonstrated efficacy in treating melanoma, treatment and targeting of CTLA-4 is associated with autoimmune like toxicities. Characteristic side effects from inhibition of CTLA-4 are generally called immune-related adverse events (irAEs) and the most common irAEs are skin rash, hepatitis, colitis and endocrinopathies, particularly hypopituitarism. Therefore, there is a desire to improve the safety of anti-CTLA-4 antibodies by reducing the associated irAEs.

The inventors have surprisingly discovered that both clinically proven therapeutic anti-human CTLA-4 mAb and two anti-mouse Ctla-4 mAbs induce tumor rejection without blocking B7-CTLA-4 interactions under physiologically relevant conditions. Therefore, blocking CTLA-4 interactions with B7.1 or B7.2 is not necessary for tumor rejection even for the mAb that can potently block these B7-CTLA-4 interactions. These data refute the hypothesis that anti-CTLA-4 mAb confers immunotherapeutic effect through checkpoint blockade (108). Furthermore, the inventors have identified an anti-CTLA-4 antibody, L3D10, with reduced immune related toxicities demonstrating that cancer immunity and irAEs can be uncoupled genetically.

3. Soluble CTLA-4

Accumulating data demonstrated that the human CTLA-4 gene encodes two different isoforms of proteins through alternative splicing: one with a trans-membrane domain which is thus likely to be anchored in the membrane, and another that lacks the trans-membrane domain and is predicted to be secreted (sCTLA-4, SEQ ID NO: 4) (128). Importantly, genetic studies demonstrated that a polymorphism of CTLA-4 that reduces the relative abundance of the soluble isoform strongly associates with multiple autoimmune diseases (64). The fact that subjects with autoimmune prone alleles express less sCTLA-4 mRNA suggests that sCTLA-4 may be protective. This is notion is supported by the broad therapeutic effect of abatacept (129,130), which is a form of soluble CTLA-4, and by the genetic study in which the selective ablation of the sCTLA-4 isoform accelerated the development of type I diabetes in the mice (131).

Based on these genetic data it the inventors had the insight that the antibody that shows the poorest binding to sCTLA-4 should be associated with the fewest irAE. Indeed, the inventors identified an anti-CTLA-4 antibody, L3D10, with reduced immune related toxicities that was shown to have reduced binding to sCTLA-4 relative to membrane bound or immobilized CTLA-4. Based on the impact of the antibodies on the body weight gain in mice treated with anti-CTLA-4 antibodies during the perinatal period, a strong correlation was found among four anti-CTLA-4 mAbs: Ipilimumab has the strongest binding for sCTLA-4 and is the most toxic anti-CTLA-4, whereas L3D10 had the weakest binding to sCTLA-4 and was the least toxic. Furthermore, humanization of the L3D10 antibody preferentially reduced binding to sCTLA-4 and appeared to further improve the safety profile over the parent antibody.

In order to map the CTLA-4 binding epitope of the L3D10 parent antibody and humanized variants, the inventors took advantage of the fact that the mouse and human CTLA-4 proteins are cross-reactive between species to B7-1, but not to the anti-CTLA-4 antibodies. Accordingly, the inventors designed a number of mutants of the human CTLA-4Fc protein in which clusters of amino acids from the human CTLA-4 protein were replaced with amino acids from the murine Ctla-4 protein (SEQ ID NO: 5). As the anti-CTLA-4 antibodies used in this study do not bind to murine Ctla-4, binding of the anti-human CTLA-4 antibodies should be abolished when key residues of the antibody binding epitope are replaced with murine amino acids. Accordingly, the inventors have shown that the L3D10 binding site of CTLA-4 maps directly adjacent to the B7-1 binding motif, MYPPPY (SEQ 1D NO: 50). This correlates well with the demonstrated ability of the antibody to block B7-CTLA-4 interactions both in vitro and in vivo. By contrast, Ipilimumab, does not block binding of 137.1 or B7.2 to abatacept under physiological conditions and so it must also bind a region that does not include the MYPPPY motif. However, as it does not show reducing binding to sCTLA-4, the binding domain must be different from antibody L3D10.

Endogenous sCTLA-4 is produced by fusion of the truncated C-terminal end of the extracellular IgV domain directly to the intracellular domain, without the intervening transmembrane domain. Accordingly, there are only 12 amino acids of the CTLA-4 extracellular domain C-terminal to the MYPPPY motif in sCTLA-4, whereas the endogenous membrane bound version has 21 amino acids. Based on this, without being bound by theory, it appears that an antibody that binds to polymorphic C-terminal domain residues, such as L3D10, is more likely to lose reactivity to sCTLA-4. Furthermore, the inventors have demonstrated that it is possible to mutate these amino acids in the CTLA-4Fc protein in this region so that they no longer bind anti-CTLA-4 antibodies.

4. Recombinant CTLA-4 Proteins

CTLA-4Fc fusion protein (abatacept, marketed as Orencia) is a selective costimulation modulator comprising the extracellular domain of CTLA-4 fused to the Fc region of human IgG1 (shown in FIG. 1B; SEQ ID NO:2) that inhibits T cell (T lymphocyte) activation by binding to B7.1 and 87.2, thereby blocking interaction with CD28. In vitro, abatacept decreases T cell proliferation and inhibits the production of the cytokines TNF alpha (TNFα), interferon-γ, and interleukin-2. Activated T lymphocytes are implicated in the pathogenesis of Rheumatoid Arthritis (RA) and are found in the synovium of patients with RA. In a rat collagen-induced arthritis model, abatacept suppresses inflammation, decreases anti-collagen antibody production, and reduces antigen specific production of interferon-γ. Based on this preclinical activity, abatacept has been developed and approved for the treatment of RA and Juvenile Idiopathic Arthritis (JIA) in humans.

Although capable of reducing immune responses, CTLA-4Fc fusion proteins comprising the endogenous CTLA-4 extracellular domain, such as abatacept, are incapable of reducing or mitigating the immune related toxicities associated with anti-CTLA-4 immunotherapies as the activity of the two molecules are offsetting. The CTLA-4 fusion protein such as the abatacept will not only reduce the therapeutic effect of anti-CTLA-4 mAbs by binding directly to the antibodies to prevent them from binding to endogenous cell-associated CTLA-4 molecules, but will also be rendered ineffective themselves as they will be cleared from circulation after forming immune-complex with circulating anti-CTLA-4 mAbs.

Given that both blocking and non-blocking anti-CTLA-4 antibodies have anti-tumor effects and antibodies demonstrating reduced irAEs are associated with reduced binding to sCTLA-4, the inventors engineered a panel of soluble CTLA-4 proteins with mutations that prevent binding by most anti-CTLA-4 mAbs that were tested while retaining their ability to bind B7-1 and B7-2 on the antigen-presenting cells, which is critical for the pathogenesis of autoimmune disease and irAEs. Such proteins, by virtue of their retained 137 binding activity, can be used in the treatment of autoimmune diseases such as RA and IA. Furthermore, such proteins can be used in combination with anti-CTLA-4 immunotherapy treatment to reduce the associated irAEs, while leaving the anti-tumor activity of the immunotherapy intact.

a. CTLA-4 Proteins

Provided herein is a CTLA-4 protein comprising (a) the extracellular domain of mature human CTLA-4 (SEQ ID NO: 3) or mouse CTLA-4 (SEQ ID NO: 6), (b) an amino acid set forth in one of SEQ ID NOS: 24-40 and 46-49, (c) a variant of the foregoing, or (d) an active fragment of the foregoing. The CTLA-4 protein may be soluble. The CTLA-4 protein may further comprise an N-terminal signal peptide. The CTLA-4 protein may retain the ability to bind human B7.1 and 87.2 but lack the ability to bind an anti-CTLA-4 antibody. In one specific embodiment, the CTLA-4 protein does not bind to Ipilimumab or Tremelimumab under physiological conditions. In particular, the CTLA-4 protein may comprise an amino acid sequence set forth in SEQ ID NO: 34, 36, 38, 39, 40, 46, 47, or 48. The CTLA-4 protein may be isolated.

b. CTLA-4 Fusion Proteins

The CTLA-4 protein may be fused at its N- or C-terminal end to another protein. The other protein may be a portion of a mammalian Ig protein, which may be human or mouse. The portion may comprise a Fc region of the Ig protein. The Fc region may comprise the hinge region and C12 and C13 domains of the Ig protein. The Ig protein may be human IgG1, IgG2, IgG3, IgG4, or IgA. The Ig protein may also be IgM, and the Fc portion may comprise the hinge region and CH3 and CH4 domains of IgM. In one embodiment, the Fc region is human IgG1 comprising the amino acid sequence set forth in SEQ ID NO: 41. The CTLA-4 protein may comprise an amino acid sequence selected from the group consisting of SEQ ID NOS: 7-23 and 42-45, and particularly selected from the group consisting of SEQ ID NO: 17, 19, 21, 22, 23, 42, 43, and 44.

The CTLA-4 protein may also be fused at its N- or C-terminus to a protein tag, which may comprise GST. His, or FLAG. Methods for making fusion proteins and purifying fusion proteins are well known in the art.

5. Anti-B7 Antibodies

Another embodiment of the invention relates to an anti-B7 antibody composition that binds at least one of human B7-1 and B7-2. The anti-B7 antibody may bind to one or both of endogenous B7-1 and 137-2, and may neutralize activity without affecting the cancer immunotherapeutic activity of anti-CTLA-4 antibodies. The anti-B7 antibody may be humanized to minimize anti-drug antibodies. The anti-B7 antibody may be a monoclonal antibody, and may be cross-reactive with both B7-1 and 137-2. In yet another embodiment, a bispecific antibody may comprise antigen-binding domains of two antibodies, respectively binding to 137-1 or B7-2

6. Production

The CTLA-4 protein or anti-B7 antibody may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CTLA-4 protein may also be produced from a stable cell line that expresses CTLA-4 protein from a vector or a portion of a vector that has been integrated into the cellular genome. The stable cell line may express CTLA-4 protein from an integrated replication-defective retroviral vector. The expression system may be GPEx™.

The CTLA-4 protein or anti-B7 antibody can be purified using, for example, chromatographic methods such as affinity chromatography, ion exchange chromatography, hydrophobic interaction chromatography, DEAE ion exchange, gel filtration, and hydroxylapatite chromatography. In some embodiments, fusion proteins can be engineered to contain an additional domain containing amino acid sequence that allows the polypeptides to be captured onto an affinity matrix. For example, a CTLA-4 protein or anti-B7 antibody comprising the Fe region of an immunoglobulin domain can be isolated from cell culture supernatant or a cytoplasmic extract using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Fusion proteins can additionally be engineered to contain a secretory signal (if there is not a secretory signal already present) that causes the fusion protein to be secreted by the cells in which it is produced. The secreted fusion proteins can then conveniently be isolated from the cell media.

7. Pharmaceutical Compositions

The invention further concerns a pharmaceutical composition comprising a therapeutically effective amount of one or more of the above-described CTLA-4 proteins and anti-B7 antibodies, and a physiologically acceptable carrier or excipient. Preferably, compositions of the invention comprise a prophylactically or therapeutically effective amount of the CTLA-4 protein or anti-B7 antibody and a pharmaceutically acceptable carrier In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers may be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, tale, sodium chloride, dried skim milk, glycerol, propylene, glycol, water, ethanol and the like. The composition, if desired, may also contain minor amounts of wetting or emulsifying agents, or pH buffering agents. These compositions may take the form of solutions, suspensions, emulsion, tablets, pills, capsules, powders, sustained-release formulations and the like.

Generally, the ingredients of compositions of the invention may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline may be provided so that the ingredients may be mixed prior to administration.

The compositions of the invention may be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

8. Methods of Treatment a. Autoimmune Disease

The CTLA-4 protein or anti-B7 antibody, or pharmaceutical composition thereof may be used to treat an inflammatory or autoimmune disease. Representative inflammatory or autoimmune diseases and disorders that may be treated using B7-H4 fusion polypeptides include, but are not limited to, rheumatoid arthritis (RA), systemic lupus erythematosus (SLE), alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis (MS), myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis. In a particular embodiment, the autoimmune disease may be rheumatoid arthritis (RA) or Juvenile Idiopathic Arthritis (JIA). The CTLA-4 protein or anti-B7 antibody, or pharmaceutical composition thereof may be administered to a subject in need thereof. The subject may be a mammal such as a human.

The CTLA-4 protein or anti-B7 antibody, or pharmaceutical composition thereof may be combined with another drug, such as a disease-modifying antirheumatic drug (DMARD). The drug may be a nonsteriod anti-inflammatory drug (NSAID), which may be a propionic acid derivative, an acetic acid derivative, an enolic acid derivative, a fenamic acid derivative, or a selective Cox2 inhibitor. The drug may also be a corticosteroid or Methotrexate. The drug may be a biologic, which may be a TNF-α antagonist such as an anti-TNF-α antibody or a fusion protein that binds to TNF-α (Enbrel), an anti-CD20 mAb, an antagonist of costimulatory molecule CD80 and CD86 such as a monoclonal antibody or a fusion protein (CTLA-4Ig) that binds to the two molecules, or an antagonist for a receptor of either IL-1 or IL-6. The CTLA-4 protein or anti-B7 antibody, or pharmaceutical composition thereof, and the other drug may be administrated together or sequentially.

b. Immunotherapy

The CTLA-4 protein or anti-B7 antibody, or pharmaceutical composition thereof may also be used to mitigate, reduce or treat the immune related adverse events (irAEs) associated with anti-CTLA-4 immunotherapy in cancer patients. The CTLA-4 protein may be administered prophylactically (before the emergence of irAEs) or therapeutically (after the emergence of irAEs). In particular, the CTLA-4 protein or anti-B7 antibody, or pharmaceutical composition thereof may be administered to a subject in combination with, or on a background of, anti-CTLA-4 immunotherapy. The subject may be cancer patient. In one embodiment, the CTLA-4 protein or anti-B7 antibody, or pharmaceutical composition thereof is used prophylactically to prevent irAEs before anti-CTLA-4 treatment is initiated or the before the clinical signs of irAEs emerge. In another embodiment, the CTLA-4 protein or anti-B7 antibody, or pharmaceutical composition thereof is used therapeutically to treat irAEs after anti-CTLA4 treatment is initiated and the clinical symptoms are diagnosed.

c. Methods of Administration

The CTLA-4 protein or anti-B7 antibody, or pharmaceutical composition thereof may be administered by a method including, but not limited to, parenteral administration (e.g., intradermal, intramuscular, intraperitoneal, intravenous and subcutaneous), epidural, and mucosal (e.g., intranasal and oral routes). In a specific embodiment, the CTLA-4 protein or anti-B7 antibody, or pharmaceutical composition thereof is administered intramuscularly, intravenously, or subcutaneously. The composition may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

EXAMPLES

Example 1

Chimeric 1.3D10 Antibody has Equivalent Activity as 10D1 in Causing Tumor Rejection In the clinic, the anti-CTLA-4 antibody, Ipilimumab (mab 10D1), has been shown to improve the survival of cancer patients but induces significant autoimmune adverse effect. Using human CTLA-4 gene knock-in mice and hu-PBL-Scid mice, it was previously demonstrated that mouse anti-human CTLA-4 antibodies reduced tumor growth, and identified L3D10 as the most effective among the panel of mAbs tested (21).

Figure 2:
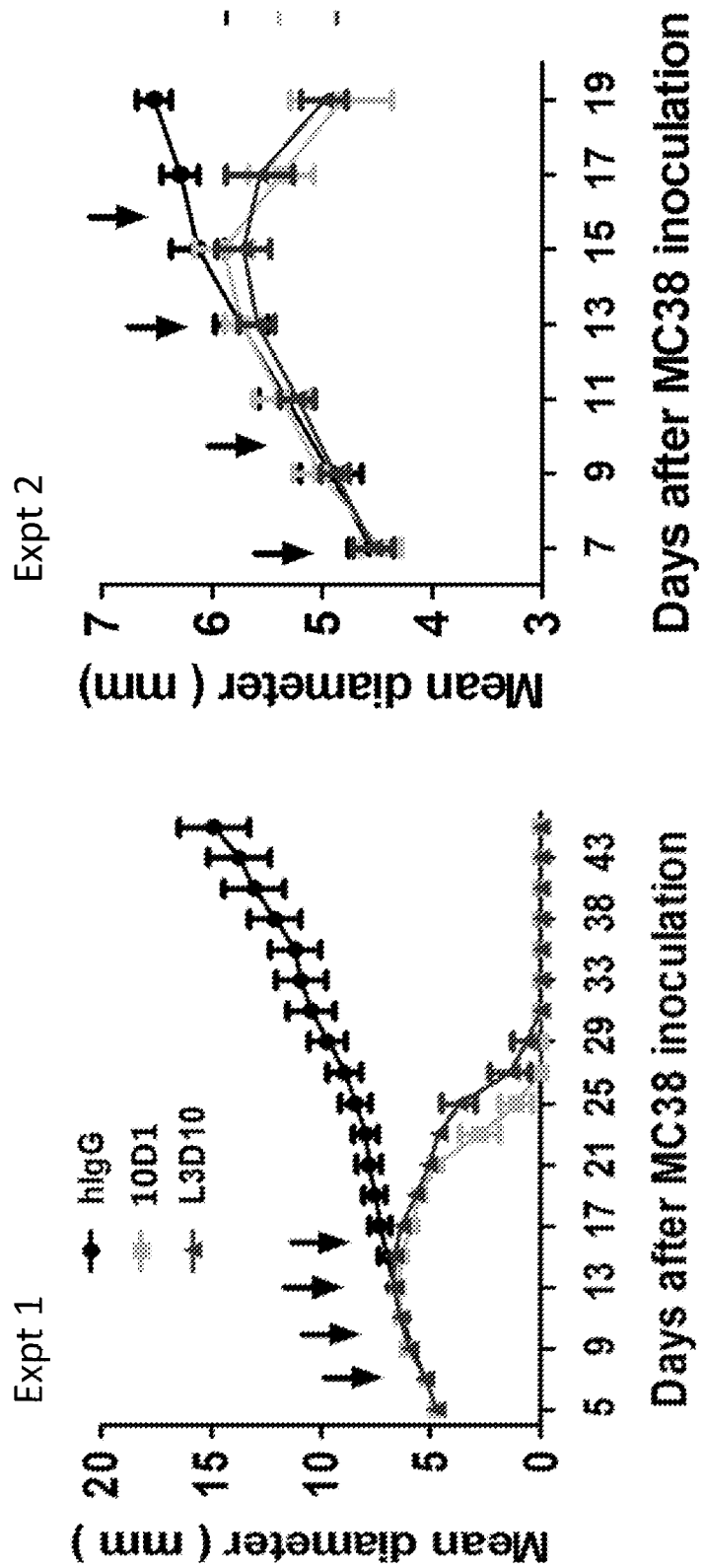
FIG. 2. Therapeutic effect of chimeric L3D10 and 10D1 in the MC38 tumor model. Human CTLA-4-knock-in mice with body weight of approximately 20 grams were used for the study. $1\times10^6$ MC38 tumor cells were injected subcutaneously into Ctla-4$^{h/h}$ mice and when the tumor reached a size of 0.5 cm in diameter, tumor bearing mice were randomized into three groups with 5 or 6 mice each. Mice were then treated (i.p.) with 100 µg/injection of 10D1, chimeric L3D10 or control hIgGFc on days 7, 10, 13, and 16 as indicated by the arrows. The results of duplicate experiments are shown (left and right panels) and data shown are means and S.D. of tumor size (n=6 per group in the left panel, n=5 per group in the right panel). L3D10 and 10D1 have similar therapeutic effect in this model and are both able to induce complete remission of established tumors. The diameters (d) of the tumors were calculated using the following formula: $D=\sqrt{(ab)}$, $V=ab2/2$, where a is the long diameter, while b is the short diameter. Statistical analyses were performed by two-way repeated measures ANOVA (treatment×time). For the left panel: P=10D1 vs. hIgGFc: 5.71e-07; L3D10 vs. hIgGFc: P=5.53e-07; 10D1 vs. L3D10: P=0.869.

The availability of human CTLA-4 gene knockin mice (20) provided with an unprecedented opportunity to test biological activity of the chimeric L3D10 anti-human CTLA-4 antibody, comprising the parental L3D10 variable region and human IgG1 constant domain (the Fc region), with clinically used anti-CTLA-4 mAb, 10D1. In this humanized mouse model, a CTLA-4 gene encoding a product with 100% identity to human CTLA-4 protein is expressed under the control of endogenous mouse CTLA-4 locus. When the anti-tumor activity of the chimeric L3D10 and 101D1 were directly compared in the MC38 tumor model in human CTLA-4-knockin mice, it is clear that both antibodies were comparable in causing tumor rejection, whereas the tumors grew progressively in IgG control group. FIG. 2 shows the results of antibody treatment on tumor size from duplicate experiments.

Example 2

Reduction of Autoimmune Adverse Effect by Other Immunotherapeutic Antibodies

Figure 3:
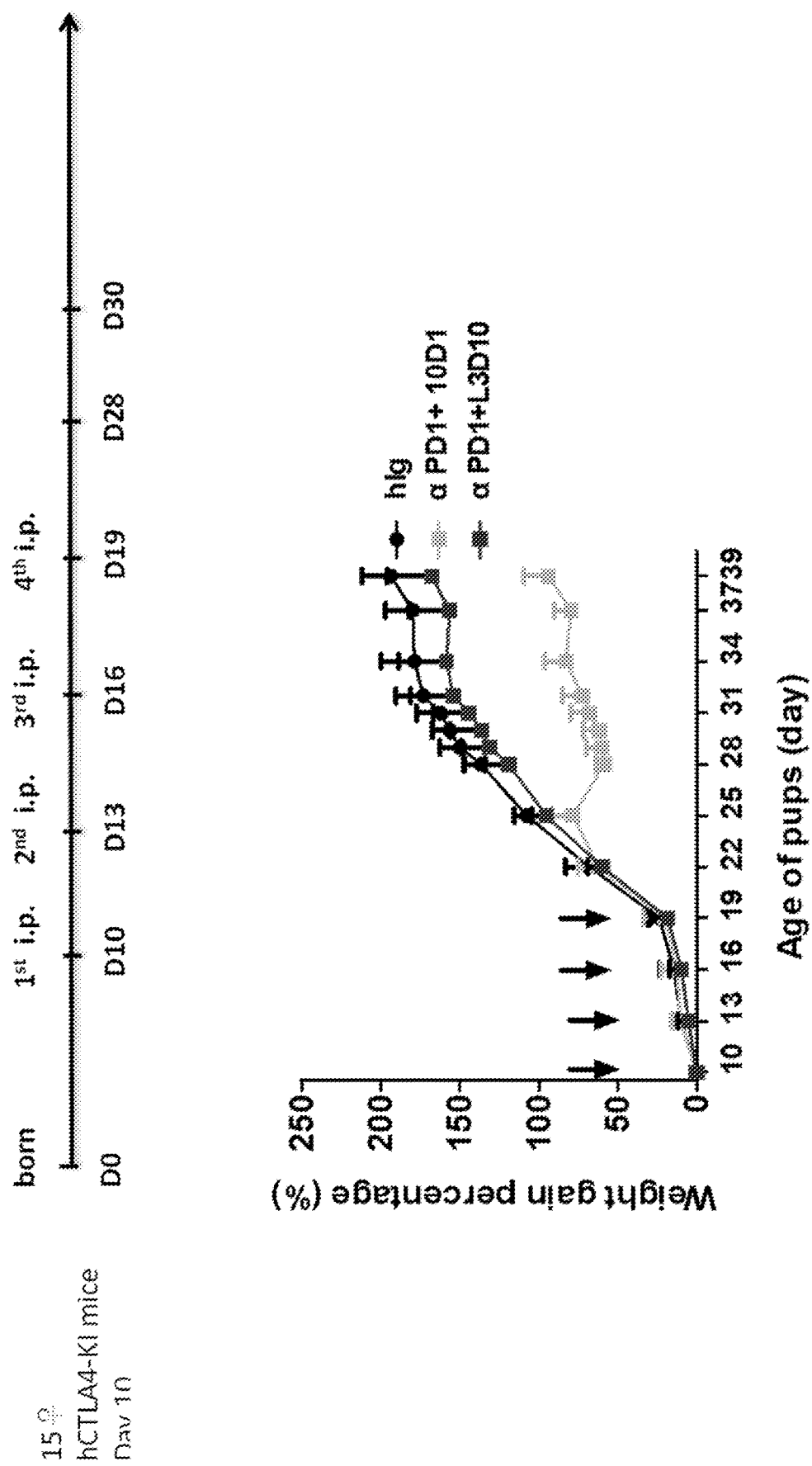
FIG. 3. Adverse effects of chimeric L3D10 and 10D1 in combination with anti-PD-1. Top panel depicts the experimental design. 10-day old female-only human CTLA-4-knockin mice with body weight of greater than 4 grams were used for the study. They received indicated proteins or their combinations. Arrows indicate time of treatment (100 µg/mice/treatment). Data shown are means and S.D. of % weight gains. Chimeric L3D10 and 10D1 have comparable cancer therapeutic effect in adult mice (FIG. 2) but distinct adverse effects are seen when 10D1 is combined with the anti-PD-1 mAb.

Recent clinical studies have revealed that combination therapy between anti-PD-1 and anti-CTLA-4 mAb further increase the survival of end-stage melanoma patients. However, 55% of the patients that received the combination therapy developed grades 3 and 4 immune related adverse events (irAEs). It is therefore critical to develop antibodies with less toxicity. We have developed an in vivo model that recapitulates the irAEs associated with the combination therapy of anti-CTLA-4 and anti-PD-1 mAbs observed in the clinic. In this model we treated human CTLA-4 gene knockin mice (CTLA-$4^{h/h}$) during the perinatal period with high doses of anti-PD-1 and anti-CTLA-4 mAbs. We found that while the young mice tolerate treatment of individual mAbs, combination therapy with anti-PD-1 and 10D1 causes severe irAE with multiple organ inflammation, anemia and, as shown in FIG. 3, severely stunted growth. In contrast, when combined with anti-PD-1, chimeric L3D10 exhibits only mild irAE as demonstrated by normal weight gain.

Figure 4:
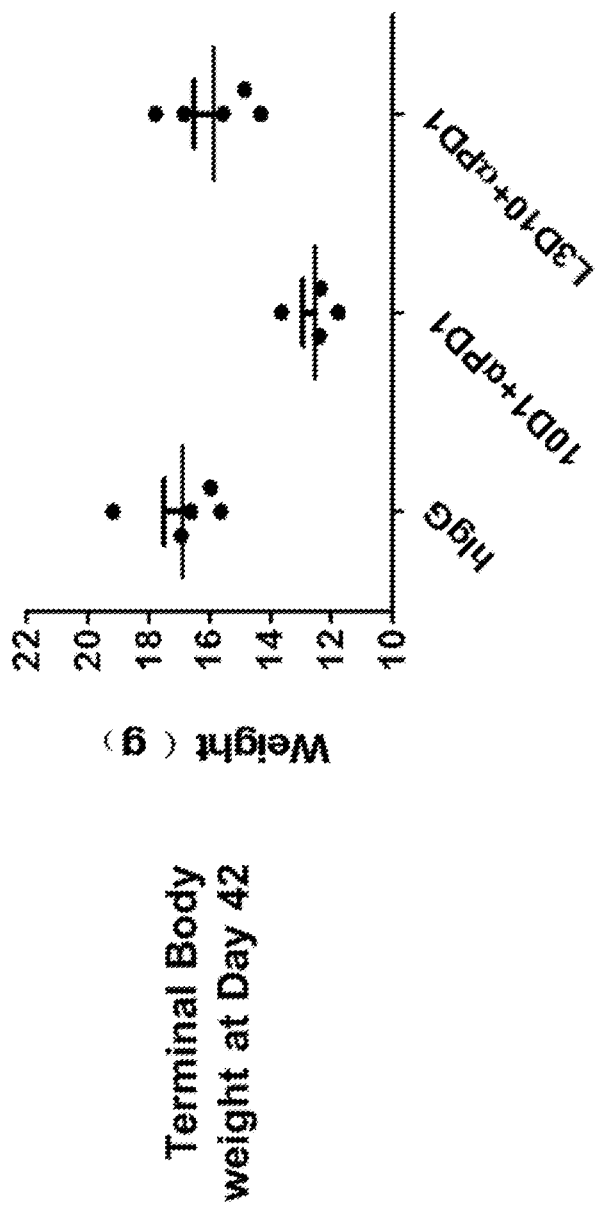
FIG. 4. Adverse effects of chimeric L3D10 and 101D in combination with anti-PD-1. The graph shows the terminal body weight on Day 42 in the mice from the experiment outlined in FIG. 3 that received either control IgG, 10D1+anti-PD-1 or chimeric L3D10+anti-PD-1 (n=5 per group). A significant reduction in weight is observed with the anti-PD1+10D1 combination, which was not seen with the anti-PD-4, Chimeric L3D10 combination.

To further examine to relative toxicity of chimeric L3D10 compared to 10D1 when administered in combination with anti-PD-1, we looked at the pathological effects in the CTLA-4$^{h/h}$ knockin mice at 42 days after administration. As shown in FIG. 4, terminal body weight (day 42) in mice treated with L3D10+anti-PD-1 was similar to mice treated with hIgG negative control antibody. However, by comparison, the weight of mice treated with 10D1+anti-PD-1 was much lower. Accordingly, when we looked at the gross anatomy of these mice, the Uterus/Ovary/Bladder and thymus were noticeably smaller in mice treated with 10D1+PD-1 (FIG. 5). Again, the organs in mice treated with L3D10+anti-PD-1 was comparable to hIgG control. In contrast, the hearts dissected from mice treated with 10D1 appeared slightly larger in size with a noticeably whiter appearance. As a result we decided to look at erythropoiesis within the mice and observed clear differences in the mice treated with 10D1+anti-PD-1 relative to the groups treated with L3D10+anti-PD-1 or control antibody, which were fairly similar. As shown in FIG. 6A, the bone marrow from mice treated with 10D1+anti-PD-1 had a noticeably whiter color and the isolated blood was almost completely white in color (FIG. 6B). In accordance with this, when we took at closer look at the cells undergoing the different stages of blood development using CD71 and CD119 markers. Representative FACS profiles are shown in FIG. 6C, while summary data are presented in FIG. 6d. These data revealed a statistically significant reduction in the number of cells undergoing Stage IV development in the 10D1+anti-PD-1 treated mice (FIG. 6D).

Figure 7:
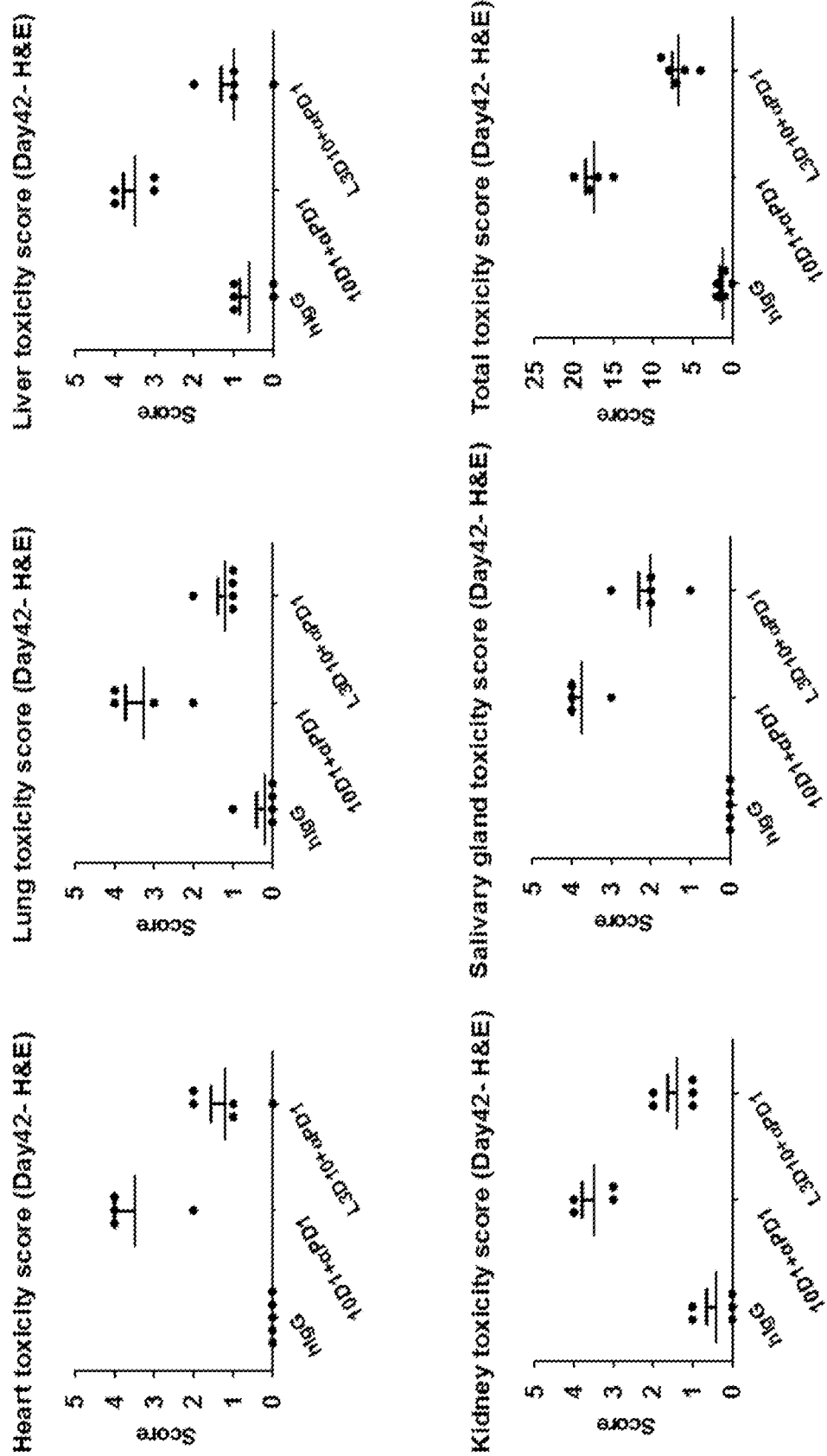
FIG. 7. Toxicity scores of mice treated with chimeric L3D10 and 10D1 in combination with anti-PD-1. This tissue data is summarized and shows the high toxicity scores of mice treated with 10D1+anti-PD-1 relative to L3D10+anti-PD-1 which has scores only marginally higher than the hIgG control mouse group.

To further determine the toxicology of L3D10 vs 10D1 in combination with anti-PD-1, we performed histological analysis of the heart, lung, salivary gland and the kidney and liver following fixation in 10% formalin for at least 24 hours. In each of the tissues studied, mice treated with 10D1+anti-PD-1 displayed a high level of T cell infiltration. The toxicity score, based on severity of inflammation, are summarized in FIG. 7, which shows the high toxicity scores of mice treated with 10D1+anti-PD-1 relative to L3D10+anti-PD-1 which has scores only marginally higher than the hIgG control mouse group.

Example 3

L3D10 has Reduced Binding for Soluble CTLA-4

Figure 8:
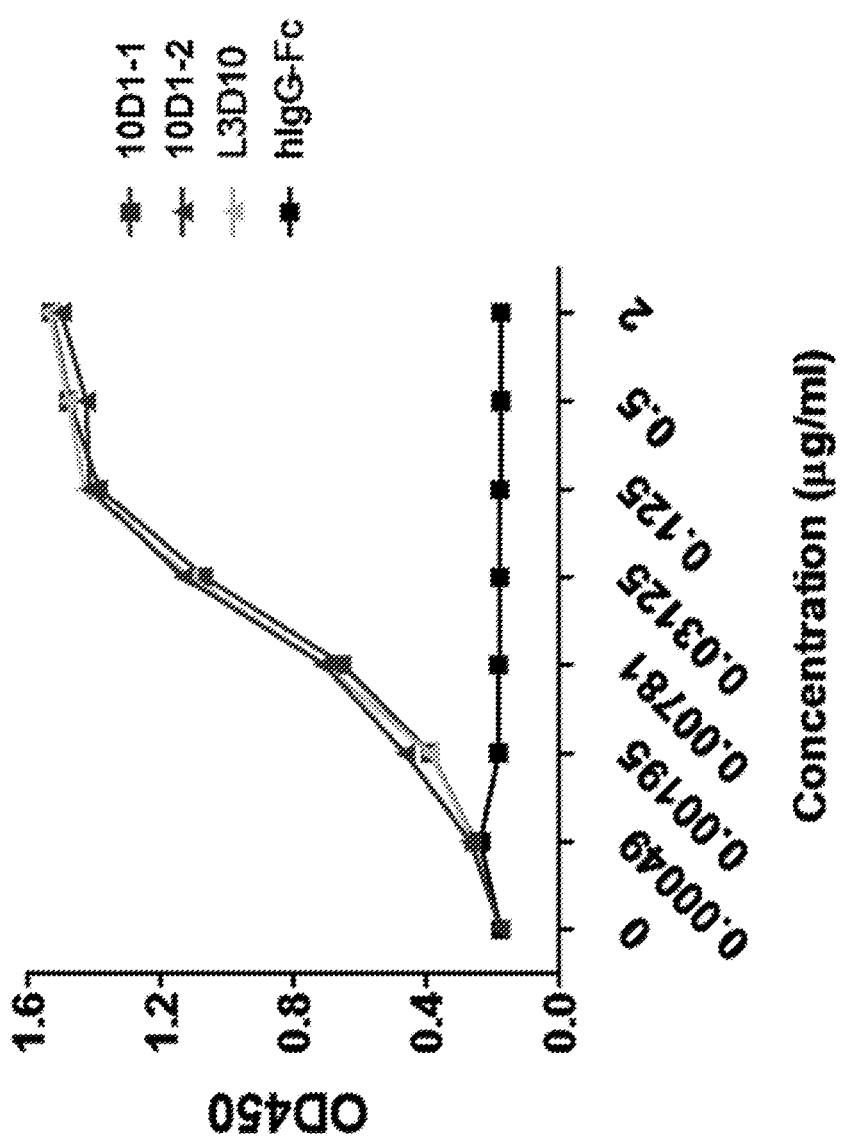
FIG. 8. L3D10 and 10D1 display similar binding patterns for plate immobilized CTLA-4. ELISA plates were coated with 1 µg/ml of CTLA-4-His protein (Sino Biological, China). The given concentration of biotinylated binding proteins were added and binding measured using HRP-conjugated streptavidin. 10D1-1 and -2 are two independent material lots of the same antibody. hIgG-Fc is a human Ig negative control.
Figure 9:
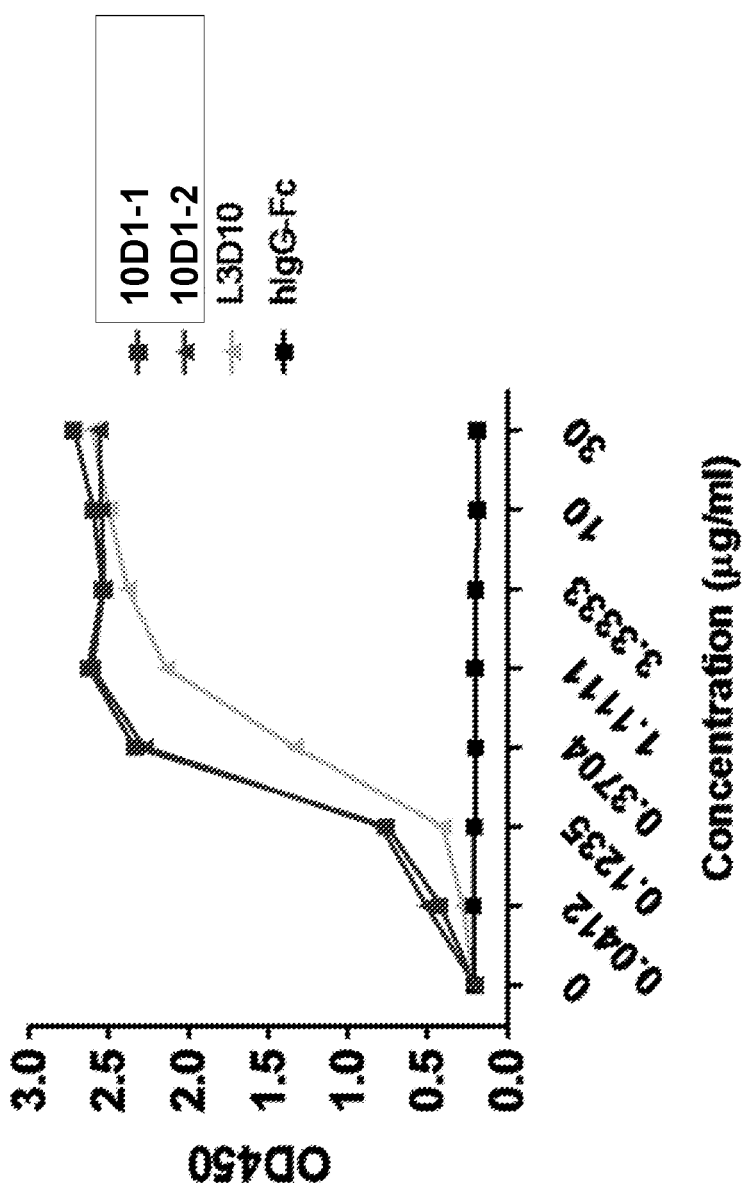
FIG. 9. L3D10 displays reduced binding soluble CTLA-4. Given concentration of anti-human CTLA-4 mAbs were coated on the plate overnight, after washing and blocking with bovine serum albumin, biotinylated CTLA-4-Fc was added at 0.25 µg/ml. After incubation and washing, the amounts of captured CTLA-4-Fc were measured using HRP-labeled streptavidin.

L3D110 and 10D1 display similar binding patterns for plate immobilized CTLA-4 (FIG. 8). As a possible explanation for the reduced toxicity of L3D10 relative to 10D1, particularly the increased T cell infiltration/activity associated with 10D1, we decided to look at the binding to soluble CTLA-4. We chose to look at this because the association between CTLA-4 polymorphism and multiple autoimmune diseases relates to the defective production of soluble CTLA-4 (67) and genetic silencing of the sCTLA-4 isoform increased the onset of type I diabetes in mice (131). Furthermore, soluble CTLA-4 (abatacept and belatacept) is a widely used drug for immune suppression. In accordance with this idea, when we looked at the relative binding to soluble CTLA-4, we observed a marked decrease in the binding of L3D10 relative to 10D1 (FIG. 9).

Figure 10:
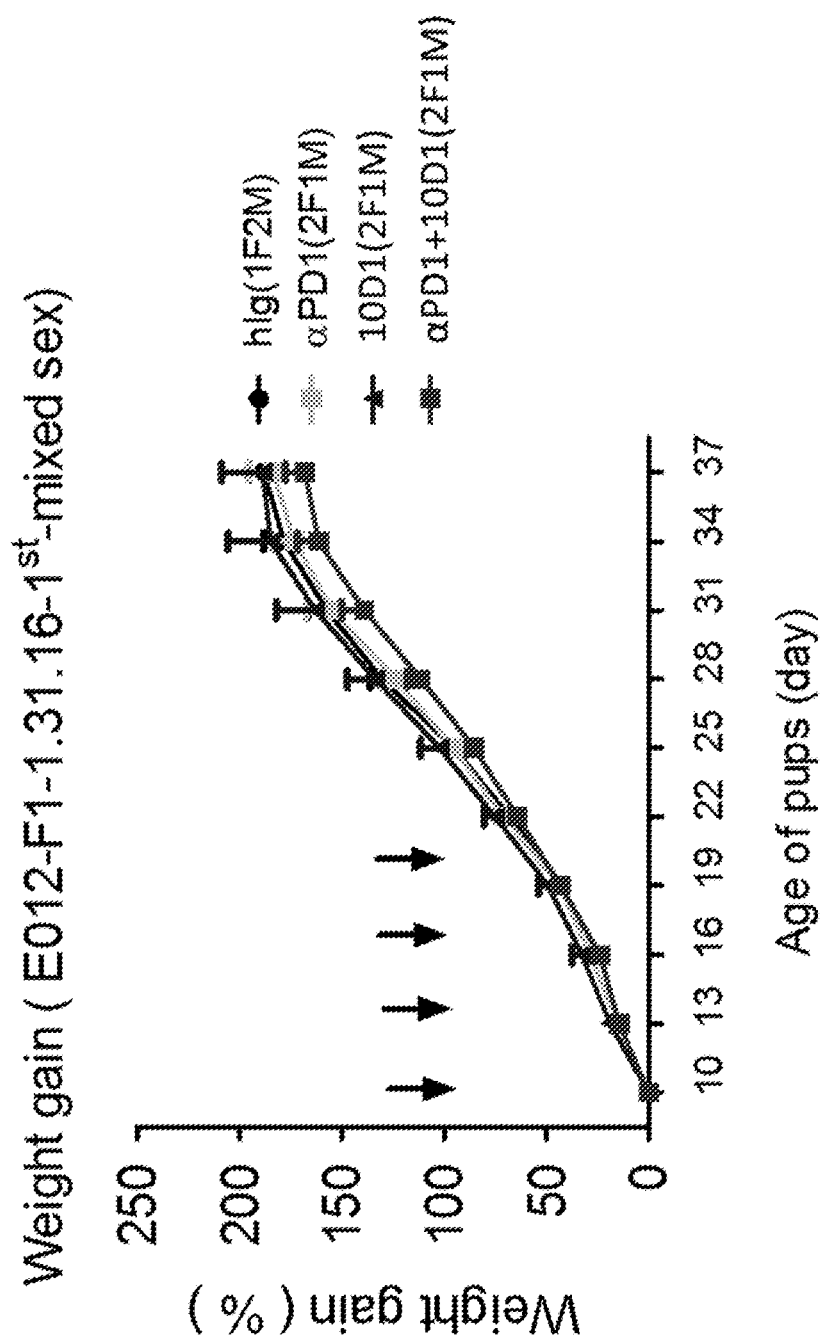
FIG. 10. 10D1+anti-PD-1 do not have significant toxicity in the Ctla-4$^{h/m}$ mice as evidenced by normal body weight gains in mice that received antibody treatment during the perinatal period. The mice received treatments with given antibody or combinations on days 10, 13, 16, 19 and 22 intraperitoneally (100 μg/mice/injection/antibody). Mice were weighed at least once every 3 days.

We have demonstrated that anti-CTLA-4 mAb induce robust tumor injection in heterozygous Ctla-4$^{h/m}$ mice in which only 50% of CTLA-4 molecules can bind to anti-human CTLA-4 mAbs. To determine if engagement of 50% of CTLA-4 is sufficient to induce irAE, we treated the Ctla-4$^{h/m}$ mice with anti-PD-1+10D1. As shown in FIG. 10, anti-PD-1+10D1 failed to induce weight loss in the Ctla-4$^{h/m}$ mice. Therefore, irAE and cancer immunity can be uncoupled genetically.

In vivo activity demonstrates that the L3D10 antibody retains its anti-tumor activity but displays reduced autoimmune adverse effect observed with other immunotherapeutic antibodies such as 10D1, indicating it is possible to enhance anti-tumor activity without exacerbating autoimmune adverse events. Accordingly, autoimmune side effects are not a necessary price for cancer immunity and that it is possible to uncouple these two activities. Characterization of L3D10 demonstrated that its ability to block the interaction of CTLA-4 with B7.1 and B7.2 is more effective than by 10D1. Further characterization demonstrates that L3D10 and 10D1 bind to immobilized CTLA-4 with a similar binding profile. However, L3D10 demonstrates much lower binding affinity to soluble CTLA-4 than 10D1.

Example 4

Humanized L3D10 Anti-CTLA-4 Antibodies

Humanized L3D10 antibodies were designed by creating multiple hybrid sequences that fuse select parts of the parental antibody sequence with the human framework sequences, including grafting of the CDR sequences into acceptor frameworks. We evaluated the anti-tumor activity of three of the humanized antibodies (mAb4, mAb5 and mAb6) compared to 10D1 and the chimeric L3D10 antibody using the syngeneic MC38 mouse tumor model in human CTLA-4-knockin mice described in Example 1 above. FIG. 11A shows the treatment schedule of the in vivo experiment; mice were given a total of 4 doses of antibody every 3 days starting on day 7 after inoculation. As shown in FIG. 11B, all humanized antibodies completely eradicated the tumor and were comparable to 10D1. Similar efficacy was seen using the syngeneic MC38 mouse tumor model in heterozygous Ctla-4$^{h/m}$ mice and the syngeneic B16-F1 melanoma mouse tumor model in human CTLA-4-knockin mice (data not shown).

Figure 12:
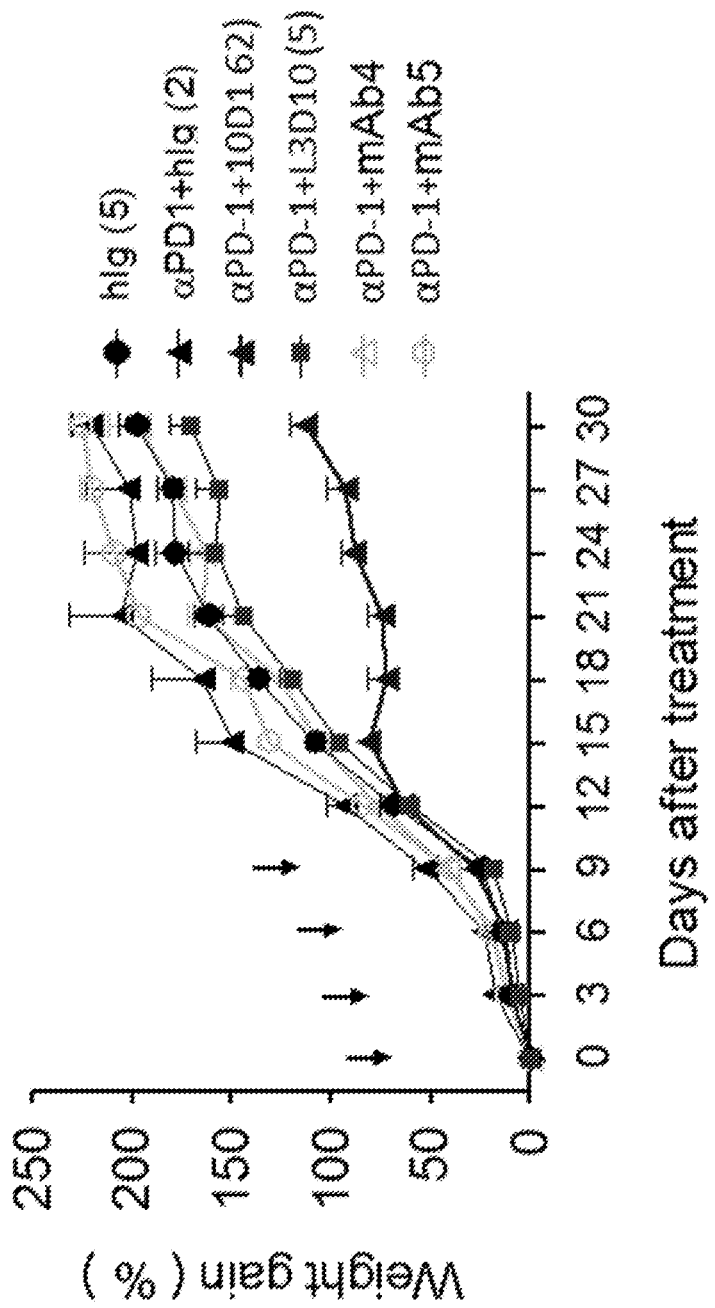
FIG. 12. Comparison among 10D1, mAb4 and mAb5 females for their combined toxicity with anti-PD-1 mAb. Female Ctla-4$^{h/h}$ mice were treated on days 10 or 11 days after birth with four injections of antibodies (100 μg/mice/injection, once every three days) or control Fc as specified in the legends. Mice were weighted once every 3 days. Data shown are means and SEM of % weight gain over a 30 day period. All mice were sacrificed on day 43 for histological analysis. The number of mice used per group is shown in the parentheses of labels.

To test if the superior safety profiles of L3D10 can be maintained after humanization, we compared mAb4 and mAb5 with 10D1 for their adverse effects when used in combination with anti-PD-1. As shown in FIG. 12, both mAb4 and mAb5 are less toxic than 10D1 when used in combination with anti-PD-1.

Example 5

Binding Characteristics of the Humanized Anti-CTLA-4 Antibodies in order to confirm that the humanized antibodies retained their CTLA-4 binding characteristics, we looked at binding to immobilized and plate bound CTLA-4. Humanization did not affect binding to immobilized CTLA-4 and all 3 humanized antibodies demonstrated similar binding to the parental chimeric L3D10 antibody (FIG. 13). However, humanization further reduces L3D10 binding to soluble CTLA-4 (FIG. 14).

We have demonstrated that chimeric L3D10 has a 1000-fold higher B7 blocking activity than 10D1. This raised an interesting possibility that blocking B7-CTLA-4 interactions may explain its lack of irAE. However, neither mAb4 nor mAb5 block B7-CTL-A4 interactions in vitro and in vivo. The fact that mAb4 and mAb5 show diminished irAE further supported the notion that blocking B7-CTLA-4 interaction is not responsible for improved safety of L3D10.

Given the proposed role for CTLA-4 in the protection against autoimmune diseases, we proposed reduced binding to soluble CTLA-4 as an underlying mechanism for improved safety profiles. To test this hypothesis, we used the growth weight gain among the female mice that received anti-PD-1+anti-CTLA-4 mAbs during the perinatal period as the basic indicator for irAE. Severe reduction in weight gain was observed in the mice that received both 10D1 and anti-PD-1, whereas those that received mAb5+anti-PD-1 had the lowest irAE, followed by mAb4 and then L3D10 (data not shown). The strict inverse correlation with reduced binding to sCTLA-4 are consistent with the central hypothesis. 8240779.1.

Example 6

Epitope Mapping of the L3D10 and Humanized Antibodies

In order to map the CTLA-4 binding epitope of the L3D10 antibody and the humanized variants, mAb4 and mAb5, we took advantage of the fact that the mouse and human CTLA-4 proteins are cross-reactive to B7-1, but not to the anti-CTLA-4 antibodies. The fact that anti-human CTLA-4 antibodies do not cross react with murine Ctla-4, presumably reflects differences in the amino acid sequence between human and mouse CTLA-4 in the extracellular domain. FIG. 15 shows the alignment of the human, macaque and mouse CTLA-4 extracellular domains and highlight the sequence conservation between human and macaque, while showing the numerous differences between the murine and primate sequences. Due to conservation of the MYPPPY binding motif (SEQ ID NO: 50), mouse and human CTLA-4 proteins are cross-reactive to B7-1 (72).

Accordingly, we designed 11 mutants of the human CTLA-4Fc protein, designated M1-M11 (SEQ ID NOS: 7-17) in which clusters of amino acids from the human CTLA-4 protein were replaced with amino acids from the murine Ctla-4 protein. The amino acids incorporated into each of the 11 mutants is shown in FIG. 15, and the amino acids sequences of the WT and mutant CTLA-4Fc proteins is shown in FIGS. 16A and B. As the anti-CTLA-4 antibodies used in this study do not bind to murine Ctla-4, binding of the anti-human CTLA-4 antibodies should be abolished when key residues of the antibody binding epitope are replaced with murine amino acids.

DNA vectors encoding 11 CTLA-4Fc mutant proteins were constructed based on the wild type human CTLA-4Fc sequence and proteins were produced by transient transfection in HEK293 at the 0.01 mL scale followed by one-step Protein A chromatography purification, and the yield is provided in Table 1 Many of the mutations appear to affect protein expression as indicated by their yields relative to the WT human CTLA-4Fc protein.

TABLE 1

WT and mutant CTLA-4Fc proteins produced transiently in HEK293 cells.

| Protein name | Yield (mg) |
|---|---|
| CTLA-4Fc WT control | 0.72 |
| Mutant 1 | 1.29 |
| Mutant 2 | 0.03 |
| Mutant 3 | 0.21 |
| Mutant 4 | 0.11 |
| Mutant 5 | 1.89 |
| Mutant 6 | 0.38 |
| Mutant 7 | 0.25 |
| Mutant 8 | 1.61 |
| Mutant 9 | 0.01 |
| Mutant 10 | 0.04 |
| Mutant 11 | 1.70 |

The capacity of chimeric L3D10 and the humanized antibodies mAb4 and mAb5 to bind the immobilized CTLA-4Fc mutant constructs was then determined by ELISA in which plates were coated with the CTLA-4 mutant proteins at 1 μg/mL and biotinylated anti-CTLA-4 antibodies, or B7-1 Ig control protein, were added and binding measured using HRP-conjugated streptavidin. The results of binding assays are shown in Tables 2-5. As expected, all 4 binding proteins demonstrated nice dose-dependent binding for the WT CTLA-4Fc protein. However, mutations that were introduced into the M9 and M10 proteins appear to alter the overall structure and these mutants failed to bind 17-1Fc. Mutations introduced in M2 and M4 also partially altered CTLA-4 conformation as indicated by reduced binding relative to the WT protein. Consistent with this notion, all 4 of these mutants (M2, M4, M9 and M10) were expressed at much lower yield (Table 1). In contrast, using binding to the WT CTLA-4Fc protein and binding of the B7-1 Fc proteins as references, M11 clearly stands out as a protein that is expressed well, binds B7-1Fc efficiently but failed to bind two humanized anti-CTLA-4 antibodies. Its binding to original L3D10 is also reduced by approximately 100-fold (Table 3). As expected, the mutations that affect the overall conformation also affected the binding to the anti-CTLA-4 antibodies.

TABLE 2

Integrity of CTLA-41g mutants as indicated by their binding to B7-1 Ig fusion protein. Binding to CT1A-4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins.

| Protein Conc. | WT | M1 | M2 | M3 | M4 | M5 | M6 | M7 | M8 | M9 | M10 | M11 |
|---|---|---|---|---|---|---|---|---|---|---|---|---|
| 0 | 0.193 | 0.196 | 0.202 | 0.184 | 0.182 | 0.182 | 0.184 | 0.185 | 0.18 | 0.172 | 0.175 | 0.174 |
| 0 | 0.19 | 0.182 | 0.177 | 0.175 | 0.171 | 0.171 | 0.173 | 0.17 | 0.168 | 0.164 | 0.162 | 0.163 |
| 10 ng/ml | 0.259 | 0.328 | 0.204 | 0.267 | 0.199 | 0.286 | 0.255 | 0.218 | 0.293 | 0.166 | 0.167 | 0.22 |
| 10 ng/ml | 0.257 | 0.311 | 0.187 | 0.249 | 0.184 | 0.271 | 0.244 | 0.22 | 0.276 | 0.154 | 0.159 | 0.217 |
| 100 ng/ml | 1.137 | 1.594 | 0.316 | 1.087 | 0.359 | 1.513 | 1.093 | 0.785 | 1.468 | 0.164 | 0.164 | 0.884 |
| 100 ng/ml | 1.111 | 1.553 | 0.299 | 1.082 | 0.34 | 1.221 | 1.049 | 0.695 | 1.375 | 0.155 | 0.15 | 1.045 |

TABLE 2-continued Integrity of CTLA-41g mutants as indicated by their binding to B7-1 Ig fusion protein. Binding to CT1A-4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins.

| Protein Conc. | WT | M1 | M2 | M3 | M4 | M5 | M6 | M7 | M8 | M9 | M10 | M11 |
|---|---|---|---|---|---|---|---|---|---|---|---|---|
| 1 ug/ml | 2.813 | 3.147 | 1.179 | 3.147 | 1.375 | 2.877 | 3.053 | 2.703 | 3.253 | 0.199 | 0.171 | 3.053 |
| 1 ug/ml | 2.651 | 3.053 | 0.986 | 2.864 | 1.413 | 3.025 | 2.983 | 2.716 | 2.93 | 0.218 | 0.172 | 3.159 |

TABLE 3

Epitope mapping of chimeric L3D10 antibody. Binding to CTLA-4Fc proteins was performed by ELISA, with the amounts of biotinylated protein bound measured by horse-radish peroxidase (HRP)-conjugated streptavidin. Values shown are the OD450 measurements, WT = wild type CTLA-4Fc. M1-M11 are CTLA-4Fc mutant proteins

| Protein Conc. | WT | M1 | M2 | M3 | M4 | M5 | M6 | M7 | M8 | M9 | M10 | M11 |
|---|---|---|---|---|---|---|---|---|---|---|---|---|
| 0 | 0.202 | 0.196 | 0.2 | 0.187 | 0.184 | 0.189 | 0.192 | 0.198 | 0.187 | 0.179 | 0.179 | 0.183 |
| 0 | 0.195 | 0.187 | 0.185 | 0.18 | 0.176 | 0.176 | 0.176 | 0.176 | 0.17 | 0.166 | 0.166 | 0.167 |
| 10 ng/ml | 1.433 | 2.47 | 0.375 | 0.62 | 0.507 | 1.539 | 1.033 | 0.714 | 1.233 | 0.18 | 0.18 | 0.202 |
| 10 ng/ml | 1.518 | 2.432 | 0.317 | 0.587 | 0.356 | 1.366 | 0.976 | 0.738 | 1.237 | 0.171 | 0.169 | 0.203 |
| 100 ng/ml | 3.053 | 3.253 | 1.384 | 2.318 | 2.142 | 2.841 | 2.699 | 2.495 | 2.909 | 0.295 | 0.215 | 0.635 |
| 100 ng/ml | 3.025 | 3.239 | 1.164 | 2.354 | 1.409 | 2.991 | 2.771 | 2.483 | 2.841 | 0.304 | 0.216 | 0.759 |
| 1 ug/ml | 3.373 | 3.268 | 2.387 | 3.184 | 2.651 | 3.025 | 3.092 | 3.147 | 3.136 | 0.916 | 0.804 | 2.841 |
| 1 ug/ml | 3.114 | 2.967 | 2.619 | 3.124 | 2.659 | 3.034 | 3.072 | 2.991 | 3.034 | 0.916 | 0.868 | 2.983 |

TABLE 4

Epitope mapping of humanized antibody mAb4. Binding to CTLA-4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins

| Protein Cone. | WT | M1 | M2 | M3 | M4 | M5 | M6 | M7 | M8 | M9 | M10 | M11 |
|---|---|---|---|---|---|---|---|---|---|---|---|---|
| 10 ng/ml | 0.312 | 2.264 | 0.207 | 0.198 | 0.194 | 0.407 | 0.22 | 0.194 | 0.247 | 0.177 | 0.181 | 0.172 |
| 10 ng/ml | 0.29 | 2.297 | 0.184 | 0.178 | 0.174 | 0.378 | 0.202 | 0.185 | 0.222 | 0.154 | 0.16 | 0.164 |
| 100 ng/ml | 1.077 | 2.827 | 0.203 | 0.27 | 0.219 | 1.371 | 0.459 | 0.281 | 0.725 | 0.171 | 0.17 | 0.172 |
| 100 ng/ml | 0.841 | 3.061 | 0.194 | 0.264 | 0.208 | 1.589 | 0.42 | 0.277 | 0.801 | 0.154 | 0.155 | 0.159 |
| 1 ug/ml | 2.51 | 2.881 | 0.339 | 0.882 | 0.473 | 2.79 | 1.992 | 1.169 | 2.33 | 0.175 | 0.17 | 0.178 |
| 1 ug/ml | 2.471 | 2.958 | 0.263 | 1.121 | 0.573 | 2.795 | 2.016 | 1.243 | 2.642 | 0.167 | 0.169 | 0.185 |

TABLE 5

Epitope mapping of humanized antibody mAb5. Binding to CTLA-4Fc proteins was performed by ELISA, with the amounts of biotinylated protein bound measured by horse-radish peroxidase (HRP)-conjugated streptavidin. Values shown are the OD450 measurements. WT = wild type CTLA-4Fc. M1-M11 are CTLA-4Fc mutant proteins

| Protein Conc. | WT | M1 | M2 | M3 | M4 | M5 | M6 | M7 | M8 | M9 | M10 | M11 |
|---|---|---|---|---|---|---|---|---|---|---|---|---|
| 10 ng/ml | 0.597 | 2.307 | 0.195 | 0.544 | 0.189 | 1.239 | 0.603 | 0.19 | 0.5 | 0.373 | 0.169 | 0.157 |
| 10 ng/ml | 0.535 | 2.244 | 0.162 | 0.195 | 0.435 | 1.188 | 0.516 | 0.535 | 0.47 | 0.148 | 0.15 | 0.152 |
| 100 ng/ml | 1.947 | 2.632 | 0.182 | 0.389 | 0.248 | 2.601 | 1.296 | 0.521 | 2.001 | 0.15 | 0.15 | 0.152 |
| 100 ng/ml | 2.229 | 2.186 | 0.175 | 0.364 | 0.221 | 2.425 | 0.875 | 0.405 | 2 | 0.137 | 0.139 | 0.148 |
| 1 ug/ml | 2.724 | 2.05 | 0.259 | 1.662 | 0.725 | 2.654 | 2.355 | 1.418 | 2.548 | 0.157 | 0.151 | 0.162 |
| 1 ug/ml | 2.742 | 2.297 | 0.274 | 1.549 | 0.724 | 2.84 | 2.374 | 1.369 | 2.69 | 0.147 | 0.143 | 0.165 |

TABLE 6

Raw data from a repeat study showing specific loss of antigenic epitope only in M11. As in Tables 2-5, except that additional controls were included to shown specificity of the binding.

| | Ab Conc | HCTLA4-Fc | M1 | M2 | M3 | M4 | M5 | M6 | M7 | M8 | M9 | M10 | M11 |
|---|---|---|---|---|---|---|---|---|---|---|---|---|---|
| Biotin- | 0 | 0.18 | 0.187 | 0.377 | 0.183 | 0.22 | 0.177 | 0.183 | 0.186 | 0.368 | 0.15 | 0.215 | 0.171 |
| LD310 | 0 | 0.177 | 0.222 | 0.538 | 0.167 | 0.18 | 0.229 | 0.177 | 0.142 | 0.217 | 0.293 | 0.114 | 0.155 |
| | 10 ng/ml | 1.705 | 2.692 | 0.469 | 0.623 | 0.817 | 1.853 | 1.244 | 0.837 | 1.27 | 0.158 | 0.169 | 0.19 |
| | 10 ng/ml | 1.799 | 2.779 | 0.333 | 0.593 | 0.583 | 1.802 | 1.331 | 0.884 | 1.454 | 0.213 | 0.157 | 0.194 |
| | 100 ng/ml | 3.316 | 3.195 | 1.313 | 2.244 | 2.233 | 3.251 | 3.032 | 2.672 | 3.015 | 0.419 | 0.26 | 0.752 |
| | 100 ng/ml | 3.458 | 3.567 | 1.37 | 2.535 | 2.356 | 3.316 | 3.032 | 2.875 | 3.157 | 0.346 | 0.272 | 0.746 |
| | 1000 ng/ml | 3.567 | 3.509 | 2.833 | 3.333 | 3.08 | 3.413 | 3.282 | 3.299 | 3.352 | 1.124 | 0.945 | 2.888 |
| | 1000 ng/ml | 3.672 | 3.509 | 2.755 | 3.299 | 3.145 | 3.537 | 3.316 | 3.352 | 3.435 | 1.161 | 0.941 | 2.914 |

TABLE 6-continued

Raw data from a repeat study showing specific loss of antigenic epitope only in M11. As in Tables 2-5, except that additional controls were included to shown specificity of the binding.

| | | | | | | | | | | | | | |
|---|---|---|---|---|---|---|---|---|---|---|---|---|---|
| Biotin-hB7-1 | 0 | 0.196 | 0.2 | 0.202 | 0.193 | 0.192 | 0.197 | 0.195 | 0.198 | 0.192 | 0.186 | 0.185 | 0.186 |
| | 0 | 0.192 | 0.185 | 0.181 | 0.192 | 0.178 | 0.178 | 0.178 | 0.187 | 0.173 | 0.169 | 0.168 | 0.161 |
| | 10 ng/ml | 0.316 | 0.37 | 0.216 | 0.304 | 0.22 | 0.345 | 0.279 | 0.258 | 0.326 | 0.177 | 0.176 | 0.239 |
| | 10 ng/ml | 0.31 | 0.356 | 0.21 | 0.414 | 0.26 | 0.331 | 0.279 | 0.253 | 0.297 | 0.159 | 0.167 | 0.236 |
| | 100 ng/ml | 1.581 | 1.882 | 0.333 | 1.245 | 0.527 | 1.813 | 1.235 | 0.899 | 1.557 | 0.176 | 0.172 | 1.092 |
| | 100 ng/ml | 1.525 | 1.928 | 0.323 | 1.345 | 0.489 | 1.735 | 1.385 | 0.987 | 1.643 | 0.162 | 0.155 | 1.283 |
| | 1000 ng/ml | 3.76 | 3.6 | 1.167 | 3.435 | 1.973 | 3.316 | 3.413 | 3.101 | 3.635 | 0.232 | 0.185 | 3.568 |
| | 1000 ng/ml | 3.6 | 3.673 | 1.316 | 3.51 | 2.009 | 3.459 | 3.413 | 3.183 | 3.635 | 0.215 | 0.181 | 3.673 |
| Biotin-mAb4 | 10 ng/ml | 0.451 | 2.812 | 0.207 | 0.202 | 0.194 | 0.626 | 0.23 | 0.207 | 0.327 | 0.197 | 0.205 | 0.181 |
| | 10 ng/ml | 0.417 | 2.693 | 0.181 | 0.179 | 0.177 | 0.642 | 0.22 | 0.195 | 0.32 | 0.158 | 0.182 | 0.162 |
| | 100 ng/ml | 1.868 | 3.568 | 0.212 | 0.29 | 0.256 | 2.618 | 0.589 | 0.345 | 1.532 | 0.172 | 0.174 | 0.171 |
| | 100 ng/ml | 1.938 | 3.317 | 0.203 | 0.274 | 0.247 | 2.126 | 0.571 | 0.305 | 1.419 | 0.155 | 0.155 | 0.162 |
| | 1000 ng/ml | 2.99 | 3.568 | 0.268 | 1.181 | 0.712 | 2.922 | 2.187 | 1.329 | 2.817 | 0.181 | 0.17 | 0.177 |
| | 1000 ng/ml | 3.033 | 3.51 | 0.266 | 1.184 | 0.759 | 3.071 | 2.358 | 1.475 | 2.869 | 0.144 | 0.171 | 0.187 |
| Biotin-mAb5 | 10 ng/ml | 0.983 | 2.654 | 0.202 | 0.218 | 0.197 | 1.409 | 0.429 | 0.218 | 0.727 | 0.176 | 0.176 | 0.17 |
| | 10 ng/ml | 0.955 | 2.604 | 0.184 | 0.2 | 0.168 | 1.359 | 0.389 | 0.21 | 0.761 | 0.148 | 0.154 | 0.152 |
| | 100 ng/ml | 2.669 | 3.007 | 0.232 | 0.534 | 0.319 | 2.906 | 1.839 | 0.523 | 2.669 | 0.145 | 0.161 | 0.16 |
| | 100 ng/ml | 2.741 | 3.158 | 0.203 | 0.554 | 0.374 | 2.895 | 1.741 | 0.478 | 2.604 | 0.145 | 0.148 | 0.157 |
| | 1000 ng/ml | 3.183 | 3.146 | 0.327 | 1.837 | 1.019 | 2.966 | 2.817 | 1.72 | 3.042 | 0.173 | 0.163 | 0.174 |
| | 1000 ng/ml | 3.209 | 3.316 | 0.321 | 1.867 | 1.015 | 3.196 | 2.857 | 1.766 | 3.051 | 0.143 | 0.163 | 0.187 |

| Ab conc | Biotin-L3D10 mCTLA4-Fc | Biotin-L3D10 hIg-Fc | Biotin-hB7-1 mCTLA4-Fc | Biotin-hB7-1 hIg-Fc | Biotin-HL12 | Biotin-HL12 | Biotin-HL32 | |
|---|---|---|---|---|---|---|---|---|
| 0 | 0.19 | 0.198 | 0.202 | 0.191 | | | | |
| 0 | 0.189 | 0.184 | 0.16 | 0.185 | | | | |
| 10 ng/ml | 0.201 | 0.201 | 0.338 | 0.181 | 0.179 | 0.188 | 0.185 | 0.179 |
| 10 ng/ml | 0.18 | 0.182 | 0.318 | 0.164 | 0.165 | 0.162 | 0.17 | 0.181 |
| 100 ng/ml | 0.303 | 0.315 | 1.635 | 0.176 | 0.171 | 0.177 | 0.185 | 0.176 |
| 100 ng/ml | 0.314 | 0.326 | 1.668 | 0.165 | 0.162 | 0.163 | 0.166 | 0.171 |
| 1000 ng/ml | 0.942 | 1.365 | 3.569 | 0.18 | 0.177 | 0 182 | 0.184 | 0.183 |
| 1000 ng/ml | 0.94 | 1.475 | 3.353 | 0.179 | 0.172 | 0.177 | 0.176 | 0.187 |
| | mCTLA4 Biotin-L3D10 | hIgG | mCTLA4 Biotin-hB7-1 | hIgG | mCTLA4 Biotin-HL12 | hIgG | mCTLA4 Biotin-HL32 | hIgG |

Since L3D10 retained significant binding the M11, we tested if the binding is specific. We coated plate with human CTLA-4-Fc (hCTLA-4Fc), mouse CTLA-4-Fc (mCTLA-4-Fc). Control IgG1-Fc or all mutant hCTLA-4-Fc and measured their binding to B7-1Fc along with L3D10, mAb4 and mAb5. The bulk of the data are presented in Table 6. As shown in FIG. 17, biotinylated B7-1 binds hCTLA-4, mCTLA-4 and M11, equally well. The specificity of the assay is demonstrated by lack of binding to IgG1-Fc. Interesting, while L3D10-binding to M11 is stronger than those to IgG1-Fc and mCTLA-4-Fc, significant binding to IgG1-Fc suggest that the chimeric antibody binding to M11 maybe nonspecific. In contrast, none of the humanized antibodies bind to M11, mCTLA-4, and IgG1-Fc control. These data demonstrate that mutations introduced in M11 selectively ablated L3D10, mAb4 and mAb5 binding to CTLA-4.

Using known complex structure 133, we mapped the CTLA-4 epitope in a 3-D structure. As shown in FIG. 18, the epitope recognized by these mAbs localized within the area covered by B7-1. As such, L3D10, mAb4 and mAb5 binding to CTLA-4 would be mutually exclusive to that of B7-1. The poor blocking of mAb4 and mAb5 is due to lower avidity rather than distinctive binding domains.

Using a number of mutants of the human CTLA-4Fc protein in which clusters of amino acids from the human CTLA-4 protein were replaced with amino acids from the murine Ctla-4 protein, we clearly demonstrate that when we replace 4 amino acids that immediately follow the known B7-1 binding domain of CTLA-4, MYPPPY, dose-dependent binding of the antibodies is largely abolished. The fact that the binding epitope maps directly adjacent to the B7-1 binding domain correlates well with the demonstrated ability of the L3D10 antibodies to block B7-CTLA-4 interactions both in vitro and in vivo.

Example 7

Generation of Fusion Proteins that Show Diminished Binding to One or More Cancer Immunotherapeutic Anti-CTLA-4 mAbs We have generated a panel of 17 CTLA-4-Fc fusion proteins with various mutations, designated M1-M17 (SEQ ID NOS: 7-23), which include the 11 proteins identified in Example 10 (FIG. 16) plus 6 additional mutants (FIG. 19). Further mutations were made to M17. The new mutants are called M17-1, M17-2, M17-3 and M17-4 (SEQ ID NOS: 42-45). These mutations were generated anticipating that they would ablate binding to a broad spectrum of anti-CTLA-4 antibodies but retain binding to the CTLA-4 ligands, CD80 (B7-1) and CD86 (B7-2). As the first step, we coated a given concentration of the fusion proteins on the plate and added biotinylated B7-1Fc. As shown in FIGS. 20A and B, all but 2 fusion proteins (M9 and M10) retain binding to B7-1, although a significant reduction in B7-1 binding was found in M2, M4 and M7. Since these proteins are functionally less active, it is unlikely that these mutants are optimal for in vivo protection against autoimmune adverse effects. Additional data demonstrate that M15, M17, M17-1 and M17-2 retained strong binding to both CD80 and CD86 (FIG. 21).

Next, we evaluated if these mutant proteins (M1-M17, and M17-1 to M17-4) have lost binding to anti-CTLA4 mAbs that are either approved for clinical use or being developed for clinical therapy. A total of 4 mAbs were tested. For mAb1 (Ipilimumab), fusion proteins M11, M13, M15, M17, M17-1, M17-2 and M17-3 have lost binding, and thus can be used for protection against autoimmune diseases induced by this mAb (FIG. 22A). For autoimmune diseases induced by mAb2 (Tremelimumab), M15. M17. M17-2 and M17-3 will be effective (FIG. 22B). For mAb4 and mAb5, M1, M12, M14, and M16 are likely the most effective, although M3 and M17 may also work (FIGS. 23, 24 and 25).

Therefore, as summarized in Table 7, CTLA4-Fc fusion protein M17 has broad spectrum activity for use in protection against autoimmune diseases induced by anti-CTLA4 antibodies. M17-3 shows low binding to anti-CTLA4 antibodies but low binding to 137-1 and B7-2. However, M17-2 showed better binding to B7-1 and B7-2 and yet shows acceptably low cross-reactivity against a broad range of anti-human CTLA-4 mAbs.

TABLE 7

Identification of CTLA4-Fc fusion proteins that retains binding to B7-1, but not to anti-CTLA4 mAb. Relative binding is presented by " +" or "—", where "++++" is the strongest binding and "—" indicates no binding. ND = not determined.

| CTLA4-Fc Fusion protein | hB7-1Fc | hB7-2Fc | mAb1 (Ipilimumab) | mAb2 (Tremelimumab) | mAb4 | mAb5 |
|---|---|---|---|---|---|---|
| abatacept | +++ | ND | +++ | +++ | +++ | +++ |
| hIgGFc ctl | — | — | — | — | — | — |
| M1 | +++ | ND | +++ | ND | ++++ | ++++ |
| M2 | + | ND | + | ND | — | — |
| M3 | +++ | ND | +++ | ND | + | + |
| M4 | + | ND | + | ND | + | + |
| M5 | +++ | ND | +++ | ND | +++ | +++ |
| M6 | +++ | ND | +++ | ND | + | ++ |
| M7 | ++ | ND | + | ND | + | + |
| M8 | +++ | ND | +++ | ND | +++ | +++ |
| M9 | — | ND | — | ND | — | — |
| M10 | — | ND | — | ND | — | — |
| M11 | +++ | ND | — | +++ | — | — |
| M12 | +++ | ND | + | +++ | — | — |
| M13 | +++ | ND | — | +++ | ++ | ++ |
| M14 | +++ | ND | + | +++ | — | — |
| M15 | +++ | +++ | — | — | +++ | ++++ |
| M16 | +++ | ND | + | +++ | — | — |
| M17 | +++ | ++ | — | — | + | + |
| M17-1 | +++ | ++ | — | +++ | ++ | — |
| M17-2 | +++ | +++ | — | — | +/− | — |
| M17-3 | ++ | +/− | — | — | — | — |
| M17-4 | +++ | + | + | +++ | ++ | — |

Example 8

Blocking B7-1 and B7-2 does not Prevent Immunotherapeutic Effect of Ipilimumab

A critical requirement for treating anti-CTLA-4-immunotherapy related adverse effects with CTLA-4-Fc mutants that bind to B7-1/B7-2 is that blocking 17-1 and B7-2 does not affect the immunotherapeutic effect. Since mice with targeted mutations of Cd80 (encoding B7-1) and Cd86 (encoding B7-2) do not have Treg (17) and thus express very little Ctla4, we tested this prediction by using a saturating dose of anti-B7-1 (1G10) and anti-B7-2 (GL-1) mAbs, which block the binding of human CTLA-4 to mB7-1 and mB7-2, respectively (FIG. 26A). As diagrammed in FIG. 26B, we treated MC38 tumor-bearing mice with Ipilimumab in conjunction with either control Ig or a combination of anti-mB7-1 and anti-mB7-2 mAbs. The anti-mB7 mAbs used completely masked all 87-1 and B7-2 in the PBL as their binding to new anti-mB7 mAb is reduced to what was observed in mice with targeted mutations of both Cd80 and Cd86 (dKO) (FIG. 26C, D). Functional blockade of 137 by anti-137-1 and anti-B7-2 mAbs was evaluated using sera collected at day 22 after tumor challenge to evaluate anti-human IgG antibody response and confirmed by the fact that antibody response against Ipilimumab was abrogated (FIG. 26E). Importantly, saturating blockade of mB7 did not affect the Ipilimumab-induced tumor rejection as anti-mB7 and control Ig treated mice are equally responsive to Ipilimumab (FIG. 26F). These data indicate that anti-B7-1 and anti-87-2 as well as B7-binding CTLA-4 fusion proteins that do not bind anti-CTLA-4 antibodies can be used to treat irAE associated with anti-CTLA-4 immunotherapy, while leaving the protective immunotherapeutic activity intact.

Example 9

Use of CTLA-4 Fusion Proteins to Treat Autoimmune Adverse Effects Associated with Anti-CTLA-4 and Anti-PD-1 Combination Therapy Combination therapy with anti-CTLA-4 and anti-PD-1 represents the most effective cancer immunotherapy. However, with greater than 50% of patients receiving immunotherapy developing irAEs, there is an urgent need to develop therapeutic approaches to treat or prevent irAE. As demonstrated in Example 8, the immunotherapeutic effect of Ipilimumab (mAb1) is unaffected by the blockade of B7-1 and B7-2. These findings prompted us to test if mutant CTLA-4Fc can be used to treat irAE associated with Ipilimumab+ anti-PD-1 combination therapy. Since Ipilimumab does not bind to CTLA-4-Fc fusion proteins M11 or M15 (belatacept), we tested to see if co-administration of belatacept or M11 or M15 can ameliorate irAE, using retarded growth as a readout of irAE (see Example 2). As shown in FIG. 27, low doses of either M1 (100 μg/injection) or M15 (200 μg/injection) prevented irAE. In addition to M11 and M15, other proteins with similar properties, including M13. M16 and M17 may also be used.

Example 10

Identification of Fusion Proteins that do not Interfere with Anti-CTLA4 Immunotherapeutic Activity In order to determine whether CTLA-4-Fc fusion proteins interfere with anti-CTLA4 immunotherapeutic effects, we injected MC38-tumor bearing mice with either control IgG Fc (200 sg/injection) or Ipilimumab (100 μg/injection) in combination with control IgGFc (100 sig/injection) or the CTLA4 fusion proteins, Abetacept, M15 or M17 (100 μg/injection) on days 7, 10, 13 and 17. The tumor growth rate were shown in FIG. 28A, while the mouse survival to early removal endpoint are shown in FIG. 28B. As expected, Abatacept ablated the immunotherapeutic effect of the Ipilimumab. In contrast, M15 and M17 did not interfere with the therapeutic effect of Ipilimumab.

Example 11

Modulation of T Cell Activation and its Associated Adverse Effect in NSG Mice Reconstituted with Human Hematopoietic System To determine the impact of CTLA-4 fusion proteins on the activation of human T cells and associated irAE in vivo, we reconstituted the 3 week old NSG mice with human hematopoetic stem cells and monitored T cell activation. As shown in FIGS. 29-32, different CTLA-4 mAbs appear to have different effects on T cell phenotype and the adverse effects of Ipilimumab. Thus, as shown in FIG. 29A, treatment with Ipilimumab prevents NSG mice from gaining weight, and this is prevented by co-administration of M15 or M17-2. Interestingly, M15 induced elevation of Alanine transaminase when used in conjunction with Ipilimumab (FIG. 29B). These data suggest that M15 may induce liver damage when used in conjunction with Ipilimumab. Importantly, no such effect was observed when M17-2 was used in conjunction with M15.

To understand the immunological basis of the differentiation between M15 and M17, we sacrificed the NSG mice on day 31 and analyzed the composition of T cell subsets. As shown in FIG. 30, M17 induced more central memory T cells, while reducing effector T cells. The reduction of effector T cells may explain the reduced adverse effect as this is the subset that migrates into organs to cause immune destruction. Furthermore, since NKT cells are the primary mediator of hepatitis, we compared M15 and M17-2 for their impact on NKT cells, based on expression of both CD56 and CD3. As shown in FIG. 31, M17-2 reduced the number of NKT while M15 enhanced it.

The regulatory T cells suppress autoimmune diseases and cancer immunity. It is therefore desirable to reduce Treg to enhance cancer immunity. However, if the reduction is too severe, one may induce autoimmune disease. Consistent with a critical role for B7-CD28 interactions in the generation and maintenance of Treg in mice, both M15 and M17-2 significantly reduced the % of Treg (FIGS. 32A and B). However, M15 is much more effective in reducing Treg (FIGS. 32A and B). Furthermore, Treg from M15-treated mice had substantially lower CTLA-4 (FIGS. 32C and D). Given the essential role for CTLA-4 in Treg function in vivo, it is likely that Treg from the M15-treated mice are functionally impaired. Thus, a severe reduction of Treg combined with selective reduction of CTLA-4 protein levels suggest an intriguing possibility that M15 may induce autoimmune destruction when used in conjunction Ipilimumab.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES CITED

10. Leach D R, Krummel M F, Allison J P. Enhancement of antitumor immunity by CTLA-4 blockade [see comments]. Science. 1996; 271(5256):1734-6.
108 Guinan, E. C. et al. Transplantation of anergic histoincompatible bone marrow allografts. N. Engl. J. Med. 340, 1704-1714, doi:10.1056/NEJM199906033402202 (1999).
128 Magistrelli, G. et al. A soluble form of CTLA-4 generated by alternative splicing is expressed by nonstimulated human T cells. Eur. J. Immunol. 29, 3596-3602, doi:10.1002/(SICI)1521-4141(199911)29:11<3596::AID-IMMU3596>3.0.CO;2-Y (1999).
64 Ueda, H. et al. Association of the T-cell regulatory gene CTLA-4 with susceptibility to autoimmune disease. Nature 423, 506-511 (2003).
129 Kremer, J. M. et al. Treatment of rheumatoid arthritis by selective inhibition of T-cell activation with fusion protein CTLA-4Ig. N. Engl. J. Med. 349, 1907-1915, doi: 10.1056/NEJMoa035075 (2003).
130 Abrams, J. R. et al. CTLA-4Ig-mediated blockade of T-cell costimulation in patients with psoriasis vulgaris. J. Clin. Invest. 103, 1243-1252, doi:10.1172/JCI5857 (1999).
131 Gerold, K. D. et al. The soluble CTLA-4 splice variant protects from type I diabetes and potentiates regulatory T-cell function. Diabetes 60, 1955-1963, doi:10.2337/db11-0130 (2011).
132 Peach, R. J. et al. Complementarity determining region 1 (CDR1)- and CDR3-analogous regions in CTLA-4 and CD28 determine the binding to B7-1. J. Exp. Med. 180, 2049-2058 (1994).
1. Townsend A R M, Tothbard J. Gotch F M, Bahadur G, Wraith D, McMichael A L. The epitope of influenza nucleoprotein recognized by cytotoxic lymphocytes can be defined with short synthetic peptides. Cell. 1986; 44:959-68.
2. Zinkernagel R M, Doherty P C. Restriction of in vitro T cell-mediated cytotoxicity in lymphocytic choriomeningitis within a syngeneic or semiallogeneic system. Nature. 1974; 248:701-2.

3. Lafferty K J, Prowse S J, Simeonovic C J, Warren H S. Immunobiology of tissue transplantation: a return to the passenger leukocyte concept. Annu Rev Immunol. 1983; 1:143-73.
4. Liu Y, Linsley P S. Costimulation of T-cell growth. Curr Opin Immunol. 1992; 4(3):265-70.
5. Schwartz R H. Costimulation of T lymphocytes: the role of CD28. CTLA-4, and B7/BB1 in interleukin-2 production and immunotherapy. Cell. 1992; 71(7):1065-8.
6. Freeman G J, Freedman A S, Segil J M, Lee G, Whitman J F, Nadler L M. B7, a new member of the Ig superfamily with unique expression on activated and neoplastic B cells. J Immunol. 1989; 143(8):2714-22.
7. Freeman G J, Gribben J G, Boussiotis V A, Ng J W, Restivo V A, Jr., Lombard L A, et al. Cloning of B7-2: a CTLA-4 counter-receptor that costimulates human T cell proliferation [see comments]. Science. 1993; 262(5135): 909-11.
8. Hathcock K S, Laszlo G. Dickler H B, Bradshaw J, Linsley P, Iodes R J. Identification of an alternative CTLA-4 ligand costimulatory for T cell activation [see comments]. Science. 1993; 262(5135):905-7.
9. Wu Y, Guo Y, Liu Y. A major costimulatory molecule on antigen-presenting cells. CTLA-4 ligand A, is distinct from B7. J Exp Med. 1993; 178(5):1789-93.
10. Leach D R, Krummel M F, Allison J P. Enhancement of antitumor immunity by CTLA-4 blockade [see comments]. Science. 1996:271(5256):1734-6.
11. Linsley P S, Brady W, Urnes M, Grosmaire L S, Damle N K, Ledbetter J A. CTLA-4 is a second receptor for the B cell activation antigen B7. J Exp Med. 1991; 174(3): 561-9.
12. Linsley P S, Clark E A, Ledbetter J A. T-cell antigen CD28 mediates adhesion with B cells by interacting with activation antigen B7/BB-1. Proc Natl Acad Sci USA. 1990; 87(13):5031-5.
21. May K F, Roychowdhury S, Bhatt D. Kocak E, Bai X F, Liu J Q, et al. Anti-human CTLA-4 monoclonal antibody promotes T cell expansion and immunity in a hu-PBL-SCID model: a new method for preclinical screening of costimulatory monoclonal antibodies. Blood. 2005; 105: 1114-20. PubMed PMID: 15486062.
20. Lute K D, May K F, Lu P, Zhang H. Kocak E, Mosinger B, et al. Human CTLA-4-knock-in mice unravel the quantitative link between tumor immunity and autoimmunity induced by anti-CTLA-4 antibodies. Blood. 2005. PubMed PMID: 16037385.
49. Keler, T. et al. Activity and safety of CTLA-4 blockade combined with vaccines in cynomolgus macaques. J. Immunol. 171, 6251-6259 (2003).
50. Wing. K. et al. CTLA-4 control over Foxp3+ regulatory T cell function. Science 322, 271-275, doi:10.1126/science.1160062 (2008).
66. Qureshi, O. S. et al. Trans-endocytosis of CD80 and CD86: a molecular basis for the cell-extrinsic function of CTLA-4. Science 332, 600-603, doi:10.1126/science.1202947 (2011).
30. Walunas, T. L., et al., CTLA-4 can function as a negative regulator of T cell activation. Immunity, 1994. 1(5): p. 405-13.
31. Krummel, M. F. and J. P. Allison, CD28 and CTLA-4 have opposing effects on the response of T cells to stimulation. J Exp Med, 1995. 182(2): p. 459-65.
52. Simpson, T. R. et al. Fc-dependent depletion of tumor-infiltrating regulatory T cells co-defines the efficacy of anti-CTLA-4 therapy against melanoma. J. Exp. Med. 210, 1695-1710. doi:10.1084/jem.20130579 (2013).
55. Korman. A. J., Peggs, K. S. & Allison, J. P. Checkpoint blockade in cancer immunotherapy. Adv. Immunol. 90, 297-339, doi:10.1016/S0065-2776(06)90008-X (2006).
56. Ribas, A. et al. Tremelimumab (CP-675,206), a cytotoxic T lymphocyte associated antigen 4 blocking monoclonal antibody in clinical development for patients with cancer. Oncologist 12, 873-883, doi:10.1634/theoncologist.12-7-873 (2007).
57. Ribas, A. et al. Phase III randomized clinical trial comparing tremelimumab with standard-of-care chemotherapy in patients with advanced melanoma. J. Clin. Oncol. 31, 616-622, doi:10.1200/JCO.2012.44.6112 (2013).
58. Lee. K. M. et al. Molecular basis of T cell inactivation by CTLA-4 [In Process Citation]. Science 282, 2263-2266 (1998).
59. Marengere, L. E. et al. Regulation of T cell receptor signaling by tyrosine phosphatase SYP association with CTLA-4 [published errata appear in Science 1996 Dec. 6; 274(5293)1597 and 1997 Apr. 4; 276(5309):21]. Science 272, 1170-1173 (1996).
60. Liu, Y. Is CTLA-4 a negative regulator for T-cell activation? Immunol. Today 18, 569-572 (1997).
61. Tivol, E. A. et al. Loss of CTLA-4 leads to massive lymphoproliferation and fatal multiorgan tissue destruction, revealing a critical negative regulatory role of CTLA-4. Immunity 3, 541-547 (1995).
62. Waterhouse, P. et al. Lymphoproliferative disorders with early lethality in mice deficient in CTLA-4 [see comments]. Science 270, 985-988 (1995).
63. Bachmann, M. F., Kohler. G., Ecabert, B., Mak, T. W. & Kopf. M. Cutting edge: lymphoproliferative disease in the absence of CTLA-4 is not T cell autonomous. J. Immunol. 163, 1128-1131 (1999).
64. Bachmann, M. F. et al. Normal pathogen-specific immune responses mounted by CTLA-4-deficient T cells: a paradigm reconsidered. Eur. J. Immunol. 31, 450-458 (2001).
65. Nguyen, T. V., Ke, Y., Zhang. E. E. & Feng, G. S. Conditional deletion of Shp2 tyrosine phosphatase in thymocytes suppresses both pre-TCR and TCR signals. J. Immunol. 177, 5990-5996 (2006).
72 Peach R J, Bajorath J, Brady W, Leytze G, Greene J, Naemura J, et al. Complementarity determining region 1 (CDR1)- and CDR3-analogous regions in CTLA-4 and CD28 determine the binding to B7-1. J Exp Med. 1994; 180(6):2049-58.
17. Proietto A H, Lahoud M H, Wu L. Distinct functional capacities of mouse thymic and splenic dendritic cell populations. Immunol Cell Biol. 2008 November-December; 86(8):700-8. doi: 10.1038/icb.2008.63. Epub 2008 Sep. 9.

The invention claimed is:

1. A CTLA-4 protein comprising an extracellular domain of CTLA-4 comprising the sequence set forth in SEQ ID NO: 47.

2. The CTLA-4 protein of claim 1, wherein the CTLA-4 protein binds to at least one of B7-1 and B7-2.

3. The CTLA-4 protein of claim 2, wherein the CTLA-4 protein does not block the cancer immunotherapeutic effects of an anti-CTLA-4 antibody.

4. The CTLA-4 protein of claim 3, wherein the anti-CTLA-4 antibody is Ipilimumab.

5. The CTLA-4 protein of claim 1, wherein the extracellular domain of CTLA-4 is fused at its C-terminus to a Fc region of a human immunoglobulin protein.

6. The CTLA-4 protein of claim 5, wherein the human immunoglobulin protein is selected from the group consisting of IgG1, IgG4, and IgM.

7. The CTLA-4 protein of claim 6, comprising the sequence set forth in SEQ ID NO: 43.

8. A pharmaceutical composition comprising a therapeutically effective amount of the CTLA-4 protein of claim 1, and a physiologically acceptable carrier or excipient.

9. A method of treating adverse events associated with cancer immunotherapy in a subject in need thereof, comprising administering to the subject the CTLA-4 protein of claim 1.

10. The method of claim 9, wherein the extracellular domain of CTLA-4 is fused at its C-terminus to a Fc region of a human immunoglobulin protein selected from the group consisting of IgG1, IgG4, and IgM.

11. The method of claim 10, wherein the cancer immunotherapy comprises an anti-CTLA-4 antibody.

12. The method of claim 11, wherein the anti-CTLA-4 antibody is Ipilimumab.

13. The method of claim 12, wherein the cancer immunotherapy further comprises an anti-PD-1 antibody.

14. A CTLA-4 protein, wherein the amino acid sequence of the CTLA-4 protein consists of the sequence set forth in SEQ ID NO: 43.

15. A pharmaceutical composition comprising a therapeutically effective amount of the CTLA-4 protein of claim 14, and a physiologically acceptable carrier or excipient.

16. A method of treating adverse events associated with cancer immunotherapy in a subject in need thereof, comprising administering to the subject the CTLA-4 protein of claim 14.

17. The method of claim 16, wherein the cancer immunotherapy comprises an anti-CTLA-4 antibody.

18. The method of claim 17, wherein the anti-CTLA-4 antibody is Ipilimumab.

19. The method of claim 18, wherein the cancer immunotherapy further comprises an anti-PD-1 antibody.

20. The method of claim 16, wherein the subject has cancer.

* * * * *

SEQUENCE LISTING

<160> NUMBER OF SEQ ID NOS: 50

<210> SEQ ID NO 1
<211> LENGTH: 223
<212> TYPE: PRT
<213> ORGANISM: Homo sapiens

<400> SEQUENCE: 1

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 2
<211> LENGTH: 357
<212> TYPE: PRT
<213> ORGANISM: Homo sapiens

<400> SEQUENCE: 2

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
```

```
            100                 105                 110
Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
        210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
                275                 280                 285

Val Glu Trp Glu Ser Asn Gly Gln Pro Glu Asn Asn Tyr Lys Thr Thr
                290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
        355

<210> SEQ ID NO 3
<211> LENGTH: 126
<212> TYPE: PRT
<213> ORGANISM: Homo sapiens

<400> SEQUENCE: 3

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110
```

```
Gln Ile Tyr Val Ile Asp Pro Glu Pro Cys Pro Asp Ser Asp
            115                 120                 125

<210> SEQ ID NO 4
<211> LENGTH: 174
<212> TYPE: PRT
<213> ORGANISM: Homo sapiens

<400> SEQUENCE: 4

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Ala Lys Glu Lys Lys Pro Ser Tyr
145                 150                 155                 160

Asn Arg Gly Leu Cys Glu Asn Ala Pro Asn Arg Ala Arg Met
                165                 170

<210> SEQ ID NO 5
<211> LENGTH: 223
<212> TYPE: PRT
<213> ORGANISM: Mus musculus

<400> SEQUENCE: 5

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
                20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140
```

```
Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Ser Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220

<210> SEQ ID NO 6
<211> LENGTH: 126
<212> TYPE: PRT
<213> ORGANISM: Mus musculus

<400> SEQUENCE: 6

Glu Ala Ile Gln Val Thr Gln Pro Ser Val Leu Ala Ser Ser His
1               5                   10                  15

Gly Val Ala Ser Phe Pro Cys Glu Tyr Ser Pro Ser His Asn Thr Asp
                20                  25                  30

Glu Val Arg Val Thr Val Leu Arg Gln Thr Asn Asp Gln Met Thr Glu
                35                  40                  45

Val Cys Ala Thr Thr Phe Thr Glu Lys Asn Thr Val Gly Phe Leu Asp
    50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
                100                 105                 110

Gln Ile Tyr Val Ile Asp Pro Glu Pro Cys Pro Asp Ser Asp
                115                 120                 125

<210> SEQ ID NO 7
<211> LENGTH: 357
<212> TYPE: PRT
<213> ORGANISM: Artificial Sequence
<220> FEATURE:
<223> OTHER INFORMATION: Fusion protein

<400> SEQUENCE: 7

Ile Gln Val Thr Gln Pro Ser Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
                35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 8
<211> LENGTH: 357
<212> TYPE: PRT
<213> ORGANISM: Artificial Sequence
<220> FEATURE:
<223> OTHER INFORMATION: Fusion protein

<400> SEQUENCE: 8

Met His Val Ala Gln Pro Ala Val Val Leu Ala Ser Ser His Gly Leu
1               5                   10                  15

Ala Ser Phe Pro Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
                275                 280                 285

Val Glu Trp Glu Ser Asn Gly Gln Pro Glu Asn Asn Tyr Lys Thr Thr
                290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
            355

<210> SEQ ID NO 9
<211> LENGTH: 358
<212> TYPE: PRT
<213> ORGANISM: Artificial Sequence
<220> FEATURE:
<223> OTHER INFORMATION: Fusion protein

<400> SEQUENCE: 9

Met His Val Ala Gln Pro Ala Val Val Leu Ala Ser Ser Arg Gly Ile
1               5                   10                  15

Ala Ser Phe Val Cys Glu Tyr Ala Ser Pro Ser His Asn Thr Asp Glu
                20                  25                  30

Val Arg Val Thr Val Leu Arg Gln Ala Asp Ser Gln Val Thr Glu Val
                35                  40                  45

Cys Ala Ala Thr Tyr Met Met Gly Asn Glu Leu Thr Phe Leu Asp Asp
            50                  55                  60

Ser Ile Cys Thr Gly Thr Ser Ser Gly Asn Gln Val Asn Leu Thr Ile
65              70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val Ile Asp Pro Glu Pro Cys Pro Asp Ser Asp Gln Glu Pro
```

```
            115                 120                 125
Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 10
<211> LENGTH: 357
<212> TYPE: PRT
<213> ORGANISM: Artificial Sequence
<220> FEATURE:
<223> OTHER INFORMATION: Fusion protein

<400> SEQUENCE: 10

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Thr Asn Asp Gln Met Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
```

```
              115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
                210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
            355

<210> SEQ ID NO 11
<211> LENGTH: 357
<212> TYPE: PRT
<213> ORGANISM: Artificial Sequence
<220> FEATURE:
<223> OTHER INFORMATION: Fusion protein

<400> SEQUENCE: 11

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Phe Thr Glu Lys Asn Thr Val Gly Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 12
<211> LENGTH: 357
<212> TYPE: PRT
<213> ORGANISM: Artificial Sequence
<220> FEATURE:
<223> OTHER INFORMATION: Fusion protein

<400> SEQUENCE: 12

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Thr Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
```

```
                    115                 120                 125
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
        180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
        210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 13
<211> LENGTH: 357
<212> TYPE: PRT
<213> ORGANISM: Artificial Sequence
<220> FEATURE:
<223> OTHER INFORMATION: Fusion protein

<400> SEQUENCE: 13

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Tyr Pro
        50                  55                  60

Phe Cys Ser Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Glu Pro Lys
```

```
                115                 120                 125
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 14
<211> LENGTH: 357
<212> TYPE: PRT
<213> ORGANISM: Artificial Sequence
<220> FEATURE:
<223> OTHER INFORMATION: Fusion protein

<400> SEQUENCE: 14

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Phe Asn Glu Ser Arg Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
```

```
                115                 120                 125
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
        180                 185                 190

Glu Val His Asn Ala Lys Thr Lys Pro Arg Glu Glu Gln Tyr Asn Ser
    195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
        260                 265                 270

Val Ser Leu Thr Cys Leu Val Lys Gly Phe Tyr Pro Ser Asp Ile Ala
    275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
        340                 345                 350

Leu Ser Pro Gly Lys
        355

<210> SEQ ID NO 15
<211> LENGTH: 358
<212> TYPE: PRT
<213> ORGANISM: Artificial Sequence
<220> FEATURE:
<223> OTHER INFORMATION: Fusion protein

<400> SEQUENCE: 15

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Val Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Gln Glu Pro
```

```
            115                 120                 125
Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 16
<211> LENGTH: 358
<212> TYPE: PRT
<213> ORGANISM: Artificial Sequence
<220> FEATURE:
<223> OTHER INFORMATION: Fusion protein

<400> SEQUENCE: 16

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Met Asp Thr Gly Leu Tyr Leu Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Gln Glu Pro
```

```
                  115                 120                 125
Lys Ser Ser Asp Lys Thr His Thr Ser Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 17
<211> LENGTH: 357
<212> TYPE: PRT
<213> ORGANISM: artificial
<220> FEATURE:
<223> OTHER INFORMATION: Fusion protein

<400> SEQUENCE: 17

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
```

```
              115                 120                 125
Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 18
<211> LENGTH: 357
<212> TYPE: PRT
<213> ORGANISM: artificial
<220> FEATURE:
<223> OTHER INFORMATION: Fusion protein

<400> SEQUENCE: 18

Ile Gln Val Thr Gln Pro Ser Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Phe Thr Glu Lys Asn Thr Val Gly Phe Leu Asp Asp Ser
        50                  55                  60

Ile Cys Thr Gly Thr Phe Asn Glu Ser Arg Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 19
<211> LENGTH: 357
<212> TYPE: PRT
<213> ORGANISM: artificial
<220> FEATURE:
<223> OTHER INFORMATION: Fusion protein

<400> SEQUENCE: 19

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 20
<211> LENGTH: 357
<212> TYPE: PRT
<213> ORGANISM: Artificial Sequence
<220> FEATURE:
<223> OTHER INFORMATION: Fusion protein

<400> SEQUENCE: 20

Ile Gln Val Thr Gln Pro Ser Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Phe Thr Glu Lys Asn Thr Val Gly Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 21
<211> LENGTH: 357
<212> TYPE: PRT
<213> ORGANISM: Artificial Sequence
<220> FEATURE:
<223> OTHER INFORMATION: Fusion protein

<400> SEQUENCE: 21

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Lys Pro Lys Asp Thr
145                 150                 155                 160

Leu Met Ile Ser Arg Thr Pro Glu Val Thr Cys Val Val Val Asp Val
                    165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
        210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                    245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
        290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                    325                 330                 335

Val Met His Glu Ala Leu His Asn His Tyr Thr Gln Lys Ser Leu Ser
                340                 345                 350

Leu Ser Pro Gly Lys
            355

<210> SEQ ID NO 22
<211> LENGTH: 357
<212> TYPE: PRT
<213> ORGANISM: Artificial Sequence
<220> FEATURE:
<223> OTHER INFORMATION: Fusion protein

<400> SEQUENCE: 22

Ile Gln Val Thr Gln Pro Ser Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Phe Thr Glu Lys Asn Thr Val Gly Phe Leu Asp Asp Ser
        50                  55                  60

Ile Cys Thr Gly Thr Phe Asn Glu Ser Arg Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
```

```
                 115                 120                 125
Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
                275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
            355

<210> SEQ ID NO 23
<211> LENGTH: 357
<212> TYPE: PRT
<213> ORGANISM: Artificial Sequence
<220> FEATURE:
<223> OTHER INFORMATION: Fusion protein

<400> SEQUENCE: 23

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Glu Gly Met Gly Asn Gly Thr Gln Ile
                100                 105                 110

Tyr Val Ile Asp Pro Glu Pro Cys Pro Asp Ser Asp Gln Glu Pro Lys
```

```
            115                 120                 125
Ser Ser Asp Lys Thr His Thr Ser Pro Pro Ser Pro Ala Pro Glu Leu
    130                 135                 140

Leu Gly Gly Ser Ser Val Phe Leu Phe Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 24
<211> LENGTH: 124
<212> TYPE: PRT
<213> ORGANISM: Artificial Sequence
<220> FEATURE:
<223> OTHER INFORMATION: Mutant

<400> SEQUENCE: 24

Ile Gln Val Thr Gln Pro Ser Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
```

```
            115                 120

<210> SEQ ID NO 25
<211> LENGTH: 124
<212> TYPE: PRT
<213> ORGANISM: Artificial Sequence
<220> FEATURE:
<223> OTHER INFORMATION: Mutant

<400> SEQUENCE: 25

Met His Val Ala Gln Pro Ala Val Val Leu Ala Ser Ser His Gly Leu
1               5                   10                  15

Ala Ser Phe Pro Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 26
<211> LENGTH: 125
<212> TYPE: PRT
<213> ORGANISM: Artificial Sequence
<220> FEATURE:
<223> OTHER INFORMATION: Mutant

<400> SEQUENCE: 26

Met His Val Ala Gln Pro Ala Val Val Leu Ala Ser Ser Arg Gly Ile
1               5                   10                  15

Ala Ser Phe Val Cys Glu Tyr Ala Ser Pro Ser His Asn Thr Asp Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 27
<211> LENGTH: 124
<212> TYPE: PRT
<213> ORGANISM: Artificial Sequence
<220> FEATURE:
<223> OTHER INFORMATION: Mutant

<400> SEQUENCE: 27
```

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Thr Asn Asp Gln Met Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 28
<211> LENGTH: 124
<212> TYPE: PRT
<213> ORGANISM: Artificial Sequence
<220> FEATURE:
<223> OTHER INFORMATION: Mutant

<400> SEQUENCE: 28

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Phe Thr Glu Lys Asn Thr Val Gly Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 29
<211> LENGTH: 124
<212> TYPE: PRT
<213> ORGANISM: Artificial Sequence
<220> FEATURE:
<223> OTHER INFORMATION: Mutant

<400> SEQUENCE: 29

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Thr Thr Tyr Met Met Gly Asn Glu Leu Thr Phe Leu Asp Asp Ser
```

```
            50                  55                  60
Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 30
<211> LENGTH: 124
<212> TYPE: PRT
<213> ORGANISM: Artificial
<220> FEATURE:
<223> OTHER INFORMATION: Mutant

<400> SEQUENCE: 30

Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Thr Glu Val
                 20                  25                  30

Arg Val Thr Val Leu Arg Gln Ala Asp Ser Gln Val Thr Glu Val Cys
             35                  40                  45

Ala Ala Thr Tyr Met Met Gly Asn Glu Leu Thr Phe Leu Asp Tyr Pro
         50                  55                  60

Phe Cys Ser Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 31
<211> LENGTH: 124
<212> TYPE: PRT
<213> ORGANISM: Artificial Sequence
<220> FEATURE:
<223> OTHER INFORMATION: Mutant

<400> SEQUENCE: 31

Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Thr Glu Val
                 20                  25                  30

Arg Val Thr Val Leu Arg Gln Ala Asp Ser Gln Val Thr Glu Val Cys
             35                  40                  45

Ala Ala Thr Tyr Met Met Gly Asn Glu Leu Thr Phe Leu Asp Asp Ser
         50                  55                  60

Ile Cys Thr Gly Thr Phe Asn Glu Ser Arg Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110
```

```
            Tyr Val Ile Asp Pro Glu Pro Cys Pro Asp Ser Asp
                115                 120

<210> SEQ ID NO 32
<211> LENGTH: 125
<212> TYPE: PRT
<213> ORGANISM: Artificial Sequence
<220> FEATURE:
<223> OTHER INFORMATION: Mutant

<400> SEQUENCE: 32

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Val Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 33
<211> LENGTH: 125
<212> TYPE: PRT
<213> ORGANISM: Artificial
<220> FEATURE:
<223> OTHER INFORMATION: Mutant

<400> SEQUENCE: 33

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Met Asp Thr Gly Leu Tyr Leu Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp
        115                 120                 125

<210> SEQ ID NO 34
<211> LENGTH: 124
<212> TYPE: PRT
<213> ORGANISM: Artificial Sequence
<220> FEATURE:
<223> OTHER INFORMATION: Mutant
```

<400> SEQUENCE: 34

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp
        115                 120

<210> SEQ ID NO 35
<211> LENGTH: 124
<212> TYPE: PRT
<213> ORGANISM: Artificial Sequence
<220> FEATURE:
<223> OTHER INFORMATION: Mutant

<400> SEQUENCE: 35

Ile Gln Val Thr Gln Pro Ser Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Phe Thr Glu Lys Asn Thr Val Gly Phe Leu Asp Asp Ser
    50                  55                  60

Ile Cys Thr Gly Thr Phe Asn Glu Ser Arg Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp
        115                 120

<210> SEQ ID NO 36
<211> LENGTH: 124
<212> TYPE: PRT
<213> ORGANISM: Artificial Sequence
<220> FEATURE:
<223> OTHER INFORMATION: Mutant

<400> SEQUENCE: 36

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

```
Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Val Gly Met Gly Asn Gly Thr Gln Ile
                100                 105                 110

Tyr Val Ile Asp Pro Glu Pro Cys Pro Asp Ser Asp
            115                 120

<210> SEQ ID NO 37
<211> LENGTH: 124
<212> TYPE: PRT
<213> ORGANISM: Artificial Sequence
<220> FEATURE:
<223> OTHER INFORMATION: Mutant

<400> SEQUENCE: 37

Ile Gln Val Thr Gln Pro Ser Val Val Leu Ala Ser Ser Arg Gly Ile
 1               5                  10                  15

Ala Ser Phe Val Cys Glu Tyr Ala Ser Pro Gly Lys Ala Thr Glu Val
                 20                  25                  30

Arg Val Thr Val Leu Arg Gln Ala Asp Ser Gln Val Thr Glu Val Cys
             35                  40                  45

Ala Ala Thr Phe Thr Glu Lys Asn Thr Val Gly Phe Leu Asp Asp Ser
        50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Phe Val Gly Met Gly Asn Gly Thr Gln Ile
                100                 105                 110

Tyr Val Ile Asp Pro Glu Pro Cys Pro Asp Ser Asp
            115                 120

<210> SEQ ID NO 38
<211> LENGTH: 124
<212> TYPE: PRT
<213> ORGANISM: Artificial Sequence
<220> FEATURE:
<223> OTHER INFORMATION: Mutant

<400> SEQUENCE: 38

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Tyr Thr Glu Val
                 20                  25                  30

Arg Val Thr Val Leu Arg Gln Ala Asp Ser Gln Val Thr Glu Val Cys
             35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Glu Gly Ile Gly Asn Gly Thr Gln Ile
                100                 105                 110
```

Tyr Val Ile Asp Pro Glu Pro Cys Pro Asp Ser Asp
        115                 120

<210> SEQ ID NO 39
<211> LENGTH: 124
<212> TYPE: PRT
<213> ORGANISM: Artificial Sequence
<220> FEATURE:
<223> OTHER INFORMATION: Mutant

<400> SEQUENCE: 39

Ile Gln Val Thr Gln Pro Ser Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Phe Thr Glu Lys Asn Thr Val Gly Phe Leu Asp Asp Ser
    50                  55                  60

Ile Cys Thr Gly Thr Phe Asn Glu Ser Arg Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp
        115                 120

<210> SEQ ID NO 40
<211> LENGTH: 124
<212> TYPE: PRT
<213> ORGANISM: Artificial Sequence
<220> FEATURE:
<223> OTHER INFORMATION: Mutant

<400> SEQUENCE: 40

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp
        115                 120

<210> SEQ ID NO 41
<211> LENGTH: 233
<212> TYPE: PRT
<213> ORGANISM: Homo sapiens

<400> SEQUENCE: 41

-continued

Gln Glu Pro Lys Ser Ser Asp Lys Thr His Thr Ser Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 42
<211> LENGTH: 357
<212> TYPE: PRT
<213> ORGANISM: Artificial Sequence
<220> FEATURE:
<223> OTHER INFORMATION: Fusion protein

<400> SEQUENCE: 42

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp Gln Glu Pro Lys
        115                 120                 125

```
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 43
<211> LENGTH: 357
<212> TYPE: PRT
<213> ORGANISM: Artificial Sequence
<220> FEATURE:
<223> OTHER INFORMATION: Fusion protein

<400> SEQUENCE: 43

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Glu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125
```

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 44
<211> LENGTH: 357
<212> TYPE: PRT
<213> ORGANISM: Artificial Sequence
<220> FEATURE:
<223> OTHER INFORMATION: Fusion protein

<400> SEQUENCE: 44

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Asp Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

```
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 45
<211> LENGTH: 357
<212> TYPE: PRT
<213> ORGANISM: Artificial Sequence
<220> FEATURE:
<223> OTHER INFORMATION: Fusion protein

<400> SEQUENCE: 45

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125
```

```
Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 46
<211> LENGTH: 124
<212> TYPE: PRT
<213> ORGANISM: Artificial Sequence
<220> FEATURE:
<223> OTHER INFORMATION: Mutant

<400> SEQUENCE: 46

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Met Gly Asn Gly Thr Gln Ile
            100                 105                 110

Tyr Val Ile Asp Pro Glu Pro Cys Pro Asp Ser Asp
        115                 120
```

<210> SEQ ID NO 47
<211> LENGTH: 124
<212> TYPE: PRT
<213> ORGANISM: Artificial Sequence
<220> FEATURE:
<223> OTHER INFORMATION: Mutant

<400> SEQUENCE: 47

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 48
<211> LENGTH: 124
<212> TYPE: PRT
<213> ORGANISM: Artificial Sequence
<220> FEATURE:
<223> OTHER INFORMATION: Mutant

<400> SEQUENCE: 48

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Asp Gly Ile Gly Asn Gly Thr Gln Ile
            100                 105                 110

Tyr Val Ile Asp Pro Glu Pro Cys Pro Asp Ser Asp
        115                 120

<210> SEQ ID NO 49
<211> LENGTH: 124
<212> TYPE: PRT
<213> ORGANISM: Artificial Sequence
<220> FEATURE:
<223> OTHER INFORMATION: Mutant

<400> SEQUENCE: 49

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
                35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Phe Val Gly Ile Gly Asn Gly Thr Gln Ile
            100                 105                 110

Tyr Val Ile Asp Pro Glu Pro Cys Pro Asp Ser Asp
            115                 120

<210> SEQ ID NO 50
<211> LENGTH: 6
<212> TYPE: PRT
<213> ORGANISM: Homo sapiens

<400> SEQUENCE: 50

Met Tyr Pro Pro Pro Tyr
1               5
```